US012692511B2

(12) United States Patent
Jarvis et al.

(10) Patent No.: US 12,692,511 B2
(45) Date of Patent: Jul. 28, 2026

(54) CELL SURFACE TAG EXCHANGE (CSTE) SYSTEM FOR TRACING AND MANIPULATION OF CELLS DURING RECOMBINASE MEDIATED CASSETTE EXCHANGE INTEGRATION OF NUCLEIC ACID SEQUENCES TO ENGINEERED RECEIVER CELLS

(71) Applicant: GENOVIE AB, Karlskrona (SE)

(72) Inventors: Reagan Micheal Jarvis, Karlskrona (SE); Luke Benjamin Pase, Karlskrona (SE); Ryan Edward Hill, Karlskrona (SE)

(73) Assignee: GENOVIE AB, Södertälje (SE)

( * ) Notice: Subject to any disclaimer, the term of this patent is extended or adjusted under 35 U.S.C. 154(b) by 1497 days.

(21) Appl. No.: 17/259,003

(22) PCT Filed: Jul. 9, 2019

(86) PCT No.: PCT/EP2019/068343
§ 371 (c)(1),
(2) Date: Jan. 8, 2021

(87) PCT Pub. No.: WO2020/011757
PCT Pub. Date: Jan. 16, 2020

(65) Prior Publication Data
US 2021/0371875 A1 Dec. 2, 2021

(30) Foreign Application Priority Data
Jul. 9, 2018 (EP) ..................................... 18182353

(51) Int. Cl.
| *C12N 15/85* | (2006.01) |
| *C12N 15/10* | (2006.01) |
| *C12N 15/90* | (2006.01) |

(52) U.S. Cl.
CPC ......... *C12N 15/85* (2013.01); *C12N 15/1086* (2013.01); *C12N 15/907* (2013.01); *C12N 2800/107* (2013.01); *C12N 2800/30* (2013.01); *C12N 2830/00* (2013.01)

(58) Field of Classification Search
None
See application file for complete search history.

(56) References Cited

U.S. PATENT DOCUMENTS

| 11,274,309 | B2 * | 3/2022 | Jarvis | ................. | C07K 14/7051 |
| 12,012,610 | B2 * | 6/2024 | Jarvis | .................... | C12N 15/85 |
| 2021/0371875 | A1 * | 12/2021 | Jarvis | .................... | C12N 15/79 |

FOREIGN PATENT DOCUMENTS

| WO | WO 2014-085711 A1 | 6/2014 |
| WO | WO 2017/186718 A | 11/2017 |
| WO | WO 2018-083316 A1 | 5/2018 |
| WO | WO 2018-083317 A1 | 5/2018 |

OTHER PUBLICATIONS

Office Action for JP 2021-500636 issued May 30, 2023.
Cobellis et al., "Tagging genes with cassette-exchange sites," Nucleic Acids Research, vol. 33, No. 4, e44, pp. 1-7 (2005).
Phan et al., "Site-specific chromosomal gene insertion: Flp recombinase versus Cas9 nuclease," Scientific Reports, vol. 7, No. 17771, pp. 1-12 (2017) (Published online Dec. 2017).
Turan et al., "Recombinase-mediated cassette exchange (RMCE)—A rapidly-expanding toolbox for targeted genomic modifications," Gene., vol. 515, (2013) pp. 1-27.

* cited by examiner

*Primary Examiner* — Nancy J Leith
(74) *Attorney, Agent, or Firm* — KNOBBE, MARTENS, OLSON & BEAR, LLP

(57) ABSTRACT

A combined system comprising two separate components, wherein the first component is a tag-exchange donor vector (TEDV) encoding a first cell surface tag (CST) exon flanked by a 3' intron fragment, and a gene of interest (GOI) in the antisense orientation, and the second component is an engineered cell containing within its genome a tag-exchange receiver site (TERS), encoding a second CST exon adjoined by a full intron sequence to an exon encoding a transmembrane domain, and also encoding a reporter gene in the antisense orientation, wherein paired recombinase mediated cassette exchange (RMCE) elements are included in the TEDV and TERS such that execution of RMCE between the TEDV and TERS results in exchange of the reporter element for the GOI encoded by the TEDV, and exchange of the first CST exon for the second CST exon, such that the derivative engineered cell now expresses the first CST and GOI, in place of the second CST and the reporter gene.

16 Claims, 11 Drawing Sheets

Specification includes a Sequence Listing.

TEDV encoding GOI          +          engineered cell containing TERS derivative engineered cell expressing GOI

TEDV

TERS exchanged TERS of derivative engineered cell exchanged TEDV by-product a b

1. Molecular Weight marker (KDa)
2. ACL-3374 RSV-1 P-gene
3. ACL-3386 RSV-1 N-gene
4. ACL-3433 RSV-1 M2-gene long
5. ACL-1163 Parental a b c 96.52%  GOI positive cells
3.48%  GOI negative cells

Total=546 integrants a pool of barcoded TEDV engineered cell containing TERS pool of derivative engineered cell expressing a GOI

| | MFI of Live Cells | | | % Cells in Positive Gate | | |
|---|---|---|---|---|---|---|
| Sample | FLAG | MYC | HA | FLAG | MYC | HA |
| HEK - Barcoded | 15529 | 834 | 591 | 98.7 | 93.5 | 72.7 |
| HEK - Empty Vector | 31 | 48 | 122 | 0.1 | 0.1 | 0.2 |
| Jurkat - Barcoded | 11300 | 3273 | 573 | 76.0 | 87.0 | 63.9 |
| Jurkat - Empty Vector | 32 | 57 | 106 | 0.3 | 5.0 | 0.3 |

SEQUENCE LISTING

```
<160> NUMBER OF SEQ ID NOS: 23

<210> SEQ ID NO 1
<211> LENGTH: 5837
<212> TYPE: DNA
<213> ORGANISM: Artificial sequence
<220> FEATURE:
<223> OTHER INFORMATION: Tag-exchange receiver site encoding Myc CST and
      RFP selection gene

<400> SEQUENCE: 1
gagctctact ggcttctgcg ccgcctctgg cccactgttt ccccttccca ggcaggtcct      60
gctttctctg acctgcattc tctcccctgg gcctgtgccg ctttctgtct gcagcttgtg     120
gcctgggtca cctctacggc tggcccagat ccttccctgc cgcctccttc aggttccgtc     180
ttcctccact ccctcttccc cttgctctct gctgtgttgc tgcccaagga tgctctttcc     240
ggagcacttc cttctcggcg ctgcaccacg tgatgtcctc tgagcggatc ctccccgtgt     300
ctgggtcctc tccgggcatc tctcctccct cacccaaccc catgccgtct tcactcgctg     360
ggttcccttt tccttctcct tctgggggcct gtgccatctc tcgtttctta ggatggcctt     420
ctccgacgga tgtctccctt gcgtcccgcc tccccttctt gtaggcctgc atcatcaccg     480
tttttctgga caacccccaaa gtacccgtc tccctggctt tagccacctc tccatcctct     540
tgctttcttt gcctggacac cccgttctcc tgtggattcg ggtcacctct cactcctttc     600
atttgggcag ctcccctacc cccttacct ctctagtctg tgctagctct tccagccccc     660
tgtcatggca tcttccaggg gtccgagagc tcagctagtc ttcttcctcc aacccgggcc     720
cctatgtcca cttcaggaca gcatgtttgc tgcctccagg gatcctgtgt cccgagctg      780
```

-continued

```
ggaccacctt atattcccag ggccggttaa tgtggctctg gttctgggta cttttatctg    840
tcccctccac cgggtggctc cggtgcccgt cagtgggcag agcgcacatc gcccacagtc    900
cccgagaagt tggggggagg ggtcggcaat tgaaccggtg cctagagaag gtggcgcggg    960
gtaaactggg aaagtgatgt cgtgtactgg ctccgccttt ttcccgaggg tggggggagaa   1020 ccgtatataa gtgcagtagt cgccgtgaac gttcttttc gcaacgggtt tgccgccaga    1080
acacaggtaa gtgccgtgtg tggttcccgc gggcctggcc tctttacggg ttatggccct    1140
tgcgtgcctt gaattacttc cactggctgc agtacgtgat tcttgatccc gagcttcggg    1200
ttggaagtgg gtgggagagt tcgaggcctt gcgcttaagg agccccttcg cctcgtgctt    1260
gagttgaggc ctggcctggg cgctggggcc gccgcgtgcg aatctggtgg caccttcgcg    1320
cctgtctcgc tgctttcgat aagtctctag ccatttaaaa ttttttgatga cctgctgcga    1380 cgcttttttt ctggcaagat agtcttgtaa atgcgggcca agatctgcac actggtattt    1440 cggttttgg ggccgcgggc ggcgacgggg cccgtgcgtc ccagcgcaca tgttcggcga    1500
ggcggggcct gcgagcgcgg ccaccgagaa tcggacgggg gtagtctcaa gctggccggc    1560
ctgctctggt gcctggcctc gcgccgccgt gtatcgcccc gccctgggcg gcaaggctgg    1620
cccggtcggc accagttgcg tgagcggaaa gatggccgct tccggcccct gctgcaggga    1680
gctcaaaatg gaggacgcgg cgctcgggag agcgggcggg tgagtcaccc acacaaagga    1740
aaagggcctt tccgtcctca gccgtcgctt catgtgactc cacggagtac cgggcgccgt    1800
ccaggcacct cgattagttc tcgagctttt ggagtacgtc gtctttaggt tggggggagg    1860
ggttttatgc gatggagttt ccccacactg agtgggtgga gactgaagtt aggccagctt    1920
ggcacttgat gtaattctcc ttggaatttg ccctttttga gtttggatct tggttcattc    1980
tcaagcctca gacagtggtt caaagttttt ttcttccatt tcaggtgtcg tgactgctta    2040
agcttggtac cgccaccatg gccaagggct tctacatcag caagagcctg ggcatcctgg    2100
gaatcctgct gggagtggct gctgtgtgca ccatcatcgc tctgagcgtg gtgtacagcc    2160
aggagggagg tcctggatcc ggaacaggtg gctctggcac tggaggatca ggtccaggtg    2220
gatctatggt gaagcagatc gagagcaaga ctgctttcca ggaagccttg gacgctgcag    2280
gtgataagct tgtagtagtt gacttctcag caacgtggtc tggaccttcc aagatgatca    2340
agcctttctt ccattccctc tctgagaagt attccaacgt gatattcctt gaagtagatg    2400
tggatgactc tcaggatgtt gcttcagagt gtgaagtcaa atccatgcca acattccagt    2460
tcttcaagaa gggacagaag gtgggtgaat tttctggagc caataaggag aagcttgaag    2520
ccaccattaa cgagttggta ggtaagtggc tggggccaga gactggctct tgaagttcct    2580
attccgaagt tcctattctc tagaaagtat aggaacttcc tggctcagaa aaagggccct    2640
gacaactctt ttcatcttct aggcggttcc tctacatccg gtggatctgg atctggagaa    2700
caaaagctca tctctgagga ggaccttggg gagcagaagc taatcagtga agaagacctc    2760
ggagagcaga aattgattag cgaggaggat ctttaaagac gctagcacct gatcctgatc    2820
ataatcaagc catatcacat ctgtagaggt ttacttgctt taaaaaacct ccacacctcc    2880
ccctgaacct gaaacataaa atgaatgcaa ttgttgttgt taacttgttt attgcagctt    2940
ataatggtta caaataaagc aatagcatca caaatttcac aaataaagca tttttttcac    3000
tgcattctag ttgtggtttg tccaaactca tcaatgtatc ttatcatgtc tggatctgct    3060
gaagagcgct gatcagctct tcaccataga gcccaccgca tccccagcat gcctgctatt    3120
```

-continued

```
gtcttcccaa tcctccccct tgctgtcctg ccccacccca cccccagaa tagaatgaca    3180 cctactcaga caatgcgatg caatttcctc attttattag gaaaggacag tgggagtggc    3240
accttccagg gtcaaggaag gcacgggggga gggggcaaaca acagatggct ggcaactaga   3300
aggcacagtc gggtgctagc tcatctgtgg cccagcttgc taggcaggtc gcagtacttg    3360
gccacggcca tctcgtgctg ttccacgtag gtttctttgt cggcctcttt gatccgttcc    3420
agccggtggt ccacgaagtg gaagccgggc atcttcaggt tcttggcggg cttcttgctt    3480
ctgtaggtgg tcttgaagga gcagtgcagg tagcctccgc ccacgagttt cagggccatc    3540
tgagaatggc ctctcaggcc gccatcggca gggtacagca tctcggtgtt ggcctcccag    3600
cctctggttt tcttctgcat cacggggccg ttgctgggga agttcacgcc gttaatcttc    3660
acgttgtaga tgatgcagcc gttctggaag ctggtatcct gggtggcggt cagcactccg    3720
ccgtcctcgt atgtggtgat ccgctcccag gtgaagccct cggggaagct ctgcttgaag    3780
aaatcgggga tgccctgggt gtggttgatg aaggccttgc tgccgtacat aaagctggtg    3840
gccaggatat caaaggcgaa gggcagaggg ccgccttcca ccaccttgat cttcatggtc    3900
tgggtgccct cgtaaggctt gccctcgccc tcgctggtgc acttgaagtg gtggttgttc    3960
acggtgcctt ccatgtacag cttcatgtgc atgttttctt tgatcagctc gctcatggtg    4020
gctacggaag ttcctattcc gaagttccta ttcttcaaat agtataggaa cttccggtac    4080
cagtcacgac acctgaaatg gaagaaaaaa actttgaacc actgtctgag gcttgagaat    4140
gaaccaagat ccaaactcaa aaagggcaaa ttccaaggag aattacatca agtgccaagc    4200
tggcctaact tcagtctcca cccactcagt gtggggaaac tccatcgcat aaaacccctc    4260
cccccaacct aaagacgacg tactccaaaa gctcgagaac taatcgaggt gcctggacgg    4320
cgcccggtac tccgtggagt cacatgaagc gacggctgag gacggaaagg cccttttcct    4380
ttgtgtgggt gactcacccg cccgctctcc cgagcgccgc gtcctccatt ttgagctccc    4440
tgcagcaggg ccgggaagcg gccatctttc cgctcacgca actggtgccg accgggccag    4500
ccttgccgcc cagggcgggg cgatacacgg cggcgcgagg ccaggcacca gagcaggccg    4560
gccagcttga gactaccccc gtccgattct cggtggccgc gctcgcaggc cccgcctcgc    4620
cgaacatgtg cgctgggacg cacgggcccc gtcgccgccc gcggccccaa aaaccgaaat    4680
accagtgtgc agatcttggc ccgcatttac aagactatct tgccagaaaa aaagcgtcgc    4740
agcaggtcat caaaaatttt aaatggctag agacttatcg aaagcagcga gacaggcgcg    4800
aaggtgccac cagattcgca cgcggcggcc ccagcgccca ggccaggcct caactcaagc    4860
acgaggcgaa ggggctcctt aagcgcaagg cctcgaactc tcccacccac ttccaacccg    4920
aagctcggga tcaagaatca cgtactgcag ccagtggaag taattcaagg cacgcaaggg    4980
ccataacccg taaagaggcc aggcccgcgg gaaccacaca cggcacttac ctgtgttctg    5040
gcggcaaacc cgttgcgaaa aagaacgttc acggcgacta ctgcacttat atacggttct    5100
cccccaccct cgggaaaaag gcggagccag tacacgacat cactttccca gtttaccccg    5160
cgccaccttc tctaggcacc ggttcaattg ccgacccctc cccccaactt ctcggggact    5220
gtgggcgatg tgcgctctgc ccactgacgg gcaccggagc caccggatca ggatcaggat    5280
tggtgacaga aaagccccat ccttaggcct cctccttcct agtctcctga tattgggtct    5340 aaccccacc tcctgttagg cagattcctt atctggtgac acaccccat ttcctggagc      5400 catctctctc cttgccagaa cctctaaggt ttgcttacga tggagccaga gaggatcctg    5460
ggagggagag cttggcaggg ggtgggaggg aaggggggga tgcgtgacct gcccggttct    5520
```

```
cagtggccac cctgcgctac cctctcccag aacctgagct gctctgacgc ggctgtctgg      5580
tgcgtttcac tgatcctggt gctgcagctt ccttacactt cccaagagga gaagcagttt      5640
ggaaaaacaa aatcagaata agttggtcct gagttctaac tttggctctt cacctttcta      5700
gtccccaatt tatattgttc ctccgtgcgt cagtttacc tgtgagataa ggccagtagc       5760
cagccccgtc ctggcagggc tgtggtgagg aggggggtgt ccgtgtggaa aactcccttt      5820
gtgagaatgg tgcgtcc                                                     5837
```

<210> SEQ ID NO 2
<211> LENGTH: 1332
<212> TYPE: DNA
<213> ORGANISM: Artificial sequence
<220> FEATURE:
<223> OTHER INFORMATION: Flippase

<400> SEQUENCE: 2

```
atggccccca agaaaaagcg gaaagtgggc atccacggcg tgccagctgc aggcggctct        60
atgagccagt tcgacatcct gtgcaagacc ccacctaagg tgctcgtgcg gcagttcgtg       120
gaaagattcg agaggcctag cggcgagaag atcgcctctt gtgctgccga gctgacctac       180
ctgtgctgga tgatcaccca caacggcacc gccatcaagc gggccacctt catgagctac       240
aataccatca tcagcaacag cctgagcttc gacatcgtga acaagagcct gcagttcaag       300
tacaagaccc agaaggccac catcctggaa gccagcctga gaaactgat ccccgcctgg        360 gagtttacca tcatcccata caatggccag aaacatcaga gcgacattac cgatatcgtg       420
tccagcctcc agctgcagtt cgagagtagc gaagaagccg acaagggcaa cagccacagc       480
aagaagatgc tgaaggccct gctgagcgag ggcgagagca tctgggagat cacagagaag       540
atcctgaaca gcttcgagta caccagccgg ttcaccaaga ccaagaccct gtaccagttc       600
ctgttcctgg ccacctttat caactgcggc cggttctccg acatcaagaa cgtggacccc       660
aagagcttca agctggtgca gaacaagtac ctgggcgtga tcattcagtg cctcgtgacc       720
gagacaaaga ccagcgtgtc ccggcacatc tactttttca gcgccagagg ccggatcgac       780
cccctggtgt acctggacga gttcctgaga aacagcgagc ccgtgctgaa gagagtgaac       840
cggaccggca acagcagctc caacaagcag gaataccagc tgctgaagga caacctcgtg       900
cggtcctaca caaggccct gaagaaaaac gcccctacc ccatcttcgc cattaagaac         960
ggccccaagt cccacatcgg ccggcacctg atgaccagct ttctgagcat gaagggcctg      1020
acagagctga ccaacgtcgt gggcaattgg agcgacaaga gggcctctgc cgtggccaga      1080
accacctaca cccaccagat cacagccatc cccgaccact acttcgccct ggtgtctcgg      1140
tactacgcct acgaccccat cagcaaagag atgatcgccc tgaaggacga gacaaacccc      1200
atcgaggaat ggcagcacat cgagcagctg aagggcagcg ccgagggcag catcagatac      1260
cctgcctgga acggcatcat ctcccaggaa gtgctggact acctgagcag ctacatcaac      1320
cggcggatct ga                                                         1332
```

<210> SEQ ID NO 3
<211> LENGTH: 1791
<212> TYPE: DNA
<213> ORGANISM: Artificial sequence
<220> FEATURE:
<223> OTHER INFORMATION: TEDV encoding SBP CST and P-gene_RSV1 GOI

<400> SEQUENCE: 3

-continued

```
gaagttccta ttccgaagtt cctattctct agaaagtata ggaacttcct ggctcagaaa      60
aagggccctg acaactcttt tcatcttcta ggcggttcct ctacatccgg tggatctgga     120
tctgggcatg tggttgaggg gcttgctggc gaactagagc aattgcgagc ccgcctcgaa     180
caccatcctc aaggtcaata aagactcgag cacctgatcc tgatcataat caagccatat     240
cacatctgta gaggtttact tgctttaaaa aacctccaca cctccccctg aacctgaaac     300
ataaaatgaa tgcaattgtt gttgttaact tgtttattgc agcttataat ggttacaaat     360
aaagcaatag catcacaaat ttcacaaata aagcattttt ttcactgcat tctagttgtg     420
gtttgtccaa actcatcaat gtatcttatc atgtctggat ctgctgaaga gcgctgatca     480
gctcttcacc atagagccca ccgcatcccc agcatgcctg ctattgtctt cccaatcctc     540
ccccttgctg tcctgcccca ccccacccccc cagaatagaa tgacacctac tcagacaatg     600
cgatgcaatt tcctcatttt attaggaaag gacagtggga gtggcacctt ccagggtcaa     660
ggaaggcacg ggggaggggc aaacaacaga tggctggcaa ctagaaggca cagtcgggtg     720
ctagcgaaga ccgagcggtg gatccgtatg gtgacaagac gactagtgtg aacgactaga     780
aagagaaccc ggcacatctg tcgagaggta cgaccgtgca ctaagcttcg caaggtcagt     840
ggagctatcg agtgtaggat ggttcaagtc tgccaatgga gctacagaag tcgaagccgt     900
ccagatctgg actatagtca cttatcgtca tcgtccttat aatcaatatc gtggtcttta     960
taatctccat catgatcctt gtaatccccg gggaaatctt ccaggctcag gtcgttgtcg    1020
ctgtcgttgc cttccagcag gttgttcagc ttctcagagg tagggttcag agacacttcg    1080
tcggaggtgt ccttggccat cttctcggat tcctcgtttc tcagccgggc catagcttcc    1140
agccgatcgt tggtcatcag ggcctctgtc cggatcttct cgatcatctc ttcccgcagt    1200
ccgaccatgg catctctgat gccatctctg cagatgtag gtccggcaga tgccaccacc    1260
agtgtgtgca gcatgcccag gatctcagac agcttctcgt cgatccggtc cagtctggcg    1320
gtgatgttgt cgttggtctg gtcgttgatt tcctcgtagc tgtagctgct ctcttcctcg    1380
ttgttgtcga atgtctcgat tgtctctttg tacagcttgc tgaaggggtt gtcgctaggt    1440
gtggggtcct ctttgaagga caccaggggc tttctctggt agttgggctt gttgccggcg    1500
gtgtcgtctg tctcgttggt ggggttgatg atggtgctgt tgctggtgat ggggctctct    1560
ttggtcactt cgatgtcgat gctgttcacg ctgatgatgc tgtccttctt cttggggtcc    1620
ttggggctcg tgaacttgcc cttgatggat tccagaaact tggtggcccg attgttggcg    1680
tcctcgccgt ggaactcagg ggcgaacttt tccatggtgg cggtattgtc ttcggtaccg    1740
cacgaagttc ctattcggaa gttcctattc ttcaaatagt ataggaactt c            1791
```

<210> SEQ ID NO 4
<211> LENGTH: 2241
<212> TYPE: DNA
<213> ORGANISM: Artificial sequence
<220> FEATURE:
<223> OTHER INFORMATION: TEDV encoding SBP CST and N-gene_RSV1 GOI

<400> SEQUENCE: 4

```
gaagttccta ttccgaagtt cctattctct agaaagtata ggaacttcct ggctcagaaa      60
aagggccctg acaactcttt tcatcttcta ggcggttcct ctacatccgg tggatctgga     120
tctgggcatg tggttgaggg gcttgctggc gaactagagc aattgcgagc ccgcctcgaa     180
caccatcctc aaggtcaata aagactcgag cacctgatcc tgatcataat caagccatat     240
cacatctgta gaggtttact tgctttaaaa aacctccaca cctccccctg aacctgaaac     300
```

-continued

```
ataaaatgaa tgcaattgtt gttgttaact tgtttattgc agcttataat ggttacaaat     360
aaagcaatag catcacaaat ttcacaaata aagcattttt ttcactgcat tctagttgtg     420
gtttgtccaa actcatcaat gtatcttatc atgtctggat ctgctgaaga gcgctgatca     480
gctcttcacc atagagccca ccgcatcccc agcatgcctg ctattgtctt cccaatcctc     540
ccccttgctg tcctgcccca ccccacccccc cagaatagaa tgacacctac tcagacaatg     600
cgatgcaatt tcctcatttt attaggaaag gacagtggga gtggcacctt ccagggtcaa     660
ggaaggcacg ggggaggggc aaacaacaga tggctggcaa ctagaaggca cagtcgggtg     720
ctagcgaaga ccgagcggtg gatccgtatg gtgacaagac gactagtgtg aacgactagg     780
gagagaaccc ggcacatctg tcgagaggta cgaccgtgca ctaagcttcg caaggtcagt     840
ggagctatcg agtgtaggat ggttcaagtc tgccaatgga gctacagaag tcgaagccgt     900
ccagatctgg actatagtca cttatcgtca tcgtccttat aatcaatatc gtggtcttta     960
taatctccat catgatcctt gtaatccccg ggcagttcca cgtcgttgtc cttagggttc    1020
agctggtgct tgatggcttc cagttcctcg gcggtcagat ccagcacgct gtagttgatc    1080
acgccgtttt ctttcagctg ctcggcatag gccttggcgg catcgtacag gtcctggttt    1140
ctaggggtgc ctctgtactc gcccatgatt cccagtccgg cggcatttcc cagcaccaca    1200
gagctgaagt gtgggaactg tgtcaggctc agcagagagg ccttgggggtt gttcaggatg    1260 tggtaaaagc cggcctctcc gccaagcttc tgggcgtact cgtacacttc caccacctgt    1320
tccatttcgg cctgcacaga ggcgtggccc agcatgatgt tcttcacgct cttggccagc    1380
actccccatc tcagcatcac ttgtccggcg ccataggcat tcatgaacag gccggcgaag    1440
atgccttcca cccgagagcc gcctcttgtg ctgctctggg cgattccgaa gtgcacgaac    1500
acgtcgatga agtgagggta cttctcgaac acctcgtaga agctgttggc aatatcctta    1560
ggcagcaggc ccttgtaccg cttcatctcg ttcttcagca cgttgttggc tctccgaatc    1620
acagcggtca ggccagaccg atcgccagcg gccagtttgg tgatgaccag agcggcgata    1680
cacaggatga tcatgccgca atcagggctg tcgtgtctgt actcagggggc gacttcgccc    1740 atctctttca gcattttctt gtaggacttc cggctctcga tctcgatgtt gatctggatc    1800
tctgtggtca ggctggccag ggtcagcacc tcgaacttca tttctttgcc gttgatgtcc    1860
tgccggtgtg tggtcacgtc cacgccattg gccttcacgt ggtagccggc atctctcagg    1920
atcttgatgg tgtcctctct gcccagtctg ctcatggcgt acagcattcc gatcacgcct    1980
gtgaacttgt ggttggcgtc ctcggtgatc agcagcatgc cgcacagctt gttgatgtgc    2040
ttctgcacgt cgtagttagg ggtgtcgatg ctgtcgccgg tgcttctctg gatggtgtac    2100
ttgctgctgc tcagcagctg gtccttgttc agggtgtcgt tcagcttcac tttgctcagg    2160
gccatggtgg cggtattgtc ttcggtaccg cacgaagttc ctattcggaa gttcctattc    2220
ttcaaatagt ataggaactt c                                               2241
```

<210> SEQ ID NO 5
<211> LENGTH: 1649
<212> TYPE: DNA
<213> ORGANISM: Artificial sequence
<220> FEATURE:
<223> OTHER INFORMATION: M2-long-gene_RSV1

<400> SEQUENCE: 5

```
gaagttccta ttccgaagtt cctattctct agaaagtata ggaacttcct ggctcagaaa      60
```

-continued

```
aagggccctg acaactcttt tcatcttcta ggcggttcct ctacatccgg tggatctgga      120
tctgggcatg tggttgaggg gcttgctggc gaactagagc aattgcgagc ccgcctcgaa      180
caccatcctc aaggtcaata aagactcgag cacctgatcc tgatcataat caagccatat      240
cacatctgta gaggtttact tgctttaaaa aacctccaca cctccccctg aacctgaaac      300
ataaaatgaa tgcaattgtt gttgttaact tgtttattgc agcttataat ggttacaaat      360
aaagcaatag catcacaaat ttcacaaata aagcattttt ttcactgcat tctagttgtg      420
gtttgtccaa actcatcaat gtatcttatc atgtctggat ctgctgaaga gcgctgatca      480
gctcttcacc atagagccca ccgcatcccc agcatgcctg ctattgtctt cccaatcctc      540 cccccttgctg tcctgcccca ccccacccccc cagaatagaa tgacacctac tcagacaatg      600
cgatgcaatt tcctcatttt attaggaaag gacagtggga gtggcacctt ccagggtcaa      660
ggaaggcacg ggggaggggc aaacaacaga tggctggcaa ctagaaggca cagtcgggtg      720
ctagcgaaga ccgagcggtg gatccgtatg gtgacaagac gactagtgtg aacgacctgt      780
tagagaaccc ggcacatctg tcgagaggta cgaccgtgca ctaagcttcg caaggtcagt      840
ggagctatcg agtgtaggat ggttcaagtc tgccaatgga gctacagaag tcgaagccgt      900
ccagatctgg actatagtca cttatcgtca tcgtccttat aatcaatatc gtggtcttta      960
taatctccat catgatcctt gtaatccccg ggggtggtat cgttgttctt ggcgtggtcg     1020
ttggtgtcgt tgacggtgct ctctttggga ttgttgatgg tgatgctctt gtggatgtcc     1080
agggtgttct tgatggtttt cttcagcacg tcggcaggca gccgcttcag cagatggatg     1140
gtctgcttgt tgttcttccg gttgctctcg atgtagctga tcacggtgtt gtacacccgg     1200
atcttggggc tgttaggttc ctcgttgtcc cgcagcttct tgatgtcgtc gctgttcagc     1260
tctgtcagca gcttgctcat ggccacgcag gcgctctgct tggtgatgtt gttgatgctg     1320
ccgatatagc tttccagcac gcccacaacg cccagggcat attcctcggt tctatccagt     1380
tcggcggctc cgctgatctc gctcagggtg tcgatgctct tatccatgga cttcaggatt     1440
ctgttcagca tgaagttctg ccgcacgagc agagcgtgag gaggccactc gaagtagttg     1500
tggctgaagt ggcatctctt gccgttcagg cagtggcctc tgatctcgaa cttgcagggg     1560
ttccgtctgc tcatggtggc ggtattgtct tcggtaccgc acgaagttcc tattcggaag     1620
ttcctattct tcaaatagta taggaactt                                        1649
```

```
<210> SEQ ID NO 6
<211> LENGTH: 4542
<212> TYPE: DNA
<213> ORGANISM: Artificial sequence
<220> FEATURE:
<223> OTHER INFORMATION: CMVpro-Flp-sv40pA-V2 vector V4.I.8

<400> SEQUENCE: 6
```

```
ctaaattgta agcgttaata ttttgttaaa attcgcgtta aatttttgtt aaatcagctc       60
attttttaac caataggccg aaatcggcaa aatcccttat aaatcaaaag aatagaccga      120
gatagggttg agtggccgct acagggcgct cccattcgcc attcaggctg cgcaactgtt      180
gggaagggcg tttcggtgcg ggcctcttcg ctattacgcc agctggcgaa aggggggatgt      240 gctgcaaggc gattaagttg ggtaacgcca gggttttccc agtcacgacg ttgtaaaacg      300
acggccagtg agcgcgacgt aatacgactc actataggc gaattggcgg aaggccgtca      360
aggccgcatg aattcgctac cggtatagta atcaattacg gggtcattag ttcatagccc      420
atatatggag ttccgcgtta cataacttac ggtaaatggc ccgcctggct gaccgcccaa      480
```

```
cgacccccgc ccattgacgt caataatgac gtatgttccc atagtaacgc caatagggac      540
tttccattga cgtcaatggg tggagtattt acggtaaact gcccacttgg cagtacatca      600
agtgtatcat atgccaagta cgccccctat tgacgtcaat gacggtaaat ggcccgcctg      660
gcattatgcc cagtacatga ccttatggga ctttcctact tggcagtaca tctacgtatt      720
agtcatcgct attaccatgg tgatgcggtt ttggcagtac atcaatgggc gtggatagcg      780
gtttgactca cggggatttc caagtctcca ccccattgac gtcaatggga gtttgttttg      840
gcaccaaaat caacgggact ttccaaaatg tcgtaacaac tccgccccat tgacgcaaat      900
gggcggtagg cgtgtacggt gggaggtcta tataagcaga gctggtttag tgaaccgtca      960
gatcaggtac catggccccc aagaaaaagc ggaaagtggg catccacggc gtgccagctg     1020
caggcggctc tatgagccag ttcgacatcc tgtgcaagac cccacctaag gtgctcgtgc     1080
ggcagttcgt ggaaagattc gagaggccta gcggcgagaa gatcgcctct tgtgctgccg     1140
agctgaccta cctgtgctgg atgatcaccc acaacggcac cgccatcaag cgggccacct     1200
tcatgagcta caataccatc atcagcaaca gcctgagctt cgacatcgtg aacaagagcc     1260
tgcagttcaa gtacaagacc cagaaggcca ccatcctgga agccagcctg aagaaactga     1320
tccccgcctg ggagtttacc atcatcccat acaatggcca gaaacatcag agcgacatta     1380
ccgatatcgt gtccagcctc cagctgcagt tcgagagtag cgaagaagcc gacaagggca     1440
acagccacag caagaagatg ctgaaggccc tgctgagcga gggcgagagc atctgggaga     1500
tcacagagaa gatcctgaac agcttcgagt acaccagccg gttcaccaag accaagaccc     1560
tgtaccagtt cctgttcctg gccaccttta tcaactgcgg ccggttctcc gacatcaaga     1620
acgtggaccc caagagcttc aagctggtgc agaacaagta cctgggcgtg atcattcagt     1680
gcctcgtgac cgagacaaag accagcgtgt cccggcacat ctactttttc agcgccagag     1740
gccggatcga cccctggtg tacctggacg agttcctgag aaacagcgag cccgtgctga     1800
agagagtgaa ccggaccggc aacagcagct ccaacaagca ggaataccag ctgctgaagg     1860
acaacctcgt gcggtcctac aacaaggccc tgaagaaaaa cgcccctac cccatcttcg     1920 ccattaagaa cggccccaag tcccacatcg gccggcacct gatgaccagc tttctgagca     1980
tgaagggcct gacagagctg accaacgtcg tgggcaattg gagcgacaag agggcctctg     2040
ccgtggccag aaccacctac acccaccaga tcacagccat ccccgaccac tacttcgccc     2100
tggtgtctcg gtactacgcc tacgacccca tcagcaaaga gatgatcgcc ctgaaggacg     2160
agacaaaccc catcgaggaa tggcagcaca tcgagcagct gaagggcagc gccgagggca     2220
gcatcagata ccctgcctgg aacggcatca tctcccagga agtgctggac tacctgagca     2280
gctacatcaa ccggcggatc tgatctagac ctgatcataa tcaagccata tcacatctgt     2340
agaggtttac ttgctttaaa aaacctccac acctccccct gaacctgaaa cataaaatga     2400
atgcaattgt tgttgttaac ttgtttattg cagcttataa tggttacaaa taaagcaata     2460
gcatcacaaa tttcacaaat aaagcatttt tttcactgca ttctagttgt ggtttgtcca     2520
aactcatcaa tgtatcttat catgtctgga tctgcggatc caatctcgag ctgggcctca     2580
tgggccttcc gctcactgcc cgctttccag tcgggaaacc tgtcgtgcca gctgcattaa     2640
catggtcata gctgtttcct tgcgtattgg gcgctctccg cttcctcgct cactgactcg     2700
ctgcgctcgg tcgttcgggt aaagcctggg gtgcctaatg agcaaaaggc cagcaaaagg     2760
ccaggaaccg taaaaaggcc gcgttgctgg cgttttttcca taggctccgc cccctgacg     2820
```

-continued

```
agcatcacaa aaatcgacgc tcaagtcaga ggtggcgaaa cccgacagga ctataaagat    2880
accaggcgtt tccccctgga agctccctcg tgcgctctcc tgttccgacc ctgccgctta    2940
ccggatacct gtccgccttt ctcccttcgg aagcgtggc gctttctcat agctcacgct     3000
gtaggtatct cagttcggtg taggtcgttc gctccaagct gggctgtgtg cacgaacccc    3060
ccgttcagcc cgaccgctgc gccttatccg gtaactatcg tcttgagtcc aacccggtaa    3120
gacacgactt atcgccactg gcagcagcca ctggtaacag gattagcaga gcgaggtatg    3180
taggcggtgc tacagagttc ttgaagtggt ggcctaacta cggctacact agaagaacag    3240
tatttggtat ctgcgctctg ctgaagccag ttaccttcgg aaaaagagtt ggtagctctt    3300
gatccggcaa acaaaccacc gctggtagcg gtggtttttt tgtttgcaag cagcagatta    3360
cgcgcagaaa aaaaggatct caagaagatc ctttgatctt ttctacgggg tctgacgctc    3420
agtggaacga aaactcacgt taagggattt tggtcatgag attatcaaaa aggatcttca    3480
cctagatcct tttaaattaa aaatgaagtt ttaaatcaat ctaaagtata tatgagtaaa    3540
cttggtctga cagttaccaa tgcttaatca gtgaggcacc tatctcagcg atctgtctat    3600
ttcgttcatc catagttgcc tgactccccg tcgtgtagat aactacgata cgggagggct    3660
taccatctgg ccccagtgct gcaatgatac cgcgagaacc acgctcaccg gctccagatt    3720
tatcagcaat aaaccagcca gccggaaggg ccgagcgcag aagtggtcct gcaactttat    3780
ccgcctccat ccagtctatt aattgttgcc gggaagctag agtaagtagt tcgccagtta    3840
atagtttgcg caacgttgtt gccattgcta caggcatcgt ggtgtcacgc tcgtcgtttg    3900
gtatggcttc attcagctcc ggttcccaac gatcaaggcg agttacatga tcccccatgt    3960
tgtgcaaaaa agcggttagc tccttcggtc ctccgatcgt tgtcagaagt aagttggccg    4020
cagtgttatc actcatggtt atggcagcac tgcataattc tcttactgtc atgccatccg    4080
taagatgctt ttctgtgact ggtgagtact caaccaagtc attctgagaa tagtgtatgc    4140
ggcgaccgag ttgctcttgc ccggcgtcaa tacgggataa taccgcgcca catagcagaa    4200
ctttaaaagt gctcatcatt ggaaaacgtt cttcggggcg aaaactctca aggatcttac    4260
cgctgttgag atccagttcg atgtaaccca ctcgtgcacc caactgatct tcagcatctt    4320
ttactttcac cagcgtttct gggtgagcaa aaacaggaag gcaaaatgcc gcaaaaaagg    4380
gaataagggc gacacggaaa tgttgaatac tcatactctt cctttttcaa tattattgaa    4440
gcatttatca gggttattgt ctcatgagcg gatacatatt tgaatgtatt tagaaaaata    4500
aacaaatagg ggttccgcgc acatttcccc gaaaagtgcc ac                       4542
```

```
<210> SEQ ID NO 7
<211> LENGTH: 10428
<212> TYPE: DNA
<213> ORGANISM: Artificial sequence
<220> FEATURE:
<223> OTHER INFORMATION: SpCas9-2A-GFP vector V1.A.8

<400> SEQUENCE: 7
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
```

-continued

```
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgccaccat ggactataag gaccacgacg agactacaa     960 ggatcatgat attgattaca aagacgatga cgataagatg cccccaaaga agaagcggaa    1020
ggtcggtatc cacggagtcc cagcagccga caagaagtac agcatcggcc tggacatcgg    1080
caccaactct gtgggctggg ccgtgatcac cgacgagtac aaggtgccca gcaagaaatt    1140
caaggtgctg ggcaacaccg accggcacag catcaagaag aacctgatcg gagccctgct    1200
gttcgacagc ggcgaaacag ccgaggccac ccggctgaag agaaccgcca gaagaagata    1260
caccagacgg aagaaccgga tctgctatct gcaagagatc ttcagcaacg agatggccaa    1320
ggtggacgac agcttcttcc acagactgga agagtccttc ctggtggaag aggataagaa    1380
gcacgagcgg cacccatct tcggcaacat cgtggacgag gtggcctacc acgagaagta    1440
ccccaccatc taccacctga aaagaaact ggtggacagc accgacaagg ccgacctgcg    1500
gctgatctat ctggccctgg cccacatgat caagttccgg ggccacttcc tgatcgaggg    1560
cgacctgaac cccgacaaca gcgacgtgga caagctgttc atccagctgg tgcagaccta    1620
caaccagctg ttcgaggaaa acccccatcaa cgccagcggc gtggacgcca aggccatcct    1680
gtctgccaga ctgagcaaga gcagacggct ggaaaatctg atcgcccagc tgcccggcga    1740
gaagaagaat ggcctgttcg aaaacctgat tgccctgagc ctgggcctga ccccccaactt    1800 caagagcaac ttcgacctgg ccgaggatgc caaactgcag ctgagcaagg acacctacga    1860
cgacgacctg gacaacctgc tggcccagat cggcgaccag tacgccgacc tgtttctggc    1920
cgccaagaac ctgtccgacg ccatcctgct gagcgacatc ctgagagtga acaccgagat    1980
caccaaggcc cccctgagcg cctctatgat caagagatac gacgagcacc accaggacct    2040
gaccctgctg aaagctctcg tgcggcagca gctgcctgag aagtacaaag agattttctt    2100
cgaccagagc aagaacggct acgccggcta cattgacggc ggagccagcc aggaagagtt    2160
ctacaagttc atcaagccca tcctggaaaa gatggacggc accgaggaac tgctcgtgaa    2220
gctgaacaga gaggacctgc tgcggaagca gcggaccttc gacaacggca gcatccccca    2280
ccagatccac ctgggagagc tgcacgccat tctgcggcgg caggaagatt ttacccatt     2340 cctgaaggac aaccgggaaa agatcgagaa gatcctgacc ttccgcatcc cctactacgt    2400
gggccctctg gccaggggaa acagcagatt cgcctggatg accagaaaga gcgaggaaac    2460
catcaccccc tggaacttcg aggaagtggt ggacaagggc gcttccgccc agagcttcat    2520
cgagcggatg accaacttcg ataagaacct gcccaacgag aaggtgctgc caagcacag     2580 cctgctgtac gagtacttca ccgtgtataa cgagctgacc aaagtgaaat acgtgaccga    2640
gggaatgaga aagcccgcct tcctgagcgg cgagcagaaa aaggccatcg tggacctgct    2700
```

-continued

```
gttcaagacc aaccggaaag tgaccgtgaa gcagctgaaa gaggactact tcaagaaaat    2760
cgagtgcttc gactccgtgg aaatctccgg cgtggaagat cggttcaacg cctccctggg    2820
cacataccac gatctgctga aaattatcaa ggacaaggac ttcctggaca atgaggaaaa    2880
cgaggacatt ctggaagata tcgtgctgac cctgacactg tttgaggaca gagagatgat    2940
cgaggaacgg ctgaaaacct atgcccacct gttcgacgac aaagtgatga agcagctgaa    3000
gcggcggaga tacaccggct ggggcaggct gagccggaag ctgatcaacg gcatccggga    3060
caagcagtcc ggcaagacaa tcctggattt cctgaagtcc gacggcttcg ccaacagaaa    3120
cttcatgcag ctgatccacg acgacagcct gacctttaaa gaggacatcc agaaagccca    3180
ggtgtccggc cagggcgata gcctgcacga gcacattgcc aatctggccg gcagccccgc    3240
cattaagaag ggcatcctgc agacagtgaa ggtggtggac gagctcgtga agtgatgggg    3300
ccggcacaag cccgagaaca tcgtgatcga aatggccaga gagaaccaga ccacccagaa    3360
gggacagaag aacagccgcg agagaatgaa gcggatcgaa gagggcatca agagctgggg    3420
cagccagatc ctgaaagaac accccgtgga aaacacccag ctgcagaacg agaagctgta    3480
cctgtactac ctgcagaatg ggcgggatat gtacgtggac caggaactgg acatcaaccg    3540
gctgtccgac tacgatgtgg accatatcgt gcctcagagc tttctgaagg acgactccat    3600
cgacaacaag gtgctgacca gaagcgacaa gaaccggggc aagagcgaca cgtgccctc    3660 cgaagaggtc gtgaagaaga tgaagaacta ctggcggcag ctgctgaacg ccaagctgat    3720
tacccagaga aagttcgaca atctgaccaa ggccgagaga ggcggcctga gcgaactgga    3780
taaggccggc ttcatcaaga gacagctggt ggaaacccgg cagatcacaa agcacgtggc    3840
acagatcctg gactcccgga tgaacactaa gtacgacgag aatgacaagc tgatccggga    3900
agtgaaagtg atcaccctga gtccaagct ggtgtccgat ttccggaagg atttccagtt    3960
ttacaaagtg cgcgagatca caactacca ccacgcccac gacgcctacc tgaacgccgt    4020
cgtgggaacc gccctgatca aaaagtaccc taagctggaa agcgagttcg tgtacggcga    4080
ctacaaggtg tacgacgtgc ggaagatgat cgccaagagc gagcaggaaa tcggcaaggc    4140
taccgccaag tacttcttct acagcaacat catgaacttt ttcaagaccg agattaccct    4200
ggccaacggc gagatccgga agcggcctct gatcgagaca aacggcgaaa ccggggagat    4260
cgtgtgggat aagggccggg attttgccac cgtgcgaaaa gtgctgagca tgccccaagt    4320
gaatatcgtg aaaaagaccg aggtgcagac aggcggcttc agcaaagagt ctatcctgcc    4380
caagaggaac agcgataagc tgatcgccag aaagaaggac tgggaccta agaagtacgg    4440 cggcttcgac agccccaccg tggcctattc tgtgctggtg gtggccaaag tggaaaaggg    4500
caagtccaag aaactgaaga gtgtgaaaga gctgctgggg atcaccatca tggaaagaag    4560
cagcttcgag aagaatccca tcgactttct ggaagccaag ggctacaaag aagtgaaaaa    4620
ggacctgatc atcaagctgc ctaagtactc cctgttcgag ctggaaaacg ccggaagag    4680 aatgctggcc tctgccggcg aactgcagaa gggaaacgaa ctggccctgc cctccaaata    4740
tgtgaacttc ctgtacctgg ccagccacta tgagaagctg aagggctccc ccgaggataa    4800
tgagcagaaa cagctgtttg tggaacagca caagcactac ctggacgaga tcatcgagca    4860
gatcagcgag ttctccaaga gagtgatcct ggccgacgct aatctggaca aagtgctgtc    4920
cgcctacaac aagcaccggg ataagcccat cagagagcag gccgagaata tcatccacct    4980
gtttaccctg accaatctgg gagcccctgc cgccttcaag tactttgaca ccaccatcga    5040
ccggaagagg tacaccagca ccaaagaggt gctggacgcc accctgatcc accagagcat    5100
```

-continued

```
caccggcctg tacgagacac ggatcgacct gtctcagctg ggaggcgaca aaaggccggc   5160
ggccacgaaa aaggccggcc aggcaaaaaa gaaaaaggaa ttcggcagtg gagagggcag   5220
aggaagtctg ctaacatgcg gtgacgtcga ggagaatcct ggcccagtga gcaagggcga   5280
ggagctgttc accggggtgg tgcccatcct ggtcgagctg gacggcgacg taaacggcca   5340
caagttcagc gtgtccggcg agggcgaggg cgatgccacc tacggcaagc tgaccctgaa   5400
gttcatctgc accaccggca agctgcccgt gcccctggcc accctcgtga ccaccctgac   5460
ctacggcgtg cagtgcttca gccgctaccc cgaccacatg aagcagcacg acttcttcaa   5520
gtccgccatg cccgaaggct acgtccagga gcgcaccatc ttcttcaagg acgacggcaa   5580
ctacaagacc cgcgccgagg tgaagttcga gggcgacacc ctggtgaacc gcatcgagct   5640
gaagggcatc gacttcaagg aggacggcaa catcctgggg cacaagctgg agtacaacta   5700
caacagccac aacgtctata tcatggccga caagcagaag aacggcatca aggtgaactt   5760
caagatccgc cacaacatcg aggacggcag cgtgcagctc gccgaccact accagcagaa   5820 caccccccatc ggcgacggcc ccgtgctgct gcccgacaac cactacctga gcacccagtc   5880
cgccctgagc aaagacccca acgagaagcg cgatcacatg gtcctgctgg agttcgtgac   5940
cgccgccggg atcactctcg gcatggacga gctgtacaag gaattctaac gctagagggc   6000
ccgtttaaac ccgctgatca gcctcgactg tgccttctag ttgccagcca tctgttgttt   6060
gcccctcccc cgtgccttcc ttgaccctgg aaggtgccac tcccactgtc ctttcctaat   6120
aaaatgagga aattgcatcg cattgtctga gtaggtgtca ttctattctg gggggtgggg   6180
tggggcagga cagcaagggg gaggattggg aagacaatag caggcatgct ggggatgcgg   6240
tgggctctat ggcttctgag gcggaaagaa ccagctgggg ctctaggggg tatccccacg   6300
cgccctgtag cggcgcatta agcgcggcgg gtgtggtggt tacgcgcagc gtgaccgcta   6360
cacttgccag cgccctagcg cccgctcctt tcgctttctt cccttccttt ctcgccacgt   6420
tcgccggctt tccccgtcaa gctctaaatc ggggggctccc tttagggttc cgatttagtg   6480
ctttacggca cctcgacccc aaaaaacttg attagggtga tggttcacgt agtgggccat   6540
cgccctgata gacggttttt cgccctttga cgttggagtc cacgttcttt aatagtggac   6600
tcttgttcca aactggaaca acactcaacc ctatctcggt ctattctttt gatttataag   6660
ggattttgcc gatttcggcc tattggttaa aaaatgagct gatttaacaa aaatttaacg   6720
cgaattaatt ctgtggaatg tgtgtcagtt agggtgtgga aagtccccag gctccccagc   6780
aggcagaagt atgcaaagca tgcatctcaa ttagtcagca accaggtgtg gaaagtcccc   6840
aggctcccca gcaggcagaa gtatgcaaag catgcatctc aattagtcag caaccatagt   6900
cccgccccta actccgccca tcccgcccct aactccgccc agttccgccc attctccgcc   6960
ccatggctga ctaatttttt ttatttatgc agaggccgag gccgcctctg cctctgagct   7020
attccagaag tagtgaggag gcttttttgg aggcctaggc ttttgcaaaa agctcccggg   7080
agcttgtata tccattttcg gatctgatca agagacagga tgaggatcgt ttcgcatgat   7140
tgaacaagat ggattgcacg caggttctcc ggccgcttgg gtggagaggc tattcggcta   7200
tgactgggca caacagacaa tcggctgctc tgatgccgcc gtgttccggc tgtcagcgca   7260
ggggcgcccg gttcttttg tcaagaccga cctgtccggt gccctgaatg aactgcagga   7320
cgaggcagcg cggctatcgt ggctggccac gacgggcgtt ccttgcgcag ctgtgctcga   7380
cgttgtcact gaagcgggaa gggactggct gctattgggc gaagtgccgg ggcaggatct   7440
```

```
cctgtcatct caccttgctc ctgccgagaa agtatccatc atggctgatg caatgcggcg    7500
gctgcatacg cttgatccgg ctacctgccc attcgaccac caagcgaaac atcgcatcga    7560
gcgagcacgt actcggatgg aagccggtct tgtcgatcag gatgatctgg acgaagagca    7620
tcaggggctc gcgccagccg aactgttcgc caggctcaag gcgcgcatgc ccgacgcgcga   7680 ggatctcgtc gtgacccatg gcgatgcctg cttgccgaat atcatggtgg aaaatggccg    7740
cttttctgga ttcatcgact gtggccggct gggtgtggcg gaccgctatc aggacatagc    7800
gttggctacc cgtgatattg ctgaagagct tggcggcgaa tgggctgacc gcttcctcgt    7860
gctttacggt atcgccgctc ccgattcgca gcgcatcgcc ttctatcgcc ttcttgacga    7920
gttcttctga gcgggactct ggggttcgaa atgaccgacc aagcgacgcc caacctgcca    7980
tcacgagatt tcgattccac cgccgccttc tatgaaaggt tgggcttcgg aatcgttttc    8040
cgggacgccg gctggatgat cctccagcgc ggggatctca tgctggagtt cttcgcccac    8100
cccaacttgt ttattgcagc ttataatggt tacaaataaa gcaatagcat cacaaatttc    8160
acaaataaag catttttttc actgcattct agttgtggtt tgtccaaact catcaatgta    8220
tcttatcatg tctgtatacc gtcgacctct agctagagct tggcgtaatc atggtcatag    8280
ctgtttcctg tgtgaaattg ttatccgctc acaattccac acaacatacg agccggaagc    8340
ataaagtgta aagcctgggg tgcctaatga gtgagctaac tcacattaat tgcgttgcgc    8400
tcactgcccg ctttccagtc gggaaacctg tcgtgccagc tgcattaatg aatcggccaa    8460
cgcgcgggga gaggcggttt gcgtattggg cgctcttccg cttcctcgct cactgactcg    8520
ctgcgctcgg tcgttcggct gcggcgagcg gtatcagctc actcaaaggc ggtaatacgg    8580
ttatccacag aatcagggga taacgcagga agaacatgt gagcaaaagg ccagcaaaag    8640
gccaggaacc gtaaaaaggc cgcgttgctg gcgtttttcc ataggctccg ccccctgac     8700 gagcatcaca aaaatcgacg ctcaagtcag aggtggcgaa acccgacagg actataaaga    8760
taccaggcgt ttcccctgg aagctccte gtgcgctctc ctgttccgac cctgccgctt     8820
accggatacc tgtccgcctt tctcccttcg ggaagcgtgg cgctttctca tagctcacgc    8880
tgtaggtatc tcagttcggt gtaggtcgtt cgctccaagc tgggctgtgt gcacgaaccc    8940
cccgttcagc ccgaccgctg cgccttatcc ggtaactatc gtcttgagtc caacccggta    9000
agacacgact tatcgccact ggcagcagcc actggtaaca ggattagcag agcgaggtat    9060
gtaggcggtg ctacagagtt cttgaagtgg tggcctaact acggctacac tagaagaaca    9120
gtatttggta tctgcgctct gctgaagcca gttaccttcg gaaaaagagt tggtagctct    9180
tgatccggca aacaaaccac cgctggtagc ggtttttttg tttgcaagca gcagattacg    9240
cgcagaaaaa aaggatctca agaagatcct ttgatctttt ctacggggtc tgacgctcag    9300
tggaacgaaa actcacgtta agggattttg gtcatgagat tatcaaaaag gatcttcacc    9360
tagatccttt taaattaaaa atgaagtttt aaatcaatct aaagtatata tgagtaaact    9420
tggtctgaca gttaccaatg cttaatcagt gaggcaccta tctcagcgat ctgtctattt    9480
cgttcatcca tagttgcctg actccccgtc gtgtagataa ctacgatacg ggagggctta    9540
ccatctggcc ccagtgctgc aatgataccg cgagacccac gctcaccggc tccagattta    9600
tcagcaataa accagccagc cggaagggcc gagcgcagaa gtggtcctgc aactttatcc    9660
gcctccatcc agtctattaa ttgttgccgg gaagctagag taagtagttc gccagttaat    9720
agtttgcgca acgttgttgc cattgctaca ggcatcgtgg tgtcacgctc gtcgtttggt    9780
atggcttcat tcagctccgg ttcccaacga tcaaggcgag ttacatgatc ccccatgttg    9840
```

-continued

```
tgcaaaaaag cggttagctc cttcggtcct ccgatcgttg tcagaagtaa gttggccgca      9900
gtgttatcac tcatggttat ggcagcactg cataattctc ttactgtcat gccatccgta      9960
agatgctttt ctgtgactgg tgagtactca accaagtcat tctgagaata gtgtatgcgg    10020
cgaccgagtt gctcttgccc ggcgtcaata cgggataata ccgcgccaca tagcagaact    10080
ttaaaagtgc tcatcattgg aaaacgttct cggggcgaaa actctcaag gatcttaccg      10140 ctgttgagat ccagttcgat gtaacccact cgtgcaccca actgatcttc agcatctttt    10200
actttcacca gcgtttctgg gtgagcaaaa acaggaaggc aaaatgccgc aaaaaaggga    10260
ataagggcga cacggaaatg ttgaatactc atactcttcc tttttcaata ttattgaagc    10320
atttatcagg gttattgtct catgagcgga tacatatttg aatgtattta gaaaaataaa    10380 caaataggg ttccgcgcac atttccccga aaagtgccac ctgacgtc              10428
```

```
<210> SEQ ID NO 8
<211> LENGTH: 6071
<212> TYPE: DNA
<213> ORGANISM: Artificial sequence
<220> FEATURE:
<223> OTHER INFORMATION: pcDNA3.1_GFP vector V1.A.4

<400> SEQUENCE: 8
```

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta caactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaactt aagcttggta ccgccaccat ggaatccgat gagtctggcc tgcccgccat      960
ggaaatcgag tgcagaatca ccggcaccct gaacggcgtg aatttgagc tcgtgggcgg    1020 aggcgaggga cacctgaac agggcagaat gaccaacaag atgaagtcca ccaagggggc    1080
cctgaccttc agcccctacc tgctgtctca cgtgatgggc tacggcttct accacttcgg    1140
cacctacccc agcggctacg agaaccctt cctgcacgcc atcaacaacg gcggctacac    1200
caacacccgg atcgagaagt acgaggacgg cggcgtgctg cacgtgtcct tcagctacag    1260
atacgaggcc ggcagagtga tcggcgactt caaagtgatg ggcaccggat ccccgagga    1320 cagcgtgatc ttcaccgaca agatcatccg gtccaacgcc accgtggaac atctgcaccc    1380
catgggcgac aacgacctgg acggcagctt caccagaacc ttctctcctgc gggatggcgg    1440
```

-continued

```
ctactacagc agcgtggtgg acagccacat gcacttcaag agcgccatcc accccagcat   1500
cctccagaac ggcggaccca tgttcgcctt cagacgggtg gaagaggacc acagcaacac   1560
cgagctgggc atcgtggaat accagcacgc cttcaagacc cccgatgccg atgccggcga   1620
ggaatgagtc gagtctagag ggcccgttta aacccgctga tcagcctcga ctgtgccttc   1680
tagttgccag ccatctgttg tttgcccctc ccccgtgcct tccttgaccc tggaaggtgc   1740
cactcccact gtcctttcct aataaaatga ggaaattgca tcgcattgtc tgagtaggtg   1800
tcattctatt ctggggggtg gggtggggca ggacagcaag ggggaggatt gggaagacaa   1860
tagcaggcat gctggggatg cggtgggctc tatggcttct gaggcggaaa gaaccagctg   1920
gggctctagg gggtatcccc acgcgccctg tagcggcgca ttaagcgcgg cgggtgtggt   1980
ggttacgcgc agcgtgaccg ctacacttgc cagcgcccta cgcccgctc ctttcgcttt   2040 cttcccttcc tttctcgcca cgttcgccgg ctttccccgt caagctctaa atcgggggct   2100
ccctttaggg ttccgattta gtgctttacg gcacctcgac cccaaaaaac ttgattaggg   2160
tgatggttca cgtagtgggc catcgccctg atagacggtt tttcgccctt tgacgttgga   2220
gtccacgttc tttaatagtg gactcttgtt ccaaactgga acaacactca accctatctc   2280
ggtctattct tttgatttat aagggatttt gccgatttcg gcctattggt taaaaaatga   2340
gctgatttaa caaaaattta cgcgaatta attctgtgga atgtgtgtca gttagggtgt   2400
ggaaagtccc caggctcccc agcaggcaga agtatgcaaa gcatgcatct caattagtca   2460
gcaaccaggt gtggaaagtc cccaggctcc ccagcaggca gaagtatgca aagcatgcat   2520
ctcaattagt cagcaaccat agtcccgccc ctaactccgc ccatcccgcc cctaactccg   2580
cccagttccg cccattctcc gccccatggc tgactaattt tttttattta tgcagaggcc   2640
gaggccgcct ctgcctctga gctattccag aagtagtgag gaggcttttt tggaggccta   2700
ggcttttgca aaaagctccc gggagcttgt atatccattt tcggatctga tcaagagaca   2760
ggatgaggat cgtttcgcat gattgaacaa gatggattgc acgcaggttc tccggccgct   2820
tgggtggaga ggctattcgg ctatgactgg gcacaacaga caatcggctg ctctgatgcc   2880
gccgtgttcc ggctgtcagc gcaggggcgc ccggttcttt ttgtcaagac cgacctgtcc   2940
ggtgccctga atgaactgca ggacgaggca gcgcggctat cgtggctggc cacgacgggc   3000
gttccttgcg cagctgtgct cgacgttgtc actgaagcgg gaagggactg gctgctattg   3060
ggcgaagtgc cggggcagga tctcctgtca tctcaccttg ctcctgccga gaaagtatcc   3120
atcatggctg atgcaatgcg gcggctgcat acgcttgatc cggctacctg cccattcgac   3180
caccaagcga aacatcgcat cgagcgagca cgtactcgga tggaagccgg tcttgtcgat   3240
caggatgatc tggacgaaga gcatcagggg ctcgcgccag ccgaactgtt cgccaggctc   3300
aaggcgcgca tgcccgacgg cgaggatctc gtcgtgaccc atggcgatgc ctgcttgccg   3360
aatatcatgg tggaaaatgg ccgcttttct ggattcatcg actgtggccg ctgggtgtg   3420 gcggaccgct atcaggacat agcgttggct acccgtgata ttgctgaaga gcttggcggc   3480
gaatgggctg accgcttcct cgtgctttac ggtatcgccg ctcccgattc gcagcgcatc   3540
gccttctatc gccttcttga cgagttcttc tgagcgggac tctggggttc gaaatgaccg   3600
accaagcgac gcccaacctg ccatcacgag atttcgattc caccgccgcc ttctatgaaa   3660
ggttgggctt cggaatcgtt ttccgggacg ccggctggat gatcctccag cgcggggatc   3720
tcatgctgga gttcttcgcc cacccaact tgtttattgc agcttataat ggttacaaat   3780
aaagcaatag catcacaaat ttcacaaata aagcattttt ttcactgcat ctagttgtg   3840
```

```
gtttgtccaa actcatcaat gtatcttatc atgtctgtat accgtcgacc tctagctaga    3900
gcttggcgta atcatggtca tagctgtttc ctgtgtgaaa ttgttatccg ctcacaattc    3960
cacacaacat acgagccgga agcataaagt gtaaagcctg gggtgcctaa tgagtgagct    4020
aactcacatt aattgcgttg cgctcactgc ccgctttcca gtcgggaaac ctgtcgtgcc    4080
agctgcatta atgaatcggc caacgcgcgg ggagaggcgg tttgcgtatt gggcgctctt    4140
ccgcttcctc gctcactgac tcgctgcgct cggtcgttcg ctgcggcga gcggtatcag    4200 ctcactcaaa ggcggtaata cggttatcca cagaatcagg ggataacgca ggaaagaaca    4260
tgtgagcaaa aggccagcaa aaggccagga accgtaaaaa ggccgcgttg ctggcgtttt    4320
tccataggct ccgcccccct gacgagcatc acaaaaatcg acgctcaagt cagaggtggc    4380
gaaacccgac aggactataa agataccagg cgtttccccc tggaagctcc ctcgtgcgct    4440
ctcctgttcc gaccctgccg cttaccggat acctgtccgc ctttctccct cgggaagcg    4500 tggcgctttc tcatagctca cgctgtaggt atctcagttc ggtgtaggtc gttcgctcca    4560
agctgggctg tgtgcacgaa ccccccgttc agcccgaccg ctgcgcctta tccggtaact    4620
atcgtcttga gtccaacccg gtaagacacg acttatcgcc actggcagca gccactggta    4680
acaggattag cagagcgagg tatgtaggcg gtgctacaga gttcttgaag tggtggccta    4740
actacggcta cactagaaga acagtatttg gtatctgcgc tctgctgaag ccagttacct    4800
tcggaaaaag agttggtagc tcttgatccg gcaaacaaac caccgctggt agcggttttt    4860
ttgtttgcaa gcagcagatt acgcgcagaa aaaaaggatc tcaagaagat cctttgatct    4920
tttctacggg gtctgacgct cagtggaacg aaaactcacg ttaagggatt ttggtcatga    4980
gattatcaaa aaggatcttc acctagatcc ttttaaatta aaaatgaagt tttaaatcaa    5040
tctaaagtat atatgagtaa acttggtctg acagttacca atgcttaatc agtgaggcac    5100
ctatctcagc gatctgtcta tttcgttcat ccatagttgc ctgactcccc gtcgtgtaga    5160
taactacgat acgggagggc ttaccatctg gccccagtgc tgcaatgata ccgcgagacc    5220
cacgctcacc ggctccagat ttatcagcaa taaaccagcc agccggaagg ccgagcgca    5280 gaagtggtcc tgcaacttta tccgcctcca tccagtctat taattgttgc cgggaagcta    5340
gagtaagtag ttcgccagtt aatagtttgc gcaacgttgt tgccattgct acaggcatcg    5400
tggtgtcacg ctcgtcgttt ggtatggctt cattcagctc cggttcccaa cgatcaaggc    5460
gagttacatg atcccccatg ttgtgcaaaa aagcggttag ctccttcggt cctccgatcg    5520
ttgtcagaag taagttggcc gcagtgttat cactcatggt tatggcagca ctgcataatt    5580
ctcttactgt catgccatcc gtaagatgct tttctgtgac tggtgagtac tcaaccaagt    5640
cattctgaga atagtgtatg cggcgaccga gttgctcttg cccggcgtca atacgggata    5700
ataccgcgcc acatagcaga actttaaaag tgctcatcat tggaaaacgt tcttcggggc    5760
gaaaactctc aaggatctta ccgctgttga atccagttc gatgtaaccc actcgtgcac    5820
ccaactgatc ttcagcatct tttactttca ccagcgtttc tgggtgagca aaaacaggaa    5880
ggcaaaatgc cgcaaaaaag ggaataaggg cgacacggaa atgttgaata ctcatactct    5940
tcctttttca atattattga agcatttatc agggttattg tctcatgagc ggatacatat    6000
ttgaatgtat ttagaaaaat aaacaaatag gggttccgcg cacatttccc cgaaaagtgc    6060
cacctgacgt c                                                         6071
```

<210> SEQ ID NO 9

```
<211> LENGTH: 2762
<212> TYPE: DNA
<213> ORGANISM: Artificial sequence
<220> FEATURE:
<223> OTHER INFORMATION: AAVSI_sg-sp-opti_3 vector V2.J.6

<400> SEQUENCE: 9
ctaaattgta agcgttaata ttttgttaaa attcgcgtta aattttttgtt aaatcagctc        60 attttttaac caataggccg aaatcggcaa aatcccttat aaatcaaaag aatagaccga       120
gatagggttg agtggccgct acagggcgct cccattcgcc attcaggctg cgcaactgtt       180
gggaagggcg tttcggtgcg ggcctcttcg ctattacgcc agctggcgaa aggggggatgt      240 gctgcaaggc gattaagttg ggtaacgcca gggtttttccc agtcacgacg ttgtaaaacg       300
acggccagtg agcgcgacgt aatacgactc actatagggc gaattggcgg aaggccgtca       360
aggccgcatg gatccaaggt cgggcaggaa gagggcctat ttcccatgat tccttcatat       420
ttgcatatac gatacaaggc tgttagagag ataattagaa ttaatttgac tgtaaacaca       480
aagatattag tacaaaatac gtgacgtaga aagtaataat ttcttgggta gtttgcagtt       540
ttaaaattat gttttaaaat ggactatcat atgcttaccg taacttgaaa gtatttcgat       600
ttcttggctt tatatatctt gtggaaagga cgaaacaccg tcaccaatcc tgtccctagg       660
tttaagagct atgctggaaa cagcatagca agtttaaata aggctagtcc gttatcaact       720
tgaaaaagtg gcaccgagtc ggtgcttttt ttcagacatc catagatcta gctcgagttt       780
tttttctaga ctgggcctca tgggccttcc gctcactgcc cgctttccag tcgggaaacc       840
tgtcgtgcca gctgcattaa catggtcata gctgttcct tgcgtattgg gcgctctccg        900
cttcctcgct cactgactcg ctgcgctcgg tcgttcgggt aaagcctggg gtgcctaatg       960
agcaaaaggc cagcaaaagg ccaggaaccg taaaaaggcc gcgttgctgg cgtttttcca      1020
taggctccgc ccccctgacg agcatcacaa aaatcgacgc tcaagtcaga ggtggcgaaa      1080
cccgacagga ctataaagat accaggcgtt tccccctgga agctccctcg tgcgctctcc      1140
tgttccgacc ctgccgctta ccggatacct gtccgccttt ctcccttcgg gaagcgtggc      1200
gctttctcat agctcacgct gtaggtatct cagttcggtg taggtcgttc gctccaagct      1260
gggctgtgtg cacgaacccc ccgttcagcc cgaccgctgc gccttatccg gtaactatcg      1320
tcttgagtcc aacccggtaa gacacgactt atcgccactg gcagcagcca ctggtaacag      1380
gattagcaga gcgaggtatg taggcggtgc tacagagttc ttgaagtggt ggcctaacta      1440
cggctacact agaagaacag tatttggtat ctgcgctctg ctgaagccag ttaccttcgg      1500
aaaaagagtt ggtagctctt gatccggcaa acaaaccacc gctggtagcg gtggtttttt      1560
tgtttgcaag cagcagatta cgcgcagaaa aaaaggatct caagaagatc ctttgatctt      1620
ttctacgggg tctgacgctc agtggaacga aaactcacgt taagggattt tggtcatgag      1680
attatcaaaa aggatcttca cctagatcct tttaaattaa aaatgaagtt ttaaatcaat      1740
ctaaagtata tatgagtaaa cttggtctga cagttaccaa tgcttaatca gtgaggcacc      1800
tatctcagcg atctgtctat ttcgttcatc catagttgcc tgactccccg tcgtgtagat      1860
aactacgata cgggagggct taccatctgg ccccagtgct gcaatgatac cgcgagaacc      1920
acgctcaccg gctccagatt tatcagcaat aaaccagcca gccggaaggg ccgagcgcag      1980
aagtggtcct gcaactttat ccgcctccat ccagtctatt aattgttgcc gggaagctag      2040
agtaagtagt tcgccagtta atagtttgcg caacgttgtt gccattgcta caggcatcgt      2100
ggtgtcacgc tcgtcgtttg gtatggcttc attcagctcc ggttcccaac gatcaaggcg      2160
```

-continued

```
agttacatga tcccccatgt tgtgcaaaaa agcggttagc tccttcggtc ctccgatcgt      2220
tgtcagaagt aagttggccg cagtgttatc actcatggtt atggcagcac tgcataattc      2280
tcttactgtc atgccatccg taagatgctt ttctgtgact ggtgagtact caaccaagtc      2340
attctgagaa tagtgtatgc ggcgaccgag ttgctcttgc ccggcgtcaa tacgggataa      2400
taccgcgcca catagcagaa ctttaaaagt gctcatcatt ggaaaacgtt cttcggggcg      2460
aaaactctca aggatcttac cgctgttgag atccagttcg atgtaaccca ctcgtgcacc      2520
caactgatct tcagcatctt ttactttcac cagcgtttct gggtgagcaa aaacaggaag      2580
gcaaaatgcc gcaaaaaagg gaataagggc gacacgaaaa tgttgaatac tcatactctt      2640 ccttttcaa tattattgaa gcatttatca gggttattgt ctcatgagcg gatacatatt       2700
tgaatgtatt tagaaaaata aacaaatagg ggttccgcgc acatttcccc gaaaagtgcc       2760
ac                                                                      2762
```

<210> SEQ ID NO 10
<211> LENGTH: 8188
<212> TYPE: DNA
<213> ORGANISM: Artificial sequence
<220> FEATURE:
<223> OTHER INFORMATION: AAVS-EF1aL-TxnCS-S-STv5a_G-in:FRT:MYC-RFP:F3-
      EF1a V9.F.5

<400> SEQUENCE: 10

```
gagctctact ggcttctgcg ccgcctctgg cccactgttt ccccttccca ggcaggtcct        60
gctttctctg acctgcattc tctcccctgg cctgtgccg ctttctgtct gcagcttgtg        120
gcctgggtca cctctacggc tggcccagat ccttccctgc cgcctccttc aggttccgtc        180
ttcctccact ccctcttccc cttgctctct gctgtgttgc tgcccaagga tgctctttcc       240
ggagcacttc cttctcggcg ctgcaccacg tgatgtcctc tgagcggatc ctccccgtgt       300
ctgggtcctc tccgggcatc tctcctccct cacccaaccc catgccgtct tcactcgctg       360
ggttcccttt tccttctcct tctggggcct gtgccatctc tcgtttctta ggatggcctt       420
ctccgacgga tgtctccctt gcgtcccgcc tccccttctt gtaggcctgc atcatcaccg       480
tttttctgga caaccccaaa gtaccccgtc tccctggctt tagccacctc tccatcctct       540
tgctttcttt gcctggacac cccgttctcc tgtggattcg ggtcacctct cactcctttc       600
atttgggcag ctcccctacc cccttacct ctctagtctg tgctagctct tccagccccc        660
tgtcatggca tcttccaggg gtccgagagc tcagctagtc ttcttcctcc aacccgggcc       720
cctatgtcca cttcaggaca gcatgtttgc tgcctccagg gatcctgtgt ccccgagctg       780
ggaccacctt atattcccag ggccggttaa tgtggctctg gttctgggta cttttatctg       840
tcccctccac cgggtggctc cggtgcccgt cagtgggcag agcgcacatc gcccacagtc       900
cccgagaagt tggggggagg ggtcggcaat tgaaccggtg cctagagaag gtggcgcggg       960
gtaaactggg aaagtgatgt cgtgtactgg ctccgccttt ttcccgaggg tggggggagaa     1020 ccgtatataa gtgcagtagt cgccgtgaac gttcttttc gcaacgggtt tgccgccaga       1080
acacaggtaa gtgccgtgtg tggttcccgc gggcctggcc tctttacggg ttatggccct      1140
tgcgtgcctt gaattacttc cactggctgc agtacgtgat tcttgatccc gagcttcggg      1200
ttggaagtgg gtgggagagt tcgaggcctt gcgcttaagg agccccttcg cctcgtgctt      1260
gagttgaggc ctggcctggg cgctgggccc gccgcgtgcg aatctggtgg caccttcgcg      1320
cctgtctcgc tgctttcgat aagtctctag ccatttaaaa tttttgatga cctgctgcga     1380
```

```
cgcttttttt ctggcaagat agtcttgtaa atgcgggcca agatctgcac actggtattt      1440
cggtttttgg ggccgcgggc ggcgacgggg cccgtgcgtc ccagcgcaca tgttcggcga      1500 ggcgggcct gcgagcgcgg ccaccgagaa tcggacgggg gtagtctcaa gctggccggc        1560
ctgctctggt gcctggcctc gcgccgccgt gtatcgcccc gccctgggcg gcaaggctgg      1620
cccggtcggc accagttgcg tgagcggaaa gatggccgct tcccggccct gctgcaggga      1680
gctcaaaatg gaggacgcgg cgctcgggag agcgggcggg tgagtcaccc acacaaagga      1740
aaagggcctt tccgtcctca gccgtcgctt catgtgactc cacggagtac cgggcgccgt      1800
ccaggcacct cgattagttc tcgagctttt ggagtacgtc gtctttaggt tgggggggagg      1860 ggttttatgc gatggagttt ccccacactg agtgggtgga gactgaagtt aggccagctt      1920
ggcacttgat gtaattctcc ttggaatttg ccctttttga gtttggatct tggttcattc      1980
tcaagcctca gacagtggtt caaagttttt ttcttccatt tcaggtgtcg tgactgctta      2040
agcttggtac cgccaccatg gccaagggct tctacatcag caagagcctg ggcatcctgg      2100
gaatcctgct gggagtggct gctgtgtgca ccatcatcgc tctgagcgtg gtgtacagcc      2160
aggagggagg tcctggatcc ggaacaggtg gctctggcac tggaggatca ggtccaggtg      2220
gatctatggt gaagcagatc gagagcaaga ctgctttcca ggaagccttg gacgctgcag      2280
gtgataagct tgtagtagtt gacttctcag caacgtggtc tggaccttcc aagatgatca      2340
agcctttctt ccattccctc tctgagaagt attccaacgt gatattcctt gaagtagatg      2400
tggatgactc tcaggatgtt gcttcagagt gtgaagtcaa atccatgcca acattccagt      2460
tcttcaagaa gggacagaag gtgggtgaat tttctggagc caataaggag aagcttgaag      2520
ccaccattaa cgagttggta ggtaagtggc tggggccaga gactggctct tgaagttcct      2580
attccgaagt tcctattctc tagaaagtat aggaacttcc tggctcagaa aaagggccct      2640
gacaactctt ttcatcttct aggcggttcc tctacatccg gtggatctgg atctggagaa      2700
caaaagctca tctctgagga ggaccttggg gagcagaagc taatcagtga agaagacctc      2760
ggagagcaga aattgattag cgaggaggat ctttaaagac gctagcacct gatcctgatc      2820
ataatcaagc catatcacat ctgtagaggt ttacttgctt taaaaaacct ccacacctcc      2880
ccctgaacct gaaacataaa atgaatgcaa ttgttgttgt aacttgtttt attgcagctt      2940
ataatggtta caaataaagc aatagcatca caaatttcac aaataaagca ttttttttcac      3000 tgcattctag ttgtggtttg tccaaactca tcaatgtatc ttatcatgtc tggatctgct      3060
gaagagcgct gatcagctct tcaccataga gcccaccgca tccccagcat gcctgctatt      3120
gtcttcccaa tcctccccct tgctgtcctg ccccacccca ccccccagaa tagaatgaca      3180
cctactcaga caatgcgatg caatttcctc attttattag gaaaggacag tgggagtggc      3240
accttccagg gtcaaggaag gcacggggga ggggcaaaca acagatggct ggcaactaga      3300
aggcacagtc gggtgctagc tcatctgtgg cccagcttgc taggcaggtc gcagtacttg      3360
gccacggcca tctcgtgctg ttccacgtag gtttctttgt cggcctcttt gatccgttcc      3420
agccggtggt ccacgaagtg gaagccgggc atcttcaggt tcttggcggg cttcttgctt      3480
ctgtaggtgg tcttgaagga gcagtgcagg tagcctccgc ccacgagttt cagggccatc      3540
tgagaatggc ctctcaggcc gccatcggca gggtacagca tctcggtgtt ggcctcccag      3600
cctctggttt tcttctgcat cacggggccg ttgctgggga agttcacgcc gttaatcttc      3660
acgttgtaga tgatgcagcc gttctggaag ctggtatcct gggtggcggt cagcactccg      3720
```

-continued

```
ccgtcctcgt atgtggtgat ccgctcccag gtgaagccct cggggaagct ctgcttgaag    3780
aaatcgggga tgccctgggt gtggttgatg aaggccttgc tgccgtacat aaagctggtg    3840
gccaggatat caaaggcgaa gggcagaggg ccgccttcca ccaccttgat cttcatggtc    3900
tgggtgccct cgtaaggctt gccctcgccc tcgctggtgc acttgaagtg gtggttgttc    3960
acggtgcctt ccatgtacag cttcatgtgc atgttttctt tgatcagctc gctcatggtg    4020
gctacggaag ttcctattcc gaagttccta ttcttcaaat agtataggaa cttccggtac    4080
cagtcacgac acctgaaatg gaagaaaaaa actttgaacc actgtctgag gcttgagaat    4140
gaaccaagat ccaaactcaa aaagggcaaa ttccaaggag aattacatca agtgccaagc    4200
tggcctaact tcagtctcca cccactcagt gtggggaaac tccatcgcat aaaacccctc    4260
cccccaacct aaagacgacg tactccaaaa gctcgagaac taatcgaggt gcctggacgg    4320
cgcccggtac tccgtggagt cacatgaagc gacggctgag gacggaaagg cccttttcct    4380
ttgtgtgggt gactcacccg cccgctctcc cgagcgccgc gtcctccatt ttgagctccc    4440
tgcagcaggg ccgggaagcg gccatctttc cgctcacgca actggtgccg accgggccag    4500
ccttgccgcc cagggcgggg cgatacacgg cggcgcgagg ccaggcacca gagcaggccg    4560
gccagcttga gactacccccc gtccgattct cggtggccgc gctcgcaggc cccgcctcgc    4620
cgaacatgtg cgctgggacg cacgggcccc gtcgccgccc gcggccccaa aaaccgaaat    4680
accagtgtgc agatcttggc ccgcatttac aagactatct tgccagaaaa aaagcgtcgc    4740
agcaggtcat caaaaatttt aaatggctag agacttatcg aaagcagcga gacaggcgcg    4800
aaggtgccac cagattcgca cgcggcggcc ccagcgccca ggccaggcct caactcaagc    4860
acgaggcgaa ggggctcctt aagcgcaagg cctcgaactc tcccacccac ttccaacccg    4920
aagctcggga tcaagaatca cgtactgcag ccagtggaag taattcaagg cacgcaaggg    4980
ccataacccg taaagaggcc aggcccgcgg gaaccacaca cggcacttac ctgtgttctg    5040
gcggcaaacc cgttgcgaaa aagaacgttc acgcgcgacta ctgcacttat atacggttct    5100
cccccaccct cgggaaaaag gcggagccag tacacgacat cactttccca gtttacccccg    5160 cgccaccttc tctaggcacc ggttcaattg ccgaccccctc ccccccaactt ctcggggact    5220 gtgggcgatg tgcgctctgc ccactgacgg gcaccggagc caccggatca ggatcaggat    5280
tggtgacaga aaagccccat ccttaggcct cctccttcct agtctcctga tattgggtct    5340 aaccccccacc tcctgttagg cagattcctt atctggtgac acaccccccat ttcctggagc    5400 catctctctc cttgccagaa cctctaaggt ttgcttacga tggagccaga gaggatcctg    5460
ggagggagag cttggcaggg ggtgggaggg aagggggga tgcgtgacct gcccggttct    5520
cagtggccac cctgcgctac cctctcccag aacctgagct gctctgacgc ggctgtctgg    5580
tgcgtttcac tgatcctggt gctgcagctt ccttacactt cccaagagga gaagcagttt    5640
ggaaaaacaa aatcagaata agttggtcct gagttctaac tttggctctt cacctttcta    5700
gtccccaatt tatattgttc ctccgtgcgt cagttttacc tgtgagataa ggccagtagc    5760
cagccccgtc ctggcagggc tgtggtgagg aggggggtgt ccgtgtggaa aactccคttt    5820 gtgagaatgg tgcgtcctcg agctgggcct catgggcctt ccgctcactg cccgctttcc    5880
agtcgggaaa cctgtcgtgc cagctgcatt aacatggtca tagctgtttc cttgcgtatt    5940
gggcgctctc cgcttcctcg ctcactgact cgctgcgctc ggtcgttcgg gtaaagcctg    6000
gggtgcctaa tgagcaaaag gccagcaaaa ggccaggaac cgtaaaaagg ccgcgttgct    6060 ggcgttttttc cataggctcc gcccccctga cgagcatcac aaaaatcgac gctcaagtca    6120
```

-continued

```
gaggtggcga aacccgacag gactataaag ataccaggcg tttcccctg gaagctccct    6180 cgtgcgctct cctgttccga ccctgccgct taccggatac ctgtccgcct ttctcccttc    6240
gggaagcgtg gcgctttctc atagctcacg ctgtaggtat ctcagttcgg tgtaggtcgt    6300
tcgctccaag ctgggctgtg tgcacgaacc ccccgttcag cccgaccgct cgccttatc    6360 cggtaactat cgtcttgagt ccaacccggt aagacacgac ttatcgccac tggcagcagc    6420
cactggtaac aggattagca gagcgaggta tgtaggcggt gctacagagt tcttgaagtg    6480
gtggcctaac tacggctaca ctagaagaac agtatttggt atctgcgctc tgctgaagcc    6540
agttaccttc ggaaaaagag ttggtagctc ttgatccggc aaacaaacca ccgctggtag    6600
cggtggtttt tttgtttgca agcagcagat tacgcgcaga aaaaaggat ctcaagaaga    6660 tcctttgatc ttttctacgg ggtctgacgc tcagtggaac gaaaactcac gttaagggat    6720
tttggtcatg agattatcaa aaaggatctt cacctagatc ctttaaatt aaaaatgaag    6780 ttttaaatca atctaaagta tatatgagta aacttggtct gacagttacc aatgcttaat    6840
cagtgaggca cctatctcag cgatctgtct atttcgttca tccatagttg cctgactccc    6900
cgtcgtgtag ataactacga tacgggaggg cttaccatct ggccccagtg ctgcaatgat    6960
accgcgagaa ccacgctcac cggctccaga tttatcagca ataaaccagc cagccggaag    7020
ggccgagcgc agaagtggtc ctgcaacttt atccgcctcc atccagtcta ttaattgttg    7080
ccgggaagct agagtaagta gttcgccagt taatagtttg cgcaacgttg ttgccattgc    7140
tacaggcatc gtggtgtcac gctcgtcgtt tggtatggct tcattcagct ccggttccca    7200
acgatcaagg cgagttacat gatcccccat gttgtgcaaa aaagcggtta gctccttcgg    7260
tcctccgatc gttgtcagaa gtaagttggc cgcagtgtta tcactcatgg ttatggcagc    7320
actgcataat tctcttactg tcatgccatc cgtaagatgc ttttctgtga ctggtgagta    7380
ctcaaccaag tcattctgag aatagtgtat gcggcgaccg agttgctctt gcccggcgtc    7440
aatacgggat aataccgcgc cacatagcag aactttaaaa gtgctcatca ttggaaaacg    7500
ttcttcgggg cgaaaactct caaggatctt accgctgttg agatccagtt cgatgtaacc    7560
cactcgtgca cccaactgat cttcagcatc ttttactttc accagcgttt ctgggtgagc    7620
aaaaacagga aggcaaaatg ccgcaaaaaa gggaataagg gcgacacgga aatgttgaat    7680
actcatactc ttcctttttc aatattattg aagcatttat cagggttatt gtctcatgag    7740
cggatacata tttgaatgta tttagaaaaa taaacaaata ggggttccgc gcacatttcc    7800
ccgaaaagtg ccacctaaat tgtaagcgtt aatattttgt taaaattcgc gttaaatttt    7860
tgttaaatca gctcattttt taaccaatag gccgaaatcg gcaaaatccc ttataaatca    7920
aaagaataga ccgagatagg gttgagtggc cgctacaggg cgctcccatt cgccattcag    7980
gctgcgcaac tgttgggaag ggcgtttcgg tgcgggcctc ttcgctatta cgccagctgg    8040
cgaaaggggg atgtgctgca aggcgattaa gttgggtaac gccagggttt cccagtcac    8100 gacgttgtaa aacgacggcc agtgagcgcg acgtaatacg actcactata gggcgaattg    8160
gcggaaggcc gtcaaggccg catgaatt                                       8188
```

<210> SEQ ID NO 11
<211> LENGTH: 3996
<212> TYPE: DNA
<213> ORGANISM: Artificial sequence
<220> FEATURE:
<223> OTHER INFORMATION: M2-gene-Long_RSV1-FLAG_Tx V12.A.8

-continued

<400> SEQUENCE: 11

```
gaagttccta ttccgaagtt cctattctct agaaagtata ggaacttcct ggctcagaaa        60
aagggccctg acaactcttt tcatcttcta ggcggttcct ctacatccgg tggatctgga       120
tctgggcatg tggttgaggg gcttgctggc gaactagagc aattgcgagc ccgcctcgaa       180
caccatcctc aaggtcaata aagactcgag cacctgatcc tgatcataat caagccatat       240
cacatctgta gaggtttact tgctttaaaa aacctccaca cctcccctg aacctgaaac        300 ataaaatgaa tgcaattgtt gttgttaact tgtttattgc agcttataat ggttacaaat       360
aaagcaatag catcacaaat ttcacaaata aagcattttt ttcactgcat tctagttgtg       420
gtttgtccaa actcatcaat gtatcttatc atgtctggat ctgctgaaga gcgctgatca       480
gctcttcacc atagagccca ccgcatcccc agcatgcctg ctattgtctt cccaatcctc       540 cccccttgctg tcctgcccca ccccacccccc cagaatagaa tgacacctac tcagacaatg       600
cgatgcaatt tcctcatttt attaggaaag acagtgggga gtggcacctt ccagggtcaa       660
ggaaggcacg ggggagggc aaacaacaga tggctggcaa ctagaaggca cagtcgggtg       720
ctagcgaaga ccgagcggtg gatccgtatg gtgacaagac gactagtgtg aacgacctgt       780
tagagaaccc ggcacatctg tcgagaggta cgaccgtgca ctaagcttcg caaggtcagt       840
ggagctatcg agtgtaggat ggttcaagtc tgccaatgga gctacagaag tcgaagccgt       900
ccagatctgg actatagtca cttatcgtca tcgtccttat aatcaatatc gtggtcttta       960
taatctccat catgatcctt gtaatccccg ggggtggtat cgttgttctt ggcgtggtcg      1020
ttggtgtcgt tgacggtgct ctctttggga ttgttgatgg tgatgctctt gtggatgtcc      1080
agggtgttct tgatggtttt cttcagcacg tcggcaggca gccgcttcag cagatggatg      1140
gtctgcttgt tgttcttccg gttgctctcg atgtagctga tcacggtgtt gtacacccgg      1200
atcttggggc tgttaggttc ctcgttgtcc cgcagcttct tgatgtcgtc gctgttcagc      1260
tctgtcagca gcttgctcat ggccacgcag gcgctctgct tggtgatgtt gttgatgctg      1320
ccgatatagc tttccagcac gcccacaacg cccagggcat attcctcggt tctatccagt      1380
tcggcggctc cgctgatctc gctcaggggtg tcgatgctct tatccatgga cttcaggatt      1440
ctgttcagca tgaagttctg ccgcacgagc agagcgtgag gaggccactc gaagtagttg      1500
tggctgaagt ggcatctctt gccgttcagg cagtggcctc tgatctcgaa cttgcagggg      1560
ttccgtctgc tcatggtggc ggtattgtct tcggtaccgc acgaagttcc tattcggaag      1620
ttcctattct tcaaatagta taggaacttc cgctctgacc agctgcatta acatggtcat      1680
agctgtttcc ttgcgtattg ggcgctctcc gcttcctcgc tcactgactc gctgcgctcg      1740
gtcgttcggg taaagcctgg ggtgcctaat gagcaaaagg ccagcaaaag gccaggaacc      1800
gtaaaaaggc cgcgttgctg gcgtttttcc ataggctccg ccccctgac gagcatcaca       1860 aaaatcgacg ctcaagtcag aggtggcgaa acccgacagg actataaaga taccaggcgt      1920 ttcccctgg aagctccctc gtgcgctctc ctgttccgac cctgccgctt accggatacc       1980
tgtccgcctt tctcccttcg ggaagcgtgg cgctttctca tagctcacgc tgtaggtatc      2040
tcagttcggt gtaggtcgtt cgctccaagc tgggctgtgt gcacgaaccc cccgttcagc      2100
ccgaccgctg cgccttatcc ggtaactatc gtcttgagtc caacccggta agacacgact      2160
tatcgccact ggcagcagcc actggtaaca ggattagcag agcgaggtat gtaggcggtg      2220
ctacagagtt cttgaagtgg tggcctaact acggctacac tagaagaaca gtatttggta      2280
tctgcgctct gctgaagcca gttaccttcg gaaaaagagt tggtagctct tgatccggca      2340
```

-continued

```
aacaaaccac cgctggtagc ggtggttttt ttgtttgcaa gcagcagatt acgcgcagaa        2400
aaaaaggatc tcaagaagat cctttgatct tttctacggg gtctgacgct cagtggaacg        2460
aaaactcacg ttaagggatt ttggtcatga gattatcaaa aaggatcttc acctagatcc        2520 tttaaatta aaaatgaagt tttaaatcaa tctaaagtat atatgagtaa acttggtctg        2580
acagttacca atgcttaatc agtgaggcac ctatctcagc gatctgtcta tttcgttcat        2640
ccatagttgc ctgactcccc gtcgtgtaga taactacgat acgggagggc ttaccatctg        2700
gccccagtgc tgcaatgata ccgcgagaac cacgctcacc ggctccagat ttatcagcaa        2760
taaaccagcc agccggaagg gccgagcgca gaagtggtcc tgcaacttta tccgcctcca        2820
tccagtctat taattgttgc cgggaagcta gagtaagtag ttcgccagtt aatagtttgc        2880
gcaacgttgt tgccattgct acaggcatcg tggtgtcacg ctcgtcgttt ggtatggctt        2940
cattcagctc cggttcccaa cgatcaaggc gagttacatg atcccccatg ttgtgcaaaa        3000
aagcggttag ctccttcggt cctccgatcg ttgtcagaag taagttggcc gcagtgttat        3060
cactcatggt tatggcagca ctgcataatt ctcttactgt catgccatcc gtaagatgct        3120
tttctgtgac tggtgagtac tcaaccaagt cattctgaga atagtgtatg cggcgaccga        3180
gttgctcttg cccggcgtca atacgggata ataccgcgcc acatagcaga actttaaaag        3240
tgctcatcat tggaaaacgt tcttcggggc gaaaactctc aaggatctta ccgctgttga        3300
gatccagttc gatgtaaccc actcgtgcac ccaactgatc ttcagcatct tttactttca        3360
ccagcgtttc tgggtgagca aaaacaggaa ggcaaaatgc cgcaaaaaag ggaataaggg        3420
cgacacggaa atgttgaata ctcatactct tcctttttca atattattga agcatttatc        3480
agggttattg tctcatgagc ggatacatat ttgaatgtat ttagaaaaat aaacaaatag        3540
gggttccgcg cacatttccc cgaaaagtgc cacctaaatt gtaagcgtta atattttgtt        3600
aaaattcgcg ttaaattttt gttaaatcag ctcattttt aaccaatagg ccgaaatcgg        3660
caaaatccct tataaatcaa aagaatagac cgagataggg ttgagtggcc gctacagggc        3720
gctcccattc gccattcagg ctgcgcaact gttgggaagg gcgtttcggt gcgggcctct        3780
tcgctattac gccagctggc gaaagggga tgtgctgcaa ggcgattaag ttgggtaacg        3840
ccagggtttt cccagtcacg acgttgtaaa acgacggcca gtgagcgcga cgtaatacga        3900
ctcactatag ggcgaattgg cggaaggccg tcaaggccgc atgaattcgc taccgggagt        3960
tggtaggtaa gtggctgggg ccagagactg gctctt                                  3996
```

<210> SEQ ID NO 12
<211> LENGTH: 20
<212> TYPE: DNA
<213> ORGANISM: Artificial sequence
<220> FEATURE:
<223> OTHER INFORMATION: turboRFP_GT_F1 1.I.7

<400> SEQUENCE: 12

```
gagaggccat tctcagatgg                                                      20
```

<210> SEQ ID NO 13
<211> LENGTH: 20
<212> TYPE: DNA
<213> ORGANISM: Artificial sequence
<220> FEATURE:
<223> OTHER INFORMATION: turboRFP_GT_R1 1.I.8

<400> SEQUENCE: 13

-continued cgggcatctt caggttcttg                                                          20

<210> SEQ ID NO 14
<211> LENGTH: 25
<212> TYPE: DNA
<213> ORGANISM: Artificial sequence
<220> FEATURE:
<223> OTHER INFORMATION: turboRFP_probe_FAM 1.I.9

<400> SEQUENCE: 14
ctacctgcac tgctccttca agacc                                                    25

<210> SEQ ID NO 15
<211> LENGTH: 26
<212> TYPE: DNA
<213> ORGANISM: Artificial sequence
<220> FEATURE:
<223> OTHER INFORMATION: TRAC_TCRA-promoter_F1 10.A.10

<400> SEQUENCE: 15
gacttgtcac tggatttaga gtctct                                                   26

<210> SEQ ID NO 16
<211> LENGTH: 22
<212> TYPE: DNA
<213> ORGANISM: Artificial sequence
<220> FEATURE:
<223> OTHER INFORMATION: TRAC_probe (HEX) 10.B.6

<400> SEQUENCE: 16
atccagaacc ctgaccctgc cg                                                       22

<210> SEQ ID NO 17
<211> LENGTH: 23
<212> TYPE: DNA
<213> ORGANISM: Artificial sequence
<220> FEATURE:
<223> OTHER INFORMATION: TRAC-TCRA-ex1-F1 10.A.9

<400> SEQUENCE: 17
ctgatcctct tgtcccacag ata                                                      23

<210> SEQ ID NO 18
<211> LENGTH: 19
<212> TYPE: DNA
<213> ORGANISM: Artificial sequence
<220> FEATURE:
<223> OTHER INFORMATION: AAVS1_GT_F5 15.F.9

<400> SEQUENCE: 18
actctgccct ctaacgctg                                                          19

<210> SEQ ID NO 19
<211> LENGTH: 20
<212> TYPE: DNA
<213> ORGANISM: Artificial sequence
<220> FEATURE:
<223> OTHER INFORMATION: AMPN-TMD_GT_R1 19.E.7

<400> SEQUENCE: 19
gctgatgtag aagcccttgg                                                          20

<210> SEQ ID NO 20
<211> LENGTH: 876
<212> TYPE: DNA
<213> ORGANISM: Artificial sequence -continued

```
<220> FEATURE:
<223> OTHER INFORMATION: SurfaceTag with Barcode FLAG-MYC-HA

<400> SEQUENCE: 20
atggaggagg acagtacag cgagatcgag gagctgccca ggagaaggtg ctgcaggaga      60
ggcacccaga tcgtgctgct gggactggtg accgctgctc tgtgggcagg actgctgaca     120
ttgctgttgc tgtggcactg ggacaccacc cagagcctga agcagctgga ggagggaggt     180
cctggatccg gaacaggtgg ctctggcact ggaggatcag gtccaggtgg atctatggtg     240
aagcagatcg agagcaagac tgctttccag gaagccttgg acgctgcagg tgataagctt     300
gtagtagttg acttctcagc aacgtggtct ggaccttcca agatgatcaa gcctttcttc     360
cattccctct ctgagaagta ttccaacgtg atattccttg aagtagatgt ggatgactct     420
caggatgttg cttcagagtg tgaagtcaaa tccatgccaa cattccagtt cttcaagaag     480
ggacagaagg tgggtgaatt ttctggagcc aataaggaga agcttgaagc caccattaac     540
gagttggtcg gtggttcctc tacatccggt ggatctggat ctggtgatta caaggatcat     600
gatggagatt ataaagacca cgatattgat tataaggacg atgacgataa gggaggatat     660
ccgtatgatg taccagacta cgctggatac ccttacgatg tacctgatta tgccggatac     720
ccctatgacg taccggacta tgcgggagga gaacaaaagc tcatctctga ggaggacctt     780
ggggagcaga agctaatcag tgaagaggac ctcggagagc agaaattgat tagcgaagag     840
gatcttggcg ggcaccatca tcatcaccac cactaa                               876

<210> SEQ ID NO 21
<211> LENGTH: 20
<212> TYPE: DNA
<213> ORGANISM: Artificial sequence
<220> FEATURE:
<223> OTHER INFORMATION: ORF-AM_GT_F2

<400> SEQUENCE: 21
ttctgtagct ccattggcag                                                  20

<210> SEQ ID NO 22
<211> LENGTH: 20
<212> TYPE: DNA
<213> ORGANISM: Artificial sequence
<220> FEATURE:
<223> OTHER INFORMATION: ORF-AM_GT_R1

<400> SEQUENCE: 22
atccgtatgg tgacaagacg                                                  20

<210> SEQ ID NO 23
<211> LENGTH: 26
<212> TYPE: DNA
<213> ORGANISM: Artificial sequence
<220> FEATURE:
<223> OTHER INFORMATION: TRAC-TCRA-ex1-F1

<400> SEQUENCE: 23
gacttgtcac tggatttaga gtctct                                           26
```

CELL SURFACE TAG EXCHANGE (CSTE) SYSTEM FOR TRACING AND MANIPULATION OF CELLS DURING RECOMBINASE MEDIATED CASSETTE EXCHANGE INTEGRATION OF NUCLEIC ACID SEQUENCES TO ENGINEERED RECEIVER CELLS

CROSS-REFERENCE TO RELATED APPLICATIONS

The present application is the U.S. National Stage of International Application PCT/EP2019/068343, filed Jul. 9, 2019, and claims priority to European Patent Application No. 18182353.5, filed Jul. 9, 2018.

SEQUENCE LISTING

The instant application contains a Sequence Listing which has been submitted electronically in ASCII format and is hereby incorporated by reference in its entirety. Said ASCII copy, created on Jun. 16, 2021 and is named 20160615-Updated-Sequence-Listing.txt and is 69,240 bytes in size.

FIELD OF INVENTION

The present invention relates to the fields of cell engineering and recombinant DNA technology. In particular the invention relates to systems and methods for generating, purifying, tracing and manipulating engineered cells during recombinase mediated cassette exchange (RMCE) based integration of a gene of interest.

BACKGROUND

Within the field of genetic manipulation and immunology the Recombinase-mediated cassette exchange (RMCE) has become a useful tool for targeted genetic modifications, see e.g. Turan et al. Gene (2013): 515:1-27. Generally, post-RMCE methods to confirm integration of the gene of interest (GOI) in the correct location require cellular disruption and sample processing. A recently described approach overcomes such need for cellular disruption and demonstrates that recombination events can be monitored and isolated by following expression of fluorescent marker proteins (Phan et al. Sci Rep. (2017): 7 (1): 17771). Although the approach by Phan et al avoids the need for cellular disruption, as it relies on intracellular protein fluorescence, the technique is not suited for high-content screening of integrated constructs due to a limited set of unique spectral properties provided by the fluorescent proteins; as a result only a limited number of genes may be labelled and detected simultaneously using the described strategy. Furthermore, intracellular fluorescent proteins are not amenable to physical manipulation to partition cells via substrate affinity methods such as magnetic activated cell sorting (MACS), which provides potential for high throughput and parallelisation during cell engineering workflows, or potential for increasing the efficiency of high-content cell library engineering.

Currently, with the RMCE technique at hand there is a need for tools for rapid and robust cell engineering in both high-throughput and high-content applications, particularly in cases where cells have been simultaneously transfected with a pool of vectors containing a pool of individual genes of interest, or in cases where selection of cells by substrate affinity methods is desirable. There is thus a clear need for providing effective and improved methods.

SUMMARY

The present invention relates to the provision of a two-component cell surface tag exchange (CSTE) system for tracing and manipulation of engineered cells during recombinase mediated cassette exchange (RMCE) based integration of a gene of interest (GOI). The first part of the CSTE system represents a tag-exchange donor vector (TEDV) encoding the GOI for integration, along with a first cell surface tag (CST) flanked by a 3' fragment of an intron sequence including the splice acceptor site. The TEDV construct is flanked by RMCE elements. The second part of the CSTE represents a tag-exchange receiver site (TERS) contained within the genome of an engineered target cell, encoding a selection gene, and a second CST with an in-frame transmembrane domain, adjoined by a complete intron sequence that also encodes a RMCE element, and a second RMCE element flanking the GOI coding sequence. The CST encoded by the TERS is essentially encoded as two exons adjoined by a single intron. Paired RMCE elements included in both the TEDV and TERS are designed such that execution of RMCE between the two constructs results in exchange of CST and GOI from the TEDV into the TERS, with reciprocal loss off the TERS CST and selection gene encoded by the TERS. The CST delivered by the TEDV utilises the transmembrane domain encoded by the TERS, wherein execution of RMCE results in exchange of the unique CST exon sequences. Promoter elements that drive CST and selection gene/GOI expression from the TERS are extrinsic to the RMCE exchanged constructs, thus sequences delivered by the TEDV will generally only be expressed upon faithful execution of RMCE. This CSTE system enables rapid and robust RMCE that is conditionally reported by detection of the affinity epitopes presented at the cell surface by the CST, and which also enables physical partitioning of cells with substrate-immobilised affinity methods. This CSTE system also enables multiplexing and lineage tracing of GOI integration through use of multivalent affinity epitopes as CST elements. The CSTE system represents a powerful tool for rapid and robust cell engineering in both high-throughput and high-content applications.

In a first aspect the present invention provides a combined system comprising two separate components, wherein the first component is a tag-exchange donor vector (TEDV) encoding a first cell surface tag (CST) exon flanked by a 3' intron fragment, and a gene of interest (GOI) in the antisense orientation, and the second component is an engineered cell containing within its genome a tag-exchange receiver site (TERS), encoding a second CST exon adjoined by a full intron sequence to an exon encoding a transmembrane domain, and also encoding a reporter gene in the antisense orientation, wherein paired recombinase mediated cassette exchange (RMCE) elements are included in the TEDV and TERS such that execution of RMCE between the TEDV and TERS results in exchange of the reporter element for the GOI encoded by the TEDV, and exchange of the first CST exon for the second CST exon, such that the derivative engineered cell now expresses the first CST and GOI, in place of the second CST and the reporter gene.

In one embodiment the first component is a TEDV comprising a. a first RMCE element-5'RMCE element encoded in the non-coding and 'non-functional' 3' intron fragment b. a 3' intron fragment, containing a branch point sequence, a polypyrimidine tract and a 3' acceptor splice site c. an exon comprising the TEDV-encoded CST in the 5' to 3' direction d. a first transcriptional terminator sequence for encoded CST in the 5' to 3' direction e. a second transcriptional terminator for the 3' to 5' encoded GOI f. a sequence encoding GOI in the 3' to 5' direction g. a Kozak sequence h. a 5' RMCE element wherein, the CST exon and first transcriptional terminator are encoded in the antisense orientation from the GOI and associated transcriptional terminator and Kozak sequences.

In another embodiment the second component is a TERS comprising a. a transcriptional promoter element b. a Kozak sequence c. a Type 2 membrane protein transmembrane domain exon d. a 5' intron splice donor site e. a 5' RMCE element encoded in the non-coding and 'non-functional' 3' intron fragment, as equivalent, and paired with, the 5' RMCE element of the TEDV f. functional sequences of the 3' intron fragment, containing a branch point sequence, a polypyrimidine tract and a 3' acceptor splice site g. an exon comprising the TERS-encoded CST in the 5' to 3' direction (that is different to the TEDV-encoded CST)

h. a transcriptional terminator sequence for encoded CST in the 5' to 3' direction i. a transcriptional terminator sequence for the 3' to 5' direction j. a sequence encoding the selection gene in the 3' to 5' direction k. a Kozak sequence for efficient translational initiation of the selection gene transcript l. a 3' RMCE element m. a 3' genomic element responsible for regulating expression and tracking of the CST transcript, wherein the transmembrane domain exon and CST exon are encoded in the antisense orientation from the reporter gene, such that the first transcriptional promoter element drives transcription of the combined transmembrane domain and CST, and the second transcriptional promoter element drives transcription of the reporter gene.

In a second aspect the present invention provides a method for generating derivative engineered cells expressing a TEDV-encoded GOI from the TERS locus, said method comprising, a. generating a TEDV encoding a GOI b. delivering said TEDV to an engineered cell line containing a paired TERS, along with the recombinase enzyme matching the RMCE elements encoded therein c. contacting cells with two or more affinity reagents specific for both the TEDV-encoded CST and TERS-encoded CST d. selecting derivative engineered cells on the basis of diminished expression of the reporter gene and TERS-encoded CST, and increased expression of the TEDV-encoded CST, as a proxy for selection of cells with integrated GOI.

In a third aspect the present invention provides a tag-exchange donor vector (TEDV) encoding a cell surface tag (CST) exon flanked by a 3' intron fragment, and a gene of interest (GOI) in the antisense orientation.

In a fourth aspect the present invention provides an engineered cell containing within its genome a tag-exchange receiver site (TERS), encoding a cell surface tag (CST) exon adjoined by a full intron sequence to an exon encoding a transmembrane domain, and also encoding a reporter gene in the antisense orientation, wherein a recombinase mediated cassette exchange (RMCE) element is included in the TERS such that execution of RMCE between TERS and a tag-exchange donor vector (TEDV) results in exchange of the reporter element for a gene of interest (GOI) encoded by the TEDV.

The present invention provides a system to integrate a GOI into an engineered cell line by means of RMCE, wherein reporting of said integration is conditionally detected by analysis of a co-integrated cell surface tag (CST). Moreover, upon integration of the GOI, a concomitant loss of a distinct CST from the engineered cell line permits dual positive/negative selection of GOI-expressing derivative engineered cells. This 'tag-exchange' is highly robust and the basis for the stringent positive/negative selection enabled by the CSTE system. A second selection gene is also lost from the TERS site, enabling a highly robust double negative selection and single positive selection during generation of derivative engineered cells expressing the GOI. Importantly, the nature of the CST system means that not only are these markers conditional, requiring selective addition of cognate affinity reagents for detection, but may also be leveraged to physically partition target cell populations by use of substrate-immobilised affinity reagent methodologies. This enables efficient high-throughput methods for derivative engineered cell generation through the partitioning of cells using methods such as magnetic activated cell sorting (MACS), as opposed to more time-consuming and difficult to parallelise methodologies such as florescence-activated cell sorting (FACS). Finally, the CSTE system, in replacing the intracellular expression of fluorescence proteins and antibiotic resistance genes as markers of integration, provides a much larger selectable marker space. In particular, the generation of a large number of unique CST epitopes for conditional selection is readily achieved, as opposed to florescent proteins with broad spectral overlap, or the highly limited set of antibiotic resistance genes. This broader access to selectable markers enables different forms of high-throughput derivative cell production with increased efficiency, and further enables high-content methods for both cell library creation and cell lineage tracking in cellular engineering, pathway engineering and experimental workflows.

DETAILED DESCRIPTION

The overall architecture and operation of the CSTE system is depicted in FIG. 1. The CSTE system operates as a donor/receiver pair, wherein the tag-exchange donor vector (TEDV) acts to deliver a GOI sequence, and a cell-surface tag (CST) exon to a paired tag-exchange receiver site (TERS), which is generally contained within the genome of an engineered cell line. The TERS encodes a distinct CST exon and a selection gene, which are exchanged with the TEDV-encoded CST and GOI, respectively.

The TEDV-encoded CST exon is encoded in the sense (5' to 3') direction and in frame with a 3' intron fragment, which includes splice acceptor site, polypyrimidine tract and branch point sequences. To the 5' of these functional intronic sequences, within the 'non-functional' intronic sequence, is encoded a first RMCE element. The GOI is encoded in the antisense (3' to 5') direction. To the 3' end of the construct adjacent to the GOI transcriptional start site a second RMCE element is encoded.

The paired TERS construct carried by an engineered cell line encodes a CST exon in frame with a complete intron sequence, with a first RMCE element within the 'non-functional' intronic sequence, paired with, and in equivalent context of the first RMCE element of the TEDV. The complete intron sequence in which this first RMCE site is encoded includes a 5' splice donor site, itself encoded in-frame with a transmembrane domain (TD) exon. This TD contains the transcriptional start site and promoter sequences to drive transcription to the 5' of the TERS construct. Thus, the TERS-encoded CST is expressed at the cell surface once translated from the spliced transcript. Similarly, once RMCE is executed between TEDV and TERS, the TEDV-encoded in the CST exon is exchanged with the TERS-encoded CST exon. This results in the execution of a 'tag-exchange', wherein the derivative engineered cell line now expresses the TEDV-encoded CST at the cell surface, and not the TERS-encoded CST. In this process, the TEDV-encoded CST exon 'acquires' the 5' splice donor sites, TD domain, transcriptional start site and promoter sequences from the TERS construct to enable the expression of the TEDV-encoded CST, providing a stringent site-specific control over integration of TEDV-encoded sequences.

As mentioned above, the TERS encodes a selection gene in the antisense (3' to 5') direction, with a promoter sequence able to drive the transcription of this selection gene to the 3' end of the TERS construct. Between the transcriptional start site of the selection gene and the 3' promoter sequence of the TERS, a second RMCE element is encoded, paired to the second 5' RMCE element encoded in the TEDV. Therefore, when RMCE is executed between the TEDV and TERS, the TEDV-encoded GOI is exchanged with the TERS-encoded selection gene.

It is important to note that the TEDV contains no promoter sequences, and thus both the TEDV-encoded CST exon and GOI must be complimented with promoter sequences to enable their transcription. Importantly, the inclusion of the intron and TD exon complementation for the CST exon, as outlined above, provides an even more stringent site selectivity for integration of TEDV-encoded sequences. The use of the intron element in the CSTE provides an additional level of assurance that random integration of the construct will not provide an expressible TEDV-encoded CST on the cell surface. In contrast to a donor vector that would deliver the full CST ORF, including the TD, the CSTE system provides only the CST epitope exon and a splice acceptor site. Thus, a random aberrant integration of the donor construct would not only need to integrate adjacent to an active promoter, but would also require acquisition of a Type II transmembrane domain, or equivalent, with an appropriate 5' splice donor sequence. This results in the occurrence of a randomly integrated construct expressing a TEDV-encoded CST being extremely unlikely, minimising the selection of such random and undesired events during generation of derivative engineered cells expressing the delivered GOI.

The specific architecture of the CSTE system componentry, comprising the TEDV and the TERS, is detailed below.

TERS Architecture

The TERS, contained within an engineered cell line, constitutively expresses a TERS-encoded CST and selection gene, which upon execution of RMCE with a paired TEDV are exchanged with a TEDV-encoded CST and a GOI, respectively. The generic architecture of a TERS is depicted in FIG. 3.

A TERS typically comprises:

a) a Kozak sequence b) an exon encoding a Type 2 membrane protein transmembrane domain.

c) a 5' intron splice donor site.

d) a 5' RMCE element encoded in the non-coding and 'non-functional' 3' intron fragment, as equivalent, and paired with, the 5' RMCE element of the TEDV.

e) the functional sequences of the 3' intron fragment, containing a branch point sequence, a polypyrimidine tract and a 3' acceptor splice site.

f) an exon comprising the TERS-encoded CST in the 5' to 3' direction.

g) a transcriptional terminator sequence for encoded CST in the 5' to 3' direction.

h) a transcriptional terminator sequence for the 3' to 5' encoded selection gene.

i) a sequence encoding the selection gene in the 3' to 5' direction j) a Kozak sequence for efficient translational initiation of the selection gene transcript k) a 3' RMCE element x) a 5' genomic element responsible for regulating expression and tracking of the CST transcript. This genomic element minimally includes a promoter sequence that drives CST transcription.

y) a 3' genomic element responsible for regulating expression and tracking of the selection gene transcript. This genomic element minimally includes a promoter sequence that drives selection gene transcription;

wherein; a) is provided to ensure efficient translational initiation from the adjoined TD/CST transcript driven from the TERS, both for the TERS-encoded CST prior to execution to RMCE, and the TEDV-encoded CST subsequent to execution of RMCE; b) represents the TD that is adjoined to the CST exon by transcript splicing, and mediates the inserts of the translated protein construct in the cell plasma membrane and presents the CST to the extracellular space; c) is the RMCE element that is situated within the intron sequence of the TERS construct, and is equivalent to the 5' RMCE element of the TEDV, mediating CST exon exchange upon execution of RMCE within the CSTE system; e) is the splice acceptor site and associated functional sequence of the intron, enabling splicing of the intron, containing the RMCE element, from the TD/CST transcript driven from the TERS; f) is the exon encoding the CST epitope(s) within the TERS site, such that the expressed TD/CST protein presents said epitope to the extracellular space, and which can be conditionally detected with cognate affinity reagent; g) represents a transcriptional terminator for the TD/CST open reading frame encoded in the 5' to 3' direction; h) represents a transcriptional terminator for the selection gene open reading frame encoded in the 3' to 5' direction within the TERS; i) represents an open reading frame encoding a selection gene expressed from the TERS in the engineered cell line; j) is a Kozak sequence provided to ensure efficient translational initiation from the selection gene transcript driven from the TERS prior to execution of RMCE; k) is the RMCE element that is situated between the transcriptional start site of the selection gene and the promoter sequences driving transcription of this open reading frame, and is equivalent to the 3' RMCE element of the TEDV, mediating exchange of selection gene with the TEDV-encoded GOI upon execution by RMCE within the CSTE system; x) minimally represents promoter sequences that drive the transcription of the TD/CST open reading frame encoded by the TERS prior to RMCE, and the TEDV-encoded TD/CST subsequent to execution of RMCE; y) minimally represents promoter sequences that drive the transcription of the selection gene open reading frame encoded by the TERS prior to RMCE, and the TEDV-encoded GOI subsequent to execution of RMCE.

A schematic representation of the TERS cloning fragment is presented in FIG. 3.

The TERS essentially encodes a fully functional intron sequence that contains the 5' RMCE site. Such a sequence may represent any intron that enables efficient splicing of the TD/CST transcript in the context of the host engineered cell. The splice acceptor site of the TEDV is required to be functional in concert with the splice donor site of the TERS. Thus, the TEDV and TERS encoded splice acceptor sequence should be the same or equivalent.

The non-coding and 'non-functional' intron sequence, wherein the RMCE site is encoded, may also encode further genetic elements such as transcriptional enhancers, transcriptional insulators, distinct open reading frames encoding separate desirable components for function or reporting of the TERS construct within the engineered cell, or other unique sequences used for transcript and/or construct tracing and quantification.

In the context of the TERS, both the encoded TD/CST and the selection gene may contain 5' and 3' untranslated regions (UTR), which encode unique sequences used for transcript and/or construct tracing and quantification, or impart regulation of transcript stability, for example.

The selection gene can be selected from
a. an antibiotic resistance gene,
b. a reporter gene
c. an auxotroph complementing gene,
d. an inducible suicide gene
    wherein the choice, formatting and application of such positive selection markers are well known to those skilled in the art. The use of an inducible suicide gene may be used to eliminate parental engineered cells after execution of RMCE in the generation of derivative engineered cells expressing the GOI. A reporter gene may represent a unique TD/CST construct for conditional or constitutive reporting at the cell surface. Multiple selection genes may be included in this portion of the TERS, to enable positive selection during engineered cell line generation, and negative selection during derivative engineered cell line generation.

The 5' and 3' genomic elements minimally encode promoter sequences that mediate the transcription of the TD/CST and selection genes. Such promoters may represent constitutive of inducible promoters. These genomic elements may also encode further genetic elements such as transcriptional enhancers, transcriptional insulators, distinct open reading frames encoding separate desirable components for function or reporting of the TERS construct within the engineered cell, or other unique sequences used for construct tracing and quantification.

It is important to note, that in the present description, the TD/CST is encoded in the sense (5' to 3') direction, and the selection gene in the antisense (3' to 5') direction (as depicted in FIG. 3). This is for clarity of description. There is no practical reason why these orientations could not be reversed in the TERS/TEDV context, provided that the TD/CST construct can incorporate a functional intron sequence that also encodes a RMCE site paired with an equivalent RMCE site within the 3' intron fragment of the TEDV.

The inclusion of a selection gene is not absolutely required for the operation of the CSTE system, however, is desirable as to aid in the triple selection for the expression of the GOI interest upon execution of RMCE. Moreover, the generation and maintenance of the engineered cell line with the use of a reporter in both sense and antisense direction ensures that promoter sequences contained within the 5' and 3' genomic elements are fully functional prior to execution of RMCE to generate the derivative engineered cell expressing the TEDV-encoded GOI.

Cell Surface Tag (CST) Architecture

One of the key functional features of the CSTE system is the use of multiple unique CST constructs to conditionally report the presence of the initial TERS construct, and the exchanged construct incorporating TEDV-encoded sequences upon execution of RMCE.

To achieve the TD complementation arrangement within the CSTE system, only certain types of TD exons are suitable. Namely, those that may be spliced with the CST exon situated to the 3', while also permitting the CST protein fragment to be exposed extracellularly.

With the objective to simplify the expressed CST epitope-presenting protein product, and to minimise the size and complexity of the TD exon, TDs from Type II membrane proteins are the most suitable. Type II TDs are single pass, and are situated at the N-terminal end of a protein, which faces the cytoplasmic side of the membrane, allowing a C-terminal CST epitope to be exposed extracellularly. Other TDs may be used, including multi-pass TD, with the proviso that the spliced CST transcript exposes the CST epitope to the extracellular space.

The CST exon, which is adjoined to the TD in the spliced transcript, has the function of simply presenting unique epitopes extracellularly that may be conditionally detected by use of cognate affinity reagents. Generally, such epitopes comprise synthetic sequences, sequences encoded by distinct organisms from that of the host engineered cell, or sequences from the same organism as the host engineered cell but are not expressed extracellularly.

It is generally desirable to include a linker domain between the TD and the CST epitope. Since CST epitopes could comprise of as little as a few amino acids, such a linker region ensures the availability of the CST at the cell surface for affinity reagent engagement. Such linker regions may include flexible 'unstructured' regions, or structural fully folded protein domains.

The nature of the epitopes encoded by the CST exons only reflect uniqueness in the context of epitopes otherwise expressed at the cell surface of the engineered cell containing the TERS, and thus may represent any protein sequence to which a specific affinity reagent may be raised.

In general, the CST construct as a whole should be functionally neutral with regard to cell function. Transmembrane domains simply fused, often via a linker sequence; to inert epitope structures without extraneous functional domains are preferred.

In the present context, an affinity reagent is defined as any antibody, peptide, nucleic acid, or other small molecule that specifically binds to a larger target molecule in order to identify, track, capture, or otherwise influence the activity of the CST epitope. Often such affinity reagents will be labelled with fluorescent, colorimetric, radiometric or other detectable labels for tracking of cells expressing a cognate CST. Alternatively, such affinity reagents may be functionalized to substrates to enable substrate affinity enrichment methods to partition CST-expressing engineered cells.

Engineered Cell Line Containing TERS

The cell line that contains the TERS must be engineered, in as much that the synthetic TERS construct has been inserted. In general, this would mean the integration of the TERS construct to the genome of the engineered cell, but may also include other methods for nuclear maintenance of the TERS construct, such as methods for episomal maintenance of genetic constructs.

Methods to integrate constructs to the genome of target mammalian cells are well known to those skilled in the art, and may be achieved via homology directed recombination (HDR) and/or random integration methods, wherein HDR may be promoted by targeted mutation of the genomic loci at which HDR is to occur, and can be achieved via different means, including but not limited to site directed mutagenesis via i. zinc-finger nucleases ii. CRISPR/Cas9 mediated targeting iii. Synthetic transcription activator-like effector nucleases (TALEN)

wherein said site-directed nucleases induce site-specific DNA-repair by HDR at target loci. After such events, a proportion of cells will have incorporated HDR vector, and can be selected and/or determined via any combination of the following, iv. Non-destructive phenotypical expression analysis V. Destructive phenotypical expression analysis vi. Genetic analysis Wherein iv and vi are the preferred methods for selection and determination of successful genomic integration events.

Alternatively, viral vectors could be used to deliver the required components in a site-directed or undirected manner.

The methodology of TERS construct integration is not central to the operation of the TERS, provided there is detectable TERS-encoded CST at the cell surface, and presence of an expressed selection gene, indicating that the construct is functional with regard to transcription of contained coding sequences. Indeed, both the TERS-encoded CST and selection genes are convenient selectable markers for the generation of the engineered cell line containing a TERS.

One important aspect to note is the requirement for control of copy number of integrated TERS constructs is required for some applications, especially those leveraging the ability to generate cell-based arrays of derivative engineered cell lines expressing single GOI from a library of TEDV constructs, and similar 'multiplex' methods. Noting this, episomal maintenance of the TERS construct would largely be incompatible with such multiplex methods for derivative engineered cell line generation. Methods for the elucidation of construct copy number within a genome of the engineered cell are well known to those skilled in the art.

TEDV Architecture

The TEDV encodes the CST exon and GOI to be exchanged with the CST exon and selection gene encoded by the TERS upon execution of RMCE, respectively, where the TERS is contained within an engineered cell line. The generic architecture of a TEDV is depicted in FIG. 2.

A TEDV typically comprises 1) a 5' RMCE element encoded in the non-coding and 'non-functional' 3' intron fragment.

2) a 3' intron fragment, containing a branch point sequence, a polypyrimidine tract and a 3' acceptor splice site.

3) an exon comprising the TEDV-encoded CST in the 5' to 3' direction.

4) a transcriptional terminator sequence for encoded CST in the 5' to 3' direction.

5) a transcriptional terminator sequence for the 3' to 5' encoded GOI.

6) a sequence encoding the GOI in the 3' to 5' direction.

7) a Kozak sequence.

8) a 3' RMCE element.

wherein; 1) represents the RMCE element that is situated within the intron non-coding and non-functional sequence of the 3' intron fragment of the TEDV construct, and is equivalent to the 5' RMCE element of the TERS, mediating CST exon exchange upon execution of RMCE within the CSTE system; 2) a 3' intron fragment that provides a branch point sequence, a polypyrimidine tract and a 3' acceptor splice site for execution of efficient splicing of the TD/CST transcript of the integrated TEDV-encoded CST exon after execution of RMCE between TEDV and TERS to generate derivative engineered cell expressing the GOI; 3) is the exon encoding the CST epitope(s) within the TEDV construct, such that the expressed TD/CST protein complemented, subsequent to execution of RMCE between TEDV and TERS, presents said epitope to the extracellular space, and which can be conditionally detected with cognate affinity reagent; 4) represents a transcriptional terminator for the CST exon encoded in the 5' to 3' direction, acting as a transcriptional terminator of the complimented TD/CST with the TEDV-encoded CST upon execution of RMCE; 5) represents a transcriptional terminator for the GOI open reading frame encoded in the 5' to 3' direction within the TEDV, acting as transcriptional termination of the encoded GOI once integrated to the TERS site upon execution of RMCE; 6) represents an open reading frame encoding a GOI to be integrated to the engineered cell to generate a derivative engineered cell expressing the GOI; 7) is provided to ensure efficient translational initiation from the GOI transcript driven from the TERS subsequent to execution of RMCE; 8) is the RMCE element at the 3' end of the TEDV construct, and equivalent to the 3' RMCE site of the TERS situated between the transcriptional start site of the selection gene and the promoter sequences driving transcription of this open reading frame.

A schematic representation of the TEDV cloning fragment is presented in FIG. 2.

The TEDV may represent a synthesised DNA construct, or a cloned construct as produced by methods well known to those skilled in the art. To aid in cloning methodologies, a TEDV may include restriction endonuclease sequences for insertion of varying CST exon and/or GOI sequences into the construct. The inclusion and use of such cloning sites is well known to those skilled in the art.

In the present context, a TEDV will generally be a plasmidic construct propagated in bacteria, and thus may also comprise an origin of replication and a selection gene.

The TEDV may also represent a construct with sequence motifs that enable packaging of said construct into a specific delivery vectors, such as viral vectors well known to those skilled in the art. The use of viral vector transduction of engineered cells containing the TERS would be beneficial for use of the CSTE system in cells that are otherwise difficult to transfect.

The TEDV may represent an RNA construct, which may be reverse transcribed with the provision of appropriate reverse transcriptase.

In the present context, a GOI is defined by any nucleic coding or non-coding sequence of interest. This may include any protein- or polypeptide-open reading frames, non-protein-coding RNA such as microRNA, short hairpin RNA, tRNA or rRNA.

Importantly, a GOI may represent a library of variants of a single open reading frame, and the TEDV-encoding such a GOI may be complied into a pooled library of TEDV. Due to the precise control over copy number enabled by the CSTE system, and the reliable multi-factor and conditional reporting of GOI integration, high-content libraries of derivative engineered cells may be produced expressing just a single GOI in each derivative engineered cell in the pool of target cells. This may be leveraged for a range of cellular, pathway, protein and specific GOI engineering in a viable cell context (see below).

RMCE Elements and Enzymes

The use of site-specific recombinases (SSRs) has proven to be a predictable tool to modify the genome of a cell. There are two major classes of SSRs, Ser integrases that comprise of but not limited to, φC31, γδ-res, ParA, Tn3, Gin, φBT1, R4, Bxb1, TP901-1, and Tyr recombinases, that comprise of but not limited to, Flp, Cre, R. Although both classes are capable of performing RMCE, Ser integrases have the limitation that depending on the initial crossover, thus introduction of either the desired TEDV-encoded CST and GOI or the TEDV vector backbone will occur. Although not all Tyr recombinases have been comprehensively experimentally evaluated, Cre and Flp have been extensively used to perform RMCE. With the objective of integrating a single copy of the TEDV-encoded CST and GOI genetic elements, the use of Flp in conjunction with well characterised heterospecific FRT sites is most suitable because of the lack of pseudo FRT sites encoded in the human genome. This is not the case with Cre which displays promiscuous activity for LoxP genomic pseudosites.

Methods for Derivative Engineered Cell Generation

The use of RMCE in mammalian cells is well known to those skilled in the art, where the donor construct may be delivered to the target cells by a range of methodologies, including but not limited to chemical transfection, electroporation or viral vector delivery. In addition to provision of the donor construct, the specific recombinase enzyme(s) must also be provided. This will generally be provided as a separate expression construct co-delivered to the target cells along with the donor construct. In some instances, it may be desirable to modify engineered cells expressing a TERS to conditionally express the required recombinase enzymes to increase the efficiency of the overall process.

In the context of the CSTE system, once the RMCE has been executed by delivery of the TEDV to the engineered cell containing the TERS, and followed by an outgrowth period, the target cell population may be analysed and or selected for generation of derivative engineered cells expressing the TEDV-encoded GOI. This may be conducted in three ways that are intrinsic to the CSTE system, and independent of detection of the GOI expression.

A derivative engineered cell line may be selected on the basis of a negative selection of the TERS-encoded CST, and/or a positive selection of the TEDV-encoded CST, as a reflection of a successful tag-exchange. These are conditionally reported, and require addition of cognate affinity reagents for each CST. Such selection methodologies may leverage FACS through addition of fluorescently labelled affinity reagents and selection of desired CST expression profiles. Due to the extracellular presentation of the CST epitopes, cell partitioning may also be achieved through substrate-based enrichment approaches, such as MACS.

A further negative selection may be achieved on the basis of the TERS-encoded selection gene, where said selection gene represents a reporter gene or an inducible suicide gene. The reporter gene may utilise FACS in the case of a fluorescent reporter gene, for instance, or FACS and/or MACS if the reporter gene itself represents a unique CST. An inducible suicide gene may be used to negatively select parental engineered cells from the culture; for instance, to enrich for derivative engineered cells expressing the GOI.

Overall the double positive selection and single negative selection provide a highly robust selection of derivative engineered cells, which may be reported conditionally, and may be used to partition the cells with substrate-immobilised affinity reagents. This selection may additionally include positive selection on TEDV-encoded GOI, if the nature of said GOI is amendable to non-destructive detection within the derivative engineered cell. The abovementioned selections may be used in series or in parallel to achieve high-throughput or precise high-content derivative engineered cell populations.

These above phenotypic analysis will generally be supported by genotypic confirmation of copy number of TEDV sequences in the derivative engineered cells, utilising methods well known to those skilled in the art. This may also be achieved phenotypically to an extent, considering the highly standardised context of the CST expression, wherein there very rare instances where aberrant integration of the TEDV constructs results in expression of a TEDV-encoded CST at the cell surface, could be negatively selected by exclusion of cells with high TEDV-encoded CST expression, particularly when utilising FACS selection methodologies. In the case of engineered cells that express multiple TERS sites (see below) a copy number control can similarly be achieved based on the degree of TEDV-encoded CST expressed at the cell surface.

Methods for Substrate-Immobilised Affinity Reagent Partitioning of Cells

A key advantage of the CSTE system is the cell surface exposure of the CST epitopes, and thus the ability to partition cells on the basis of substrate immobilised affinity methods. This is particularly useful for high-throughput methods, or stepwise selection in high-content derivative engineered cell library generation. Methodologies well-known to those skilled in the art are the ferromagnetic bead-based MACS approach, among a variety of other affinity reagent-functionalised substrates for capture and physical partitioning of cells based on specific expression of surface epitopes. Such rapid and conditional positive and/or negative selection based on cell surface CST expression is highly parallelisable and thus amenable to high-throughput methodologies, with far more speed and precision that present antibiotic resistance selection, and far more speed and reduced cost compared to FACS selection limited to intracellular fluorescent proteins. Moreover, the ability to positively and negatively select both parental engineered cell and derivative engineered cells leads to precise high-content library generation of derivative engineered cells expressing one or more GOI.

Methods for Cell Surface 'Barcoding' with Multiple and Multivalent CST

An advantage of the CSTE system is the increased amount of selection marker space available. In contrast to standard fluorescent protein reporter and antibiotic resistance gene systems, which are limited to just a handful of parallelisable markers, many unique markers can be rapidly generated by using simple epitopes with cognate affinity reagents. One is not limited only by the number of CST epitopes and cognate reagents available, as multi-epitope CST domains may readily be constructed for all unique combinations of available CST epitope and cognate detection reagent. The expanded and parallelisable conditional reporter space enables a variety of high-throughput and high-content methodologies.

The use of multiple TEDV-encoded CST epitopes, each associated with a different GOI, or GOI variant sequence, can be used to increase efficiency in high-throughput cell engineering. For instance, a pool of such unique vectors can be integrated into a pool of engineered cells expressing a TERS. These can be bulk handled through negative selection as outlined above, and later partitioned on the basis of unique TEDV-encoded CST expression.

Similarly, the use of multiple TEDV-encoded CST epitopes enables the production of medium-content libraries for viable cell lineage tracking and selection. For instance, a library of GOI associated with unique CSTs can be integrated into a pool of derivative engineered cells, and persistence or function of those cell lineages expressing specific GOI can be traced across time. This can be applied to selections in culture systems for protein, pathway or cellular engineering or analysis, or may similarly be used in instances where cells are grafted to viable animals, and later recovered as viable cells for analysis.

High-Content Libraries and Multi-TERS Engineered Cells

With the robust positive and negative selection of derivative engineered cells expressing a GOI, precise high-content libraries may be generated in multiple modes to support protein, pathway and cellular engineering workflows.

In the simplest conception, a library of TEDV encoding a single CST epitope, but multiple GOIs, may be integrated into a pool of cells. The application of a standard positive/negative CST selection with the TERS- and TEDV-encoded CST epitopes, for example, would derive a population of derivative engineered cells expressing a single GOI variant in each cell of the selected population. These high-content cell libraries may then be subjected to functional selection in workflows to engineer a protein, a cellular pathway or more generally a cellular function, based on the variant GOI incorporated.

With the addition of multiple TERS with unique CST epitopes to a single engineered cell, and multiple TEDV libraries with unique CST epitopes, multiple families of variant GOI may be incorporated into such engineering workflows, treating enzymes in a biosynthetic pathway as combinatorial variant GOI, for instance. Such a context, where an engineered cell containing multiple TERS, could be used to enhance the overall expression of a single GOI. Multi-TERS engineered cells would generally require the use of unique heterospecific recombinase sites for each TERS/TEDV pair to ensure efficiency and stability of GOI integration and selection.

Figure 1:
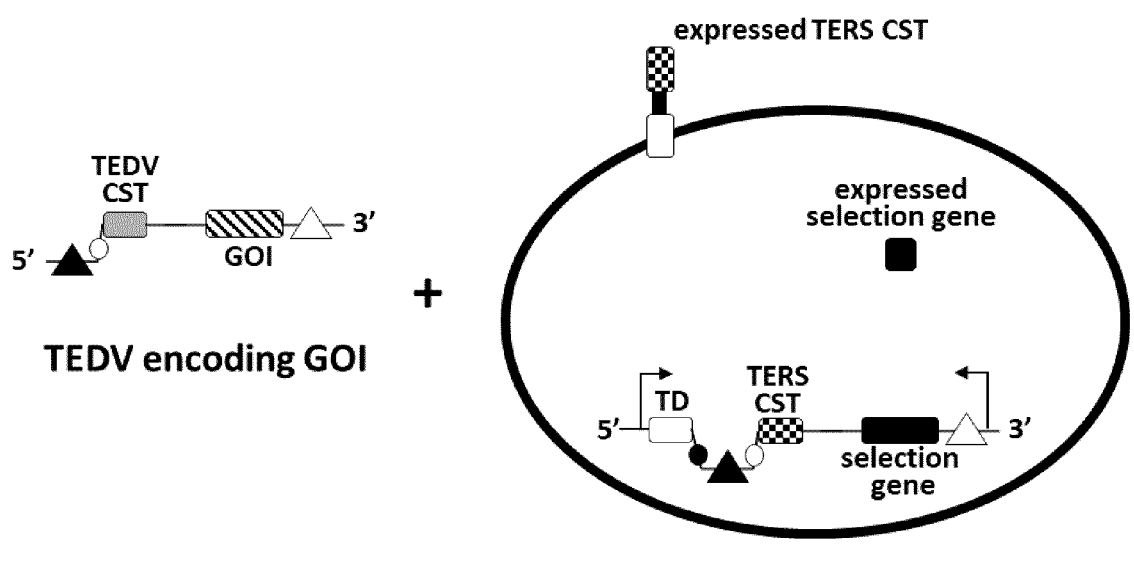
FIG. 1. Composition and Operation of the Cell Surface Tag Exchange (CSTE) System Schematic representation of the CSTE system. The top panel depicts system components, with the Tag Exchange Donor Vector (TEDV), right, and an engineered cell containing Tag Exchange Receiver Site (TERS), left.
Figure 1:
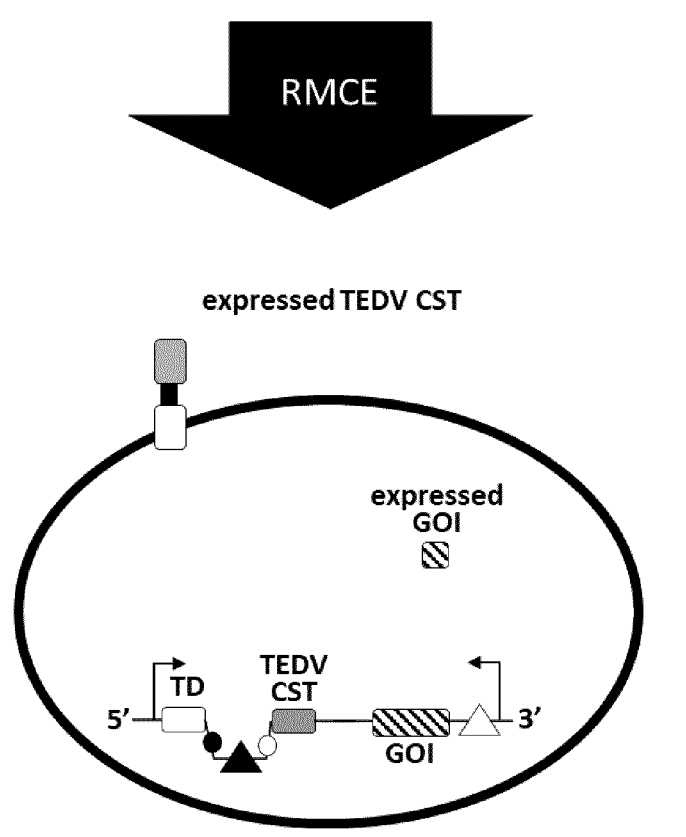

The TEDV encodes RMCE elements at either terminus of the construct (open and closed triangles), which are paired with the RMCE sites contained within the TERS. The RMCE element at the 5' end of the TEDV construct (closed triangle) is encoded within a sequence that represents a 3' intron fragment, wherein immediately to the 3' of the RMCE element is are the 3' elements of an intron (open circle), including a branch point sequence, polypyrimidine tracts and splice acceptor site. Thus, the RMCE is contained within a 'non-functional' and non-coding intron sequence, and where the 3' intron fragment contained within the TEDV lacks a 5' splice donor site. Immediately 3' of the splice acceptor site, the TEDV encodes a 3' exon of a cell surface tag (CST), meaning the exon encodes the portion of the CST containing unique molecular binding motifs (grey rectangle). The CST sequence is encoded in the 5' to 3' direction, where the TEDV also encodes the gene of interest (GOI) to be integrated to the TERS encoded in the 3' to 5' direction (crosshatched rectangle).

The central part of the TERS, contained within an engineered cell, encodes elements distinct from those of the TEDV, though with the same architecture. That is, between the RMCE elements, paired with those of TEDV (open and closed triangles), the TERS encodes a CST exon distinct from that of the TEDV-encoded CST (chequered rectangle), with a splice acceptor site and associated 3' intronic sequence immediately to the 5' of this CST (open circle). Similarly, a selection gene (closed rectangle) is encoded in the antisense direction within the TERS, as is the GOI in the TEDV. At the 5' end of the construct, promoter sequences are included (rightward arrow), to drive transcription of the CST. To the 3' of this promoter sequence, a transmembrane domain (TD) exon is encoded (open rectangle), with a 5' intron sequence immediately to the 3' (closed circle). This means that the TD exon and CST exon, encoded in frame with an RMCE element containing intron, are produced as a contiguous transcript that is spliced to adjoin the exons into a single coding mRNA. The TERS-encoded TD-CST product (open/chequered dumbbell) is expressed on the cell surface. At the 3' terminus of the TERS construct is a separate promoter element that drives transcription of the selection gene (closed rectangle) in the 3' to 5' direction, resulting in the expressed selection gene (closed square).

The introduction of the TEDV to the engineered cell containing the TERS, along with an appropriate expression construct for recombinase specific for the paired RMCE elements in the TEDV/TERS, results in the execution of RMCE, and the generation of a derivative engineered cell expressing the GOI (bottom panel). The TERS-encoded elements have exchanged for the TEDV-encoded elements. The derivative cell line thus expresses the TEDV-encoded CST at the cell surface, as a TD-CST product with the originally TERS-encoded TD (open/grey dumbbell), and the GOI (crosshatched square).

Overall, execution of RMCE between the TEDV and TERS results in the generation of a derivative engineered cell that has lost expression of the selection gene and the TERS-encoded CST, and has gained expression of the TEDV-encoded CST and GOI.

Figure 2:
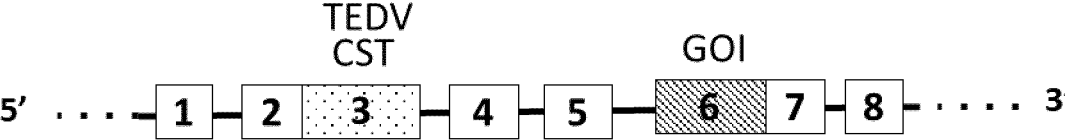

FIG. 2. The Tag-Exchange Delivery Vector (TEDV) Architecture

A schematic representation of the TEDV, depicted as a linear construct with each numbered box representing a key element of the construct architecture. The construct contains both the TEDV-encoded CST, and the gene of interest (GOI).

Figure 3:
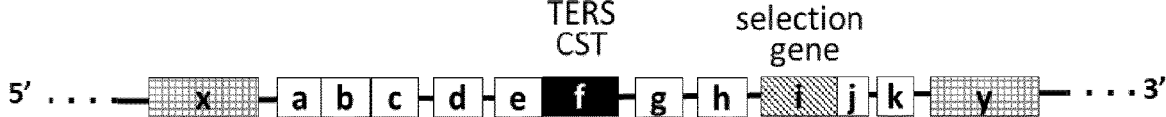

1) Represents the 5' RMCE element encoded in the non-coding and 'non-functional' 3' intron fragment.
2) Represents functional sequences of the 3' intron fragment, containing a branch point sequence, a polypirimidine tract and a 3' acceptor splice site.
3) Represents an exon encoding the TEDV-encoded CST in the 5' to 3' direction.
4) Represents a transcriptional terminator sequence for encoded CST in the 5' to 3' direction.
5) Represents the transcriptional terminator sequence for the 3' to 5' encoded GOI.
6) Represents the sequence encoding the GOI in the 3' to 5' direction.
7) Represents the Kozak sequence for efficient translational initiation of the GOI transcript.
8) Represents the 3' RMCE element FIG. 3. Tag-exchange receiver site (TERS) open architecture-before tag exchange A schematic representation of the TERS, depicted as a linear construct with each lettered box representing a key element of the construct architecture. The construct contains both the TERS-encoded CST, and the gene of interest (GOI).

a) Represents a Kozak sequence for efficient translational initiation of the adjoined transmembrane domain (TD)/CST transcript.
b) Represents an exon encoding a Type 2 membrane scaffold protein domain.
c) Represents an 5' intron splice donor site.
d) Represents the 5' RMCE element encoded in the non-coding and 'non-functional' 3' intron fragment, as equivalent, and paired with, the 5' RMCE element of the TEDV.
e) Represents functional sequences of the 3' intron fragment, containing a branch point sequence, a polypyrimidine tract and a 3' acceptor splice site.
f) Represents an exon encoding the TERS-encoded CST in the 5' to 3' direction.
g) Represents a transcriptional terminator sequence for encoded CST in the 5' to 3' direction.
h) Represents the transcriptional terminator sequence for the 3' to 5' encoded selection gene.
i) Represents the sequence encoding the selection gene in the 3' to 5' direction
j) Represents the Kozak sequence for efficient translational initiation of the selection gene transcript
k) Represents the 3' RMCE element
x) Represents the 5' genomic element responsible for regulating expression and tracking of the CST transcript. This genomic element minimally includes a promoter sequence that drives CST expression.
y) Represents the 5' genomic element responsible for regulating expression and tracking of the CST transcript. This genomic element minimally includes a promoter sequence that drives CST expression.

Figure 4:

FIG. 4. Exchanged TERS of the Derivative Engineered Cell

A schematic representation of TERS locus after RMCE-mediated exchange with TEDV-encoded elements. As depicted in FIG. 1, the elements encoded between the flanking RMCE sites of the TEDV are exchanged with the sequences of equivalent architecture encoded between the flanking RMCE sites of the TERS. This results in an exchanged TERS within the derivative engineered cell line. The lettered and numbered boxes represent the key genetic elements as detailed in FIG. 2 and FIG. 3, respectively.

Figure 5:
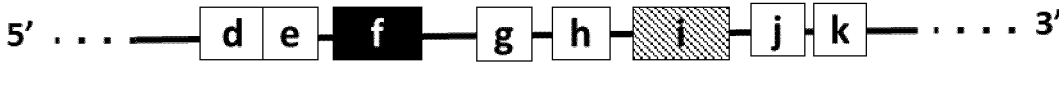

FIG. 5. Exchanged TEDV by-Product

A schematic representation of TEDV by-product after RMCE-mediated exchange with TERS-encoded elements. As depicted in FIG. 1, the elements encoded between the flanking RMCE sites of the TEDV are exchanged with the sequences of equivalent architecture encoded between the flanking RMCE sites of the TERS. This results in an unstable exchanged TEDV by-product during generation of the derivative engineered cell line. The lettered and numbered boxes represent the key genetic elements as detailed in FIG. 2 and FIG. 3, respectively.

Figure 6:
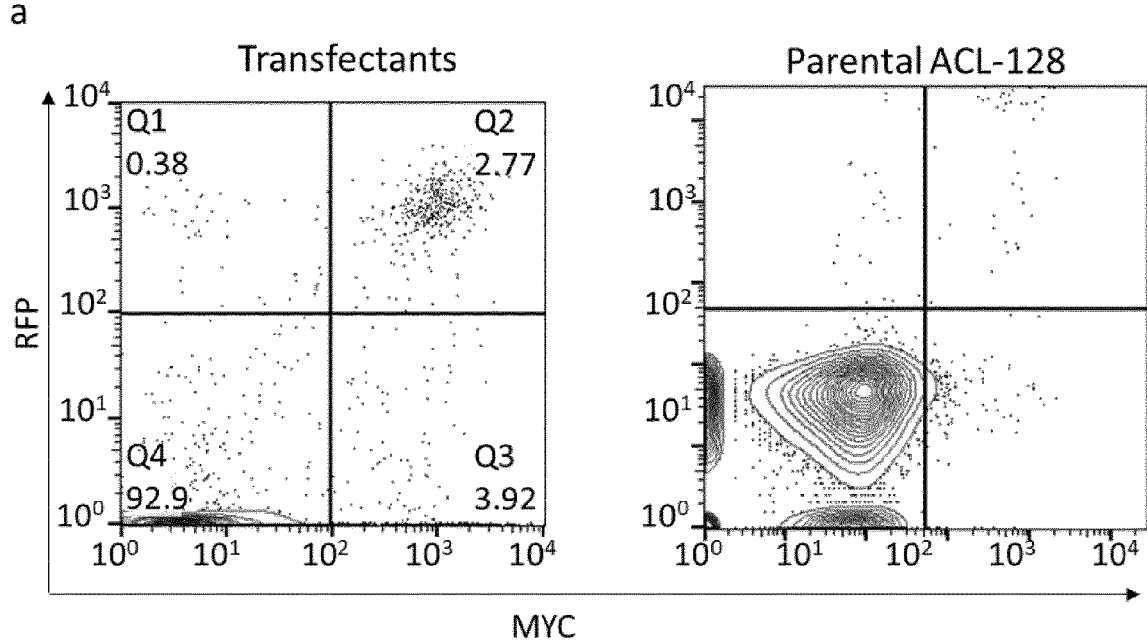
Figure 6:
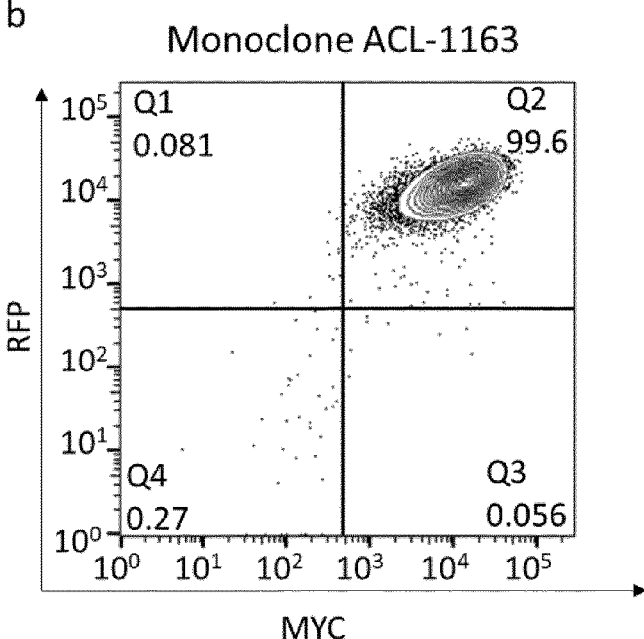

FIG. 6. Integration of TERS into engineered cells a) An engineered cell line population, ACL-1163, was created by integration of a TERS cassette encoding a Myc epitope CST and RFP selection gene, into a parental cell line ACL-128 by way of homology directed recombination. 10 days after electroporation, cells were stained with anti-Myc antibody and analysed by flow cytometry for selection markers encoded by TERS, the Myc epitope CST and RFP. The plot displays live single cells as RFP versus Myc, showing that among the transfected cells, there is a population of transfectants that display high signal for both RFP and Myc (Q2 left panel) compared to the parental cells (Q2 right panel). b) The cells with the high RFP and Myc signals were selected and outgrown and a representative engineered monoclone ACL-1163 analysed by flow cytometry. Plots display RFP versus Myc parameters of gated live single cells. The monoclone ACL-1163 has high RFP and Myc signals as expected (Q2).

Figure 7:
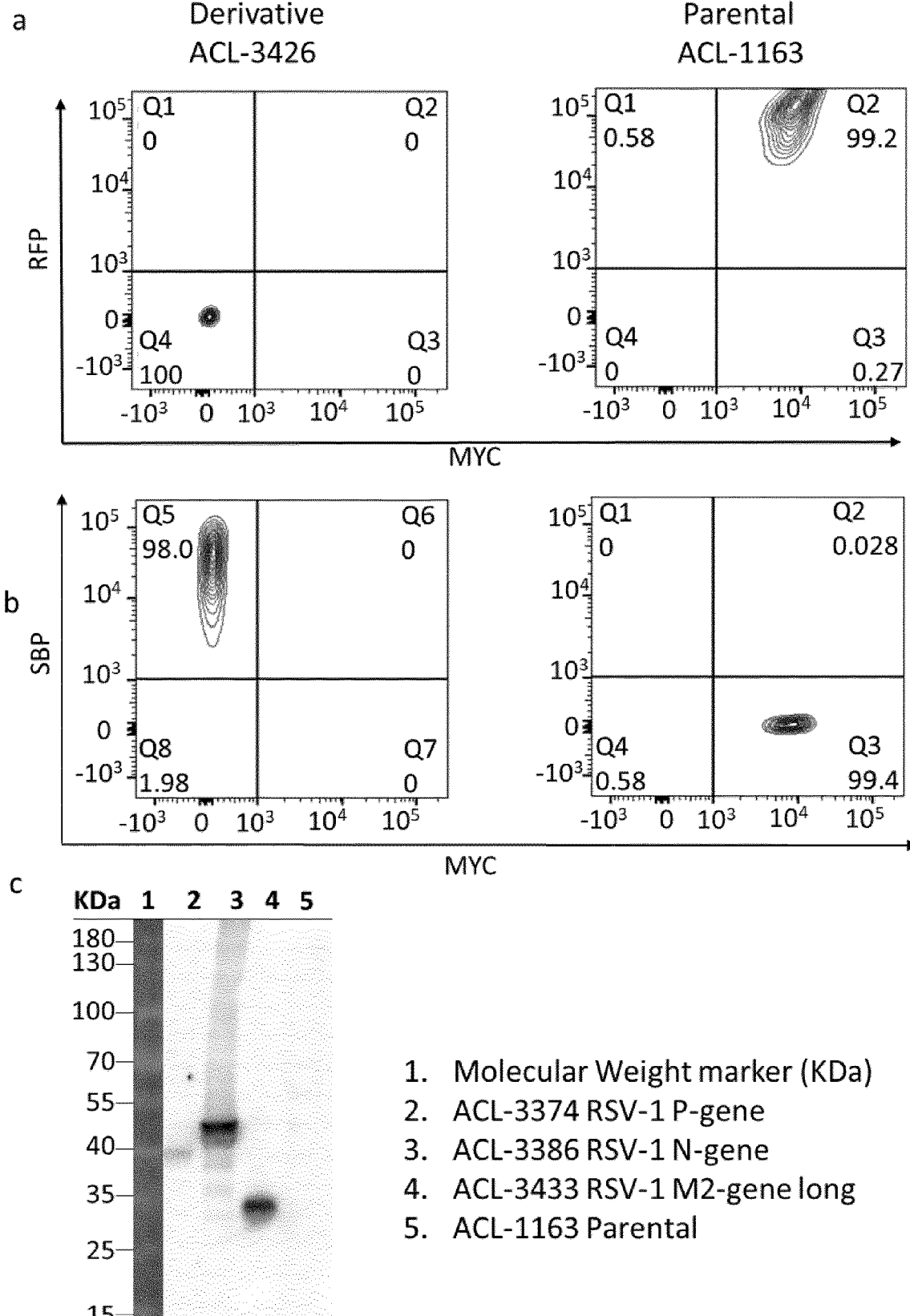

FIG. 7. Execution of an RMCE with TEDV with Tag-Exchange and Delivery of GOI to Generate Derivative Engineered Cells A Flp recombinase mediated tag-exchange was performed in the ACL-1163 engineered cells. ACL-1163 cells harbouring a TERS encoding an RFP selection gene and the Myc epitope CST, were transfected together with TEDV; encoding a SBP epitope CST and a GOI, together with a construct encoding a flp recombinase. 7 days after electroporation cells were stained with anti-Myc and anti-SBP antibodies and analysed by flow cytometry for RFP, Myc and SBP signals. Cells displaying reduced RFP and Myc signal but high signal for SBP surface expression were sorted and expanded as monoclones. a and b) Contour plots showing a representative derivative engineered cell monoclone ACL-3426 (left) compared to parental cells (right). Derivative cells show, loss of the RFP and the Myc signals (Q4 top left panel) compared to the parental cells (Q4 top right panel). The derivative engineered cell monoclone ACL-3426 successfully expresses the TEDV-encoded SBP epitope CST as shown by the increased signal when stained with the anti-SBP antibody (Q5 bottom right panel). These results suggest a successfully performed Flp recombinase mediated tag-exchange, as ACL-3426 cells have lost the signal for the RFP and Myc markers and gained SBP surface expression, as expected due to tag-exchange of the CSTs between the TERS and the TEDV. c) Immunoblot showing three examples of expression of an integrated GOI with C-terminal FLAG-tag. Detection of the GOI (RSV-1 ORFs) expression was achieved by immunoblotting using an antibody against Flag-tag. The parental monoclone line ACL-1163 is included for control. CSTE was performed in three independent experiments whereby cells were transfected with a construct encoding a flp recombinase and either with a TEDV encoding; a SBP epitope CST and a RSV-1 P gene (resulting cell line monoclone is ACL-3374); or TEDV encoding a SBP epitope CST and a RSV-1 N gene (resulting cell line monoclone is ACL-3386); or TEDV encoding a SBP epitope CST and RSV-1 M2 long gene (resulting cell line monoclone is ACL-3433). Protein was extracted from the monoclones, immunoblotting was performed using mouse anti-Flag antibody. The western blot results demonstrate that each RSV-1 ORF was expressed as evidenced by the presence of a single band in each corresponding cells corresponding to the expected molecular weight of each GOI, and absence of a signal in the parental cell line.

Figure 8:
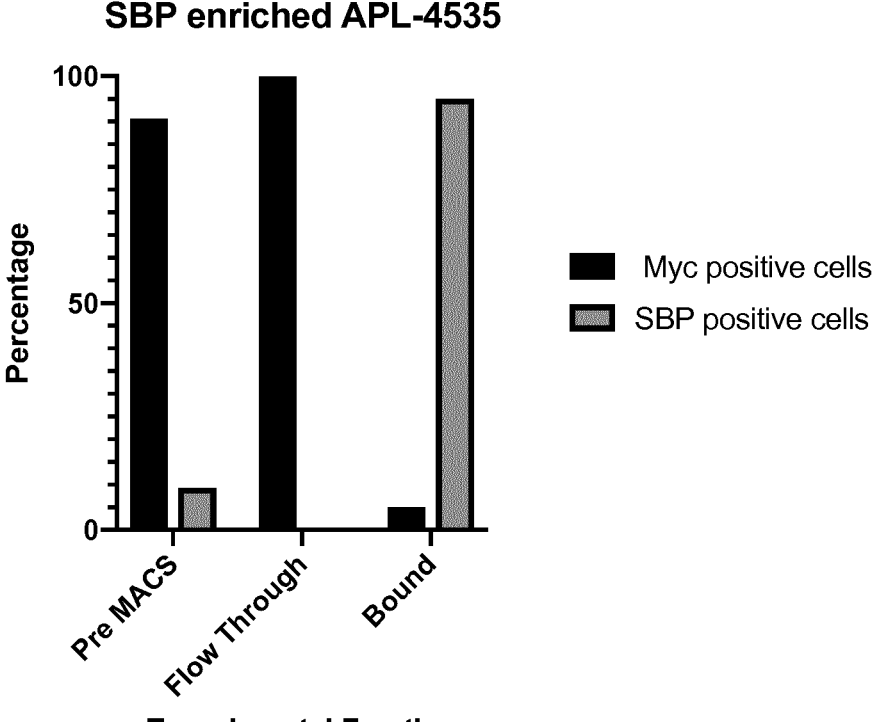
Figure 8:
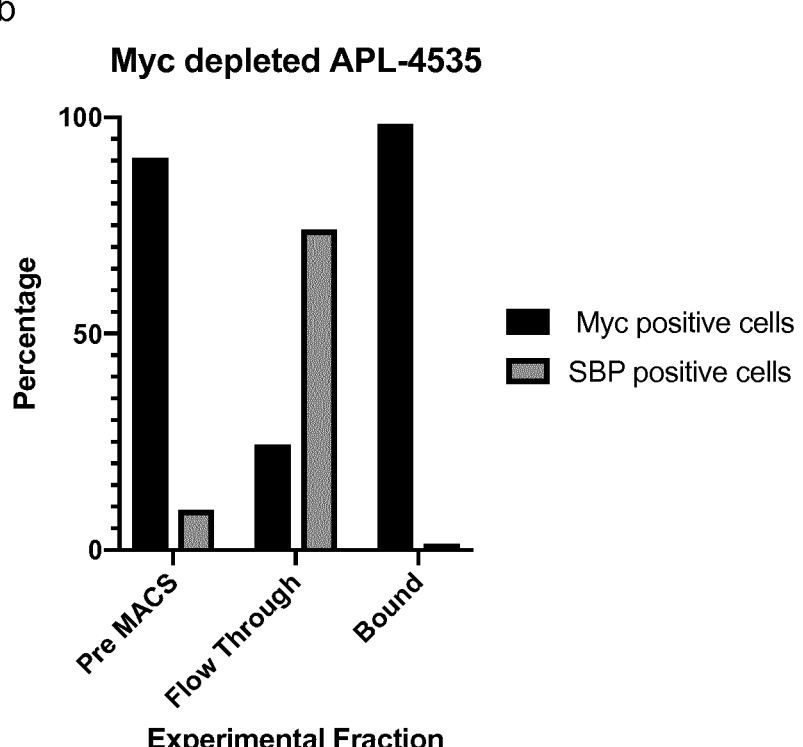
Figure 8:
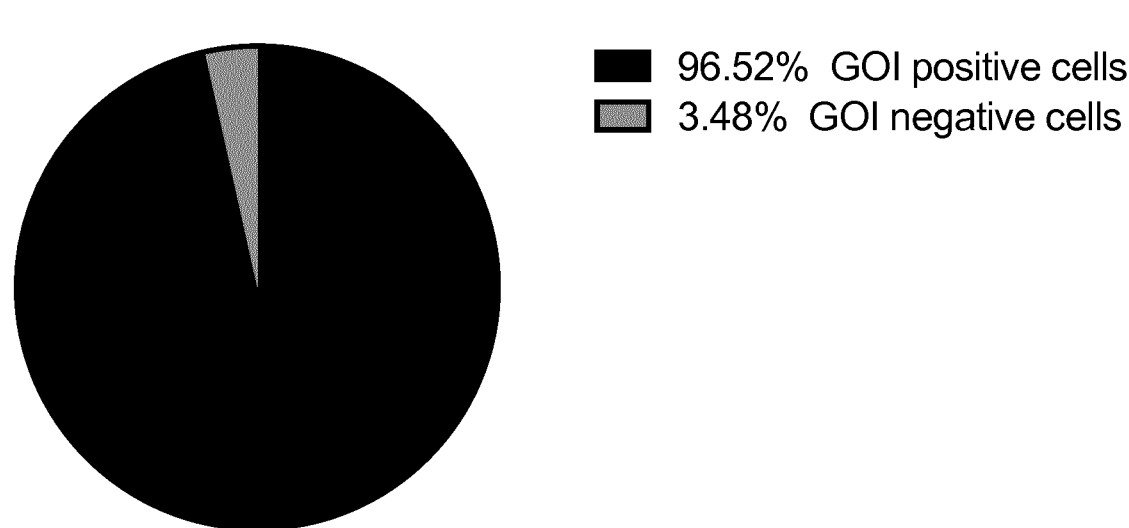

FIG. 8. Magnetic Affinity Cell Sorting (MACS) Enrichment of a Tag2 (SBP) or Depletion of Tag1 (Myc) from a Mixed Cell Population after a Successful Tag Exchange Event This figure demonstrates that the surface tag technology can be used for MACS enrichment of cells carrying Tag2 or depletion of cells carrying Tag1 after a successful tag exchange event from a mixed population of cells. A starting mixed population of two engineered monoclone cell lines, APL-4535 and APL-3015, was used to either enrich cells expressing the Tag2 (SBP) or deplete Tag1 (Myc) after a successful tag exchange event by using MACS. The TERS within the APL-4535 cells encoded an SBP epitope CST and full-length FLAG tag GOI encoding an intracellular protein; while the TERS within the APL-3015 cells encoded a Myc epitope CST and RFP selection gene. The two cell populations were mixed together at a percentage of 90% (APL-3015) to 10% (APL-4535) cells and MACS was used to either enrich the SBP positive cells (a) or in separate experiment deplete the Myc positive cells (b). a) All cells were labelled with anti-SBP-Alexa 488 fluorophore and incubated with anti-mouse IgG iron beads. The samples were passed through MACS and fractions were collected at three experimental time points-pre-enrichment, flow through and bound. All three fractions were counter stained with anti-c-Myc-Alexa 405 and data was acquired on the BD Influx instrument. The graph displays the percentage of SBP and Myc positive cells in all three experimental fractions. The pre-MACS fraction demonstrates that the starting population of cells consisted of 90% Myc positive cells and 10% SBP positive cells. The successful enrichment of SBP positive cells was demonstrated by the lack of SBP signal in the flow-through fraction (>0.01% SBP positive cells), while following the SBP targeted enrichment 95% of the bound cells were SBP positive. b) In a separate experiment, all cells were labelled with anti-c-Myc-Alexa 405 fluorophore and incubated with anti-mouse IgG iron beads. The labeled cells were depleted using MACS and fractions were collected at three experimental time points as indicated above. All three fractions were counter stained with anti-SBP-Alexa 488 and data was acquired on the BD Influx instrument. The graph displays the percentage of SBP and Myc positive cells after Myc targeted depletion in all three experimental fractions. The pre-MACS fraction again demonstrated that the starting population of cells consisted of 90% Myc positive cells and 10% SBP positive cells. The successful depletion of Myc positive cells was demonstrated by reduced number of Myc positive cells (25%) and increased number of SBP positive cells (75%) in the flow-through fraction. Furthermore, the bound fraction contained >90% Myc positive cells and <5% SBP positive cells. c) A total of 546 SBP positive staining individual monoclones was assessed whether they encoded the SBP-linked GOI. The chart shows that 96.52% of the SBP positive cells did integrate the GOI, while 3.48% of the SBP positive cells did not encode the GOI.

The results demonstrate that MACS can be used to either enrich Tag2 (SBP) positive cells or deplete Tag1 (Myc) positive cells from a mixed population of cells. Furthermore, the presence of the Tag2 (SBP) can be used as an indicator of a successful tag exchange and GOI genomic integration.

Figure 9:
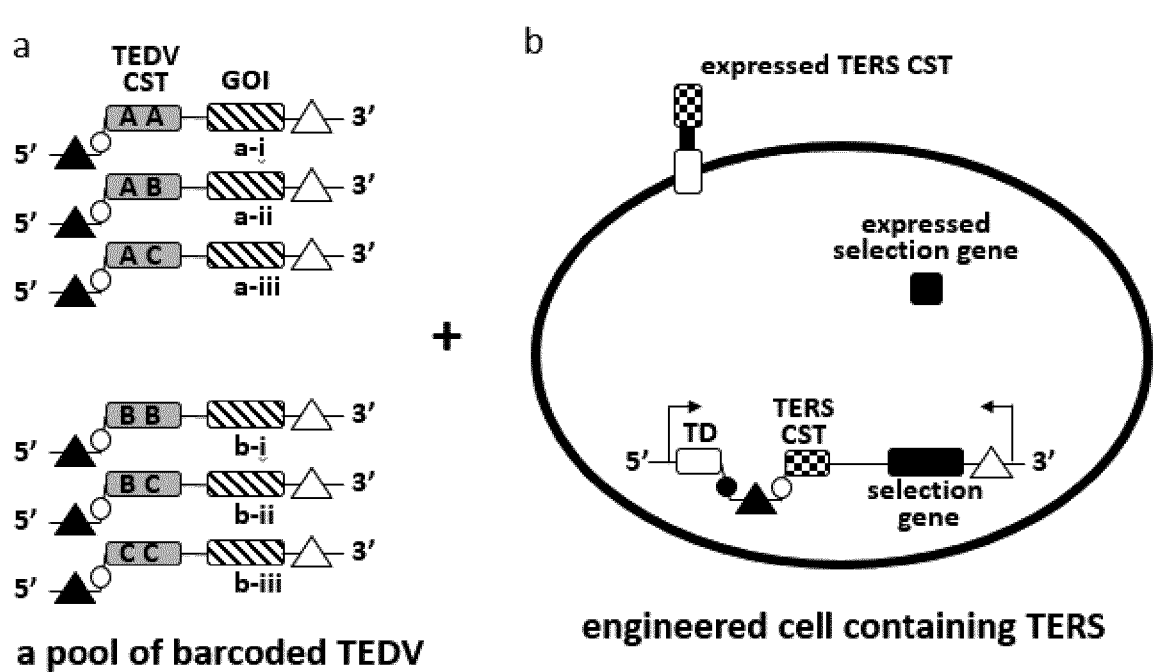
Figure 9:
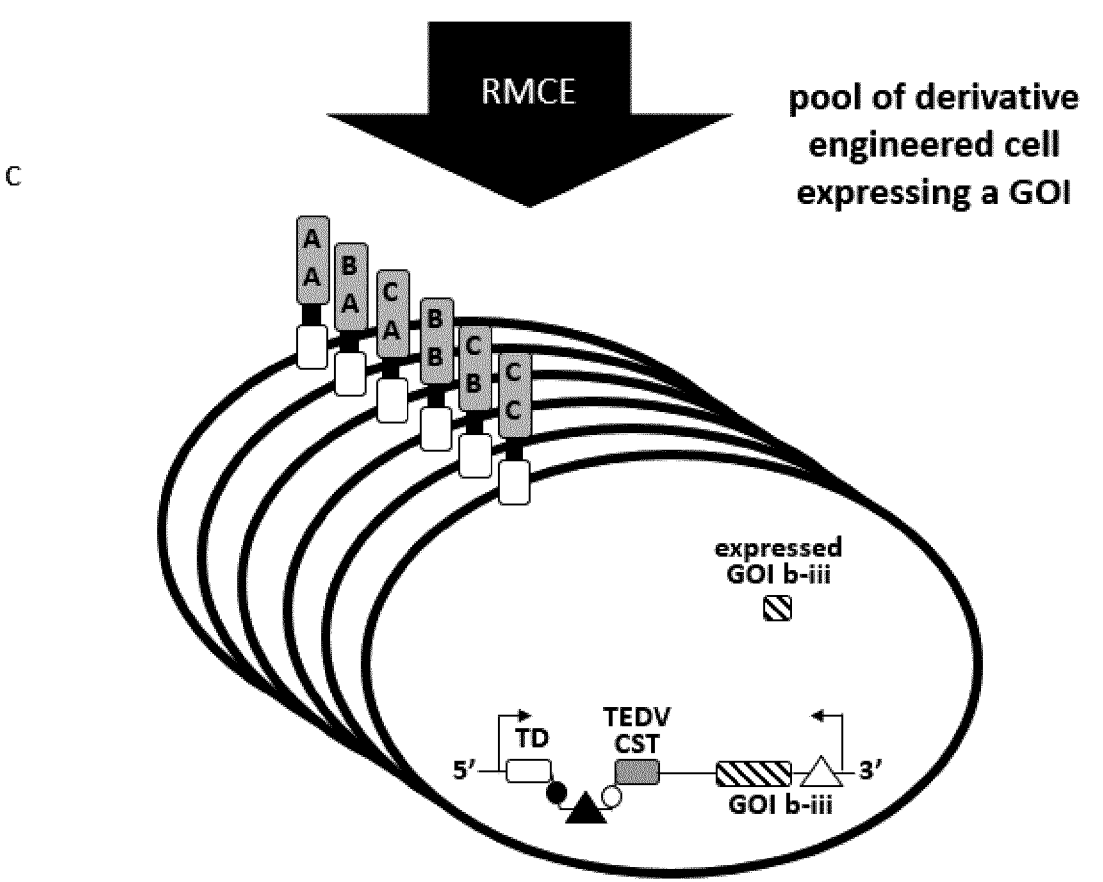
Figure 9:
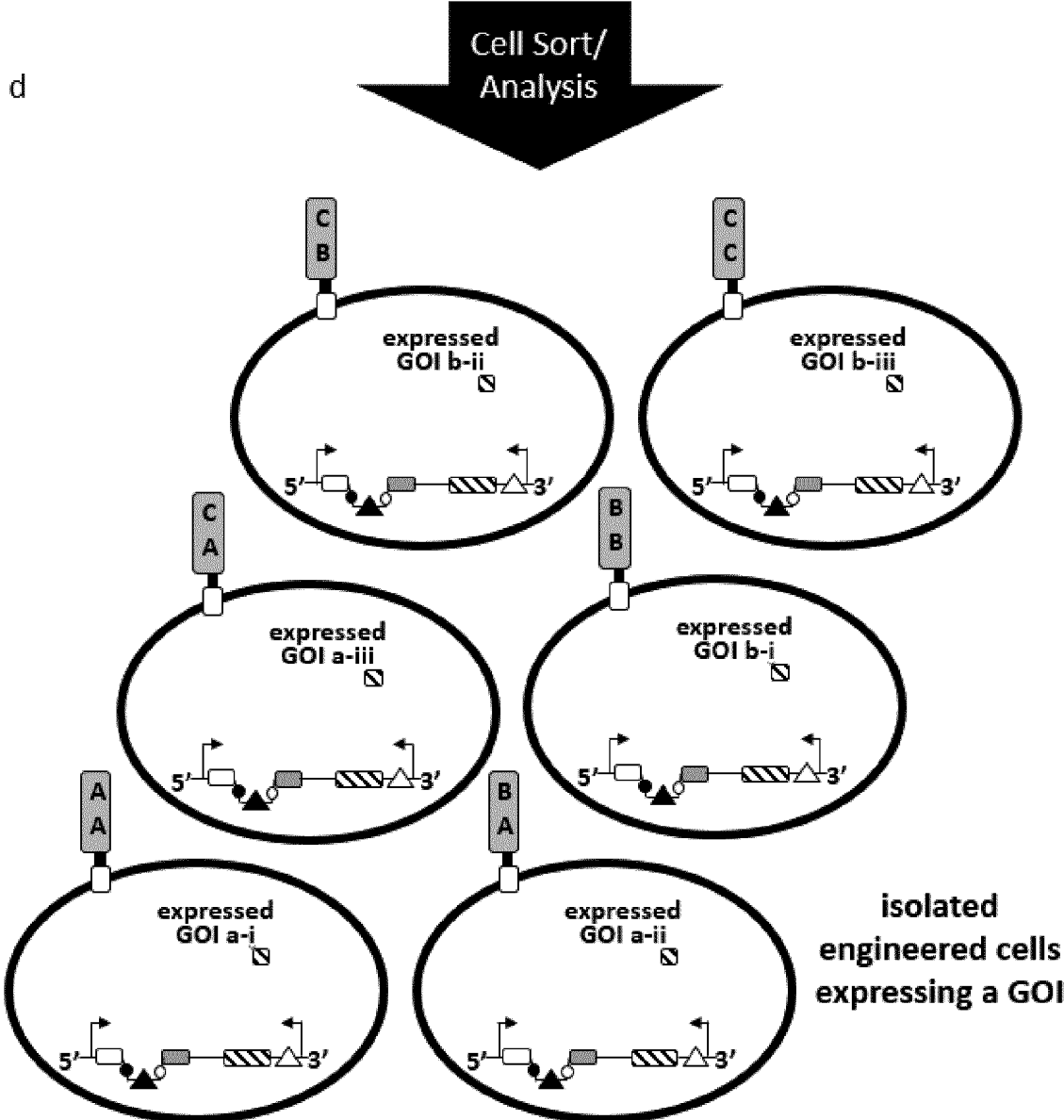

FIG. 9. Composition and Operation of the Cell Surface Tag Exchange (CSTE) System Using Barcodes Schematic representation of the CSTE system using barcoding. a) Depicts components of the Tag Exchange Donor Vector (TEDV). Each TEDV encodes RMCE elements at either terminus of the construct (open and closed triangles), which are paired with the RMCE sites contained within the TERS. The RMCE element at the 5' end of the TEDV construct (closed triangle) is encoded within a sequence that represents a 3' intron fragment, wherein immediately to the 3' of the RMCE element are the 3' elements of an intron (open circle), including a branch point sequence, polypyrimidine tracts and splice acceptor site. Immediately 3' of the splice acceptor site, the TEDV encodes a 3' exon of a cell surface tag (CST), meaning the exon encodes the portion of the CST containing unique molecular binding motifs (grey rectangle). The CST sequence is encoded in the 5' to 3' direction, where the TEDV also encodes the gene of interest (GOI) to be integrated to the TERS encoded in the 3' to 5' direction (cross-hatched rectangle).

Each CST in this example is composed of two different epitopes from a selection of 3 potential unique epitopes (A, B, C), which can be combined into 6 possible unique combinations. AB is effectively equivalent to BA. In this example, the AX combinations have been assigned to a GOI family, with three variants (GOI a-i, a-ii and a-iii), and the BX combinations have been assigned to a second GOI family with three variants (GOI b-i, b-ii, b-iii). The individual TEDV in this example are pooled. b) Depicts the components of the Tag Exchange Receiver Site (TERS). The TERS RMCE elements are paired with those of TEDV (open and closed triangles). The TERS encodes a CST exon distinct from that of the TEDV-encoded CST (chequered rectangle), with a splice acceptor site and associated 3' intronic sequence immediately to the 5' of this CST (open circle). Similarly, a selection gene (closed rectangle) is encoded in the antisense direction within the TERS, as is the GOI in the TEDV. At the 5' end of the construct, promoter sequences are included (rightward arrow), to drive transcription of the CST. To the 3' of this promoter sequence, a transmembrane domain (TD) exon is encoded (open rectangle), with a 5' intron sequence immediately to the 3' (closed circle). The TERS-encoded TD-CST product (open/chequered dumbbell) is expressed on the cell surface. At the 3' terminus of the TERS construct is a separate promoter element that drives transcription of the selection gene (closed rectangle) in the 3' to 5' direction, resulting in the expressed selection gene (closed square). c) Depicts the introduction of the TEDV pool to the engineered cell population containing the TERS, along with an appropriate expression construct for recombinase specific for the paired RMCE elements in the TEDV/TERS, resulting in the execution of RMCE, and the generation of a derivative engineered cell population expressing a variety of GOIs. During RMCE, the TERS-encoded elements exchange for the TEDV-encoded elements. The derivative cell population thus expresses the TEDV-encoded CST at the cell surface, as a TD-CST product with the originally TERS-encoded TD (open/grey dumbbell), and the GOI (crosshatched square). d) Following RMCE, the pool of engineered cells expressing GOI can be further isolated into its individual members via FACS, based on the expression of the unique CST barcodes. This can be achieved either as bulk populations of a desired barcode, or individual cell isolation via single cell sorting methods. Alternatively, analysis of the pool can be conducted via FAC without sorting using the barcode as means to identify populations of interest within the digital datasets.

e) As a proof of principle for using the CSTE system to barcode engineered cells, ACL-5 and ACL-1 cells were transfected, using chemical transfection (ACL-5) or electroporation (ACL-1) using standard methods known by those skilled in the art, with either a plasmid encoding a CST or a control plasmid without a CST. The CST comprised 3 unique epitopes, FLAG, MYC and HA (as represented by SEQ ID 20). 48 hours following the transfection, the cells were harvested and stained with the cognate antibodies conjugated with a fluorophore: anti-FLAG-PE, anti-MYC-AF647 and anti-HA-AF488. Cells were analysed by flow cytometry; live cells were gated by Forward Scatter (FSC) and Side Scatter (SSC). The Mean Fluorescence Intensity (MFI) of the live cells was determined for each of the 3 epitopes, and the percentage of live cells expressing the respective epitopes. All three epitopes were detected in high proportions and intensity in the cells transfected with the plasmid encoding the barcoded CST, compared to the empty vector, thereby demonstrating the ability of a CST to be composed of multiple epitopes.

The following list of non-limiting embodiments further illustrate the invention:

1. A combined system comprising two separate components, wherein the first component is a tag-exchange donor vector (TEDV) encoding a first cell surface tag (CST) exon flanked by a 3' intron fragment, and a gene of interest (GOI) in the antisense orientation, and the second component is an engineered cell containing within its genome a tag-exchange receiver site (TERS), encoding a second CST exon adjoined by a full intron sequence to an exon encoding a transmembrane domain, and also encoding a reporter gene in the antisense orientation, wherein paired recombinase mediated cassette exchange (RMCE) elements are included in the TEDV and TERS such that execution of RMCE between the TEDV and TERS results in exchange of the reporter element for the GOI encoded by the TEDV, and exchange of the first CST exon for the second CST exon, such that the derivative engineered cell now expresses the first CST and GOI, in place of the second CST and the reporter gene.

2. The combined system according to embodiment 1, wherein said first cell surface tag (CST) exon is different to said second CST.

3. The combined system according to any of embodiments 1-2, wherein the first component is a TEDV comprising
   a. a first RMCE element
   b. a 3' intron fragment
   c. a CST exon
   d. a first transcriptional terminator
   e. a second transcriptional terminator
   f. a GOI
   g. a Kozak sequence
   h. a second RMCE element
   wherein the CST exon and first transcriptional terminator are encoded in the antisense orientation from the GOI and associated transcriptional terminator and Kozak sequences.

4. The combined system according to any one of embodiments 1-3, wherein the first component is a TEDV comprising
   a. a first RMCE element-5'RMCE element encoded in the non-coding and 'non-functional' 3' intron fragment b. a 3' intron fragment, containing a branch point sequence, a polypyrimidine tract and a 3' acceptor splice site
   c. an exon comprising the TEDV-encoded CST in the 5' to 3' direction
   d. a first transcriptional terminator sequence for encoded CST in the 5' to 3' direction
   e. a second transcriptional terminator for the 3' to 5' encoded GOI
   f. a sequence encoding GOI in the 3' to 5' direction
   g. a Kozak sequence
   h. a 5' RMCE element
   wherein the CST exon and first transcriptional terminator are encoded in the antisense orientation from the GOI and associated transcriptional terminator and Kozak sequences.

5. The combined system according to any one of embodiments 1-3, wherein the first component is a TEDV containing
   a. a first RMCE element
   b. a 3' intron fragment
   c. a CST exon
   d. a first transcriptional terminator
   e. a second transcriptional terminator
   f. a GOI
   g. a Kozak sequence
   h. a second RMCE element
   wherein the CST exon and first transcriptional terminator are encoded in the antisense orientation from the GOI and associated transcriptional terminator and Kozak sequences.

6. The combined system according to any one of embodiments 1-5, wherein the second component is a TERS comprising
   a. a transcriptional promoter element
   b. a Kozak sequence
   c. a transmembrane domain exon
   d. an intron
   e. a first RMCE element
   f. a CST exon
   g. a first transcriptional terminator
   h. a second transcriptional terminator
   i. a reporter gene
   j. a Kozak sequence
   k. a second RMCE element
   l. a second transcriptional promoter element
   wherein the transmembrane domain exon and CST exon are encoded in the antisense orientation from the reporter gene, such that the first transcriptional promoter element drives transcription of the combined transmembrane domain and CST, and the second transcriptional promoter element drives transcription of the reporter gene.

7. The combined system according to any one of embodiments 1-6, wherein the second component is a TERS comprising
   a. a transcriptional promoter element
   b. a Kozak sequence
   c. a Type 2 membrane protein transmembrane domain exon
   d. a 5' intron splice donor site
   e. a 5' RMCE element encoded in the non-coding and 'non-functional' 3' intron fragment, as equivalent, and paired with, the 5' RMCE element of the TEDV
   f. functional sequences of the 3' intron fragment, containing a branch point sequence, a polypyrimidine tract and a 3' acceptor splice site g. an exon comprising the TERS-encoded CST in the 5' to 3' direction (that is different to the TEDV-encoded CST)

h. a transcriptional terminator sequence for encoded CST in the 5' to 3' direction i. a transcriptional terminator sequence for the 3' to 5' direction j. a sequence encoding the selection gene in the 3' to 5' direction k. a Kozak sequence for efficient translational initiation of the selection gene transcript l. a 3' RMCE element m. a 3' genomic element responsible for regulating expression and tracking of the CST transcript, Per reaction, $4\times10^6$ cells were electroporated in 500 ul RPMI 1640 with Glutamax-I (Life Technologies) using the Gene Pulser Xcell™ (Bio-Rad) with the following setting Square Wave 285V, pulse length 12.5 ms and 2 pulses with 1 s interval. The DNA concentrations used were 15 ug/ul for the TERS integration vector (V9.F.5), 10 ug/ml for the Cas9-P2A-GFP encoding plasmid (V1.A.8) and 7.5 ug/ml for the vector encoding the gRNA targeting the integration site AAVS1 site (V2.J.6) (Table 1).

After electroporation, cells were incubated in culture medium RPMI 1640 with Glutamax-I+10% FBS (37° C., 5% $CO_2$) for two days, before analysis.

Sorting of Polyclonal GFP-Expressing Transfectant Cells

Cells electroporated with Cas9-P2A-GFP (V1.A.8) or with a plasmid encoding a GFP

TABLE 1

| Vectors | |
| --- | --- |
| ID | Name |
| V1.A.8 | SpCas9-2A-GFP |
| V9.F.5 | AAVS-EF1aL-TxnCS-S-STv5a_G-in:FRT:MYC-RFP:F3-EF1a |
| V2.J.6 | AAVSI_sg-sp-opti_3 |
| V12.A.8 | M2-gene-Long_RSV1-FLAG_Tx |
| V4.I.8 | CMVpro_FLPo-sv40pA-V2 | wherein the transmembrane domain exon and CST exon are encoded in the antisense orientation from the reporter gene, such that the first transcriptional promoter element drives transcription of the combined transmembrane domain and CST, and the second transcriptional promoter element drives transcription of the reporter gene.

8. The combined system according to any one of embodiments 1-6, wherein the second component is a TERS containing a. a transcriptional promoter element 21. The engineered cell according to embodiment 20 wherein said TERS comprises:

a. a transcriptional promoter element b. a Kozak sequence c. a transmembrane domain exon d. an intron e. a first RMCE element f. a CST exon g. a first transcriptional terminator h. a second transcriptional terminator i. a reporter gene j. a Kozak sequence k. a second RMCE element l. a second transcriptional promoter element, wherein the transmembrane domain exon and CST exon are encoded in the antisense orientation from the reporter gene, such that the first transcriptional promoter element drives transcription of the combined transmembrane domain and CST, and the second transcriptional promoter element drives transcription of the reporter gene.

GFP and RFP fluorescence was detected on the Influx™ (BD Biosciences) FACS to the filter set listed in Table 2. Single cells expressing Myc and RFP were sorted into 96-well plates, containing 200 ul of growth medium to grow a collection of monoclones.

TABLE 2

| FACSJazz and Influx filters | | | |
| --- | --- | --- | --- |
| Protein | Fluorochrome | Excitation laser | Detection Filter |
| Cas9/GFP | GFP | 488 | 530/40 |
| RFP | RFP | 561 | 585/29 |
| Myc | Alexa647 | 640 | 670/30 |
| Myc | PE | 561 | 585/29 |
| SBP | Alexa647 | 640 | 670/30 |
| SBP | Alexa488 | 488 | 530/40 |
| Myc | Alexa405 | 405 | 460/50 |
| Flag | PE | 561 | 585/29 |
| HA | Alexa488 | 488 | 530/40 |

Phenotypic Screening of Monoclonal Populations

A sample of 20,000 cells of the outgrown monoclone population was transferred into microtiter plates for analysis, cells were resuspended in 250 ul of DPBS 1× (Life Technologies) and analyzed on the LRSFortessa™ (BD Biosciences). The monoclonal population (ACL-1163) was screened for the presence of the Myc epitope CST and RFP. Myc expression was detected using the anti-Myc antibody labelled with the Alexa Fluor 647 fluorophore. Staining solution was prepared using the recommended antibody volume diluted in 100 ul of staining buffer (DPBS+2% FBS). Cells were incubated for 1 hour at 4° C. and then washed twice with 500 ul of staining buffer, prior to analysis.

Genotypic Screening of Monoclones-Confirmation of Integration in Correct Genomic Location ACL-1163 cells were maintained in normal growth medium of RPMI 1640 with Glutamax-I+10% HI-FBS. The confluence of cells was monitored every day, until they reached $10\text{-}12\times10^6$. DNA was extracted from $5\times10^6$ cells using the QIAamp DNA Minikit (Qiagen). The remaining Materials and Methods Integration of TERS to an Engineered Cell Line Electroporation was used to deliver the required DNA constructs to generate engineered cells with a single TERS site integrated into the AAVS1 site by way of homology directed recombination.

cells were further expanded and cryopreserved at a density of $3\times10^6$ cells/ml, in 70% growth medium+20% HI-FBS+10% DMSO.

ACL-1163 monoclones were screened and assessed at a molecular level, this was done by PCR using Q5® Hot Start High-Fidelity DNA Polymerase (NEB), in 20 ul reactions, using the components and reaction conditions listed in tables 3 and 4, respectively. To determine whether TERS integration cassette integrated into the AACS1 locus, primers 15.F.9 and 19.E.7 were used (Table 5), that target respectively, the region before the left homology arm and the transmembrane domain. Correct left homologous arm recombination was indicated by 2.1 kb amplicons. Initially, a PCR Master Mix was prepared with all components (Q5® Reaction Buffer, dNTPs, Hot-Start Q5R DNA polymerase, primers Fwd and Rev, 100 ng of DNA template and $H_2O$). PCR reactions were run using C1000 Touch™ Thermal Cycler (Bio-Rad). PCR products were run on a 1% Agarose gel in 1×TAE buffer, using the PowerPac Basic (Bio-Rad), stained with 10,000 dilution of sybersafe and analyzed with Fusion SL (Vilber Lourmat).

TABLE 3

PCR reagents for assessing integration of the TERS

| Reaction Component | Volume per reaction |
| --- | --- |
| 5xPhusion buffer | 4 ul |
| DNTPs | 0.2 ul |
| Phusion DNA polymerase | 0.15 ul |
| 15.F.9 | 0.5 ul |
| 19.E.7 | 0.5 ul |
| H20 | up to 20 ul |
| DNA (100 ng) | 1 ul (100 ng/ul) |
| DMSO 3% | 0.6 ul |

TABLE 4

PCR cycle conditions

| Step | Temperature | Time |
| --- | --- | --- |
| Initial Denaturation | 98° C. | 30 sec |
| 30 cycles | 98° C. | 10 sec |
| | 62° C. | 1:10 min |
| | 72° C. | 15 sec |
| Final extension | 72° C. | 10 min |

TABLE 5

Primers

| ID | Name | Sequence |
| --- | --- | --- |
| 1.I.7 | turboRFP_GT_F1 | GAGAGGCCATTCTCAGATGG (SEQ ID NO: 12) |
| 1.I.8 | turboRFP_GT_R1 | CGGGCATCTTCAGGTTCTTG (SEQ ID NO: 13) |
| 1.I.9 | turboRFP_probe_FAM | CTACCTGCACTGCTCCTTCAAGACC (SEQ ID NO: 14) |
| 10.A.10 | TRAC_TCRA-promoter_F1 | CTGATCCTCTTGTCCCACAGATA (SEQ ID NO: 17) |
| 10.B.6 | TRAC_probe (HEX) | ATCCAGAACCCTGACCCTGCCG (SEQ ID NO: 16) |
| 15.F.9 | AAVS1_GT_F5 | ACTCTGCCCTCTAACGCTG (SEQ ID NO: 18) |

TABLE 5-continued

Primers

| ID | Name | Sequence |
| --- | --- | --- |
| 19.E.7 | AMPN-TMD_GT_R1 | GCTGATGTAGAAGCCCTTGG (SEQ ID NO: 19) |
| 21.G.5 | ORF-AM_GT_F2 | TTCTGTAGCTCCATTGGCAG (SEQ ID NO: 21) |
| 21.G.8 | ORF-AM_GT_R1 | ATCCGTATGGTGACAAGACG (SEQ ID NO: 22) |

Identification of Gene Copy Number

DNA of selected monoclones was evaluated for a number of TERS cassettes integrated within the cells genome. To achieve this, Droplet Digital PCR (ddPCR) was performed using primer and probes specific to the TERS cassettes and a reference gene (TRAC) (Table 6). The TERS specific probe was conjugated with FAM, and the reference gene specific probe conjugated with HEX. Integration copy number considered that the ACL-1163 cells are diploid for the reference gene (TRAC). Prior to ddPCR, DNA was digested with Mfel (NEB) to separate tandem integrations. The reaction setup and cycling conditions were followed according to the protocol for ddPCR™ Supermix for Probes (No dUTP) (Bio-Rad), using the QX200™ Droplet Reader and Droplet Generator and the C1000 Touch™ deep-well Thermal cycler (Bio-Rad). Data was acquired using the QuantaSoft™ Software, using Ch1 to detect FAM and Ch2 for HEX.

TABLE 6 ddPCR Primers/probes

| ID | Name | Sequence |
| --- | --- | --- |
| 1.I.7 | turboRFP_GT_F1 | GAGAGGCCATTCTCAGATGG (SEQ ID NO: 12) |
| 1.I.8 | turboRFP_GT_R1 | CGGGCATCTTCAGGTTCTTG (SEQ ID NO: 13) |
| 1.I.9 | turboRFP_probe_FAM | CTACCTGCACTGCTCCTTCAAGACC (SEQ ID NO: 14) |
| 10.A.9 | TRAC-TCRA-ex1-F1 | CTGATCCTCTTGTCCCACAGATA (SEQ ID NO: 17) |
| 10.A.10 | TRAC-TCRA-ex1-F1 | GACTTGTCACTGGATTTAGAGTCT CT (SEQ ID NO: 15, 23) |
| 10.B.6 | TRAC-probe (HEX) | ATCCAGAACCCTGACCCTGCCG (SEQ ID NO: 16) |

Flp-Mediated Integration of GOI Sequences in Derivative Engineered Cell Line

Electroporation was used to deliver the required DNA constructs to promote Flp recombinase mediated tag exchange. Per reaction, $4\times10^6$ cells were electroporated in 500 ul RPMI 1640 with Glutamax-I (Life Technologies) using the Gene Pulser Xcell™ (Bio-Rad) with the following setting: Square Wave 285V, pulse length 12.5 ms and 2 pulses with 1 s interval. The DNA concentrations used were 7.5 μg/ml for the TEDV vector (V9.F.5), 10 ug/ml for the FLPO encoding plasmid (V12.A.8) and 7.5 ug/ml for the vector encoding GFP for tracing DNA delivery (V1.A.4) (Table 1).

After electroporation, cells were incubated in culture medium RPMI 1640 with Glutamax-I+10% FBS (37° C., 5% $CO_2$) for two days, before analysis and cell sorting of GFP positive cells.

Phenotyping for Tag Exchange

To determine if Flp recombinase mediated tag exchange occurred, cells were stained for surface expression of Myc and SBP and measured for RFP fluorescence intensity. 7-10 days after electroporation, the cells were harvested, and surface stained for SBP and Myc using the following antibodies (anti-SBP-Alexa647 and anti-c-Myc-AlexaPE, SantaCruz). GFP and RFP fluorescence was detected on the Influx™ (BD Biosciences) FACS to the filter set listed in Table 2.

Single cells expressing SBP but not Myc and RFP were sorted into 96-well plates, containing 200 ul of growth medium to grow a collection of monoclones.

Phenotyping of monoclones was performed 20-24 days post single cell sort. For flow cytometric analysis, the cells were transferred from the wells and 300 ul RPMI was added per tube. Cells were centrifuged for 3 min at 400 g, at 4° C., Supernatant was aspirated and cell pellets were resuspended in 25 ul stain mix or RPMI (unstained controls) (Stain mix: anti-SBP-Alexa647 and anti-c-Myc-AlexaPE) and incubated for 30 min at 4° C. Cells were washed twice with staining buffer (SB) (DBPS+2% FBS) and centrifuged for 3 min at 400 g. Cells were resuspended in 200 ul of SB and transferred to 96-well plates for data acquisition on LSR-Fortessa. Analysis was performed using FlowJo.

Confirmation of GOI Expression

Cells were grown and following harvest the cells were lysed with 150 mM NaCl, 50 mM Tris pH 8, 1% CHAPS, 5 mM Imidazole, 1 mM PMSF, 1× protease and phosphatase inhibitors (Thermo) for 20 minutes on a rotor at 4° C. Lysates were cleared by centrifugation at 17000 g for 10 minutes at 4° C. and subjected to sodium Dodecyl Sulphate (SDS) gel electrophoresis on 10% acrylamide pre-cast gel (Biorad) at 140V for 1 hour. Gels were turbo blotted onto PVDF membranes (Biorad), which were then blocked for 15 minutes in Sea block 1× (Thermo) in Tris buffered saline/tween 20 (TBST) 1× and incubated with mouse anti-flag antibody (Sigma) for 2 hours at room temperature. Membranes were washed from unbound primary antibody 3× for 5 minutes in TBST 1× and incubated with anti-mouse horseradish peroxidase (HRP)-conjugated goat antibody for 1 hour at room temperature. Membranes were finally washed from unbound secondary antibody 3× for 5 minutes in TBST 1× and finally, the HRP signal was developed with ECL substrate (Biorad) and acquired with Fusion SL Vilber system.

Confirmation of GOI Genomic Integration

Monoclone cell lines expressing cell surface Tag 2 (SBP) were assessed at a molecular level for the cointegration of a GOI coding sequence. This was done by PCR using Q5® Hot Start High-Fidelity DNA Polymerase (NEB), in 30 ul reactions, using the components and reaction conditions listed in tables 7 and 8, respectively. To determine whether a GOI integrated into the genome, primers 12.G.5 and 21.G.8 were used (Table 5), that target the 3'UTR region of the GOI. Initially, a PCR Master Mix was prepared with all components (Q5® Reaction Buffer, dNTPs, Hot-Start Q5® DNA polymerase, primers Fwd and Rev, 100 ng of DNA template and $H_2$0). PCR reactions were run using C1000 Touch™ Thermal Cycler (Bio-Rad). PCR products were run on a 1% Agarose gel in 1×TAE buffer, using the PowerPac Basic (Bio-Rad), stained with 10,000 dilution of sybersafe and analyzed with Fusion SL (Vilber Lourmat). A band of correct size was confirmed to encode sequence of the GOI 3'UTR by sanger sequence.

TABLE 7

| PCR mix | | |
|---|---|---|
| Reagent | Per/reaction (μL) | Master mix for 96 samples |
| 5XPhusion HF buffer | 6 | 660 |
| DNTPs | 0.3 | 33 |
| Phusion Hot Star pol | 0.3 | 33 |
| 21.G.5 ORF-AM_GT_F2 (100 μM) stock | 0.15 | 55 |
| 21.G.8 ORF-AM_GT-R1 (100 μM) stock | 0.15 | 55 |
| H20 | 20.4 | 2244 |
| Cell sample | 2 | NA |

TABLE 8

| PCR conditions | | | |
|---|---|---|---|
| Step | Temprature | Time | Number of cycles |
| Initial Denaturation | 98° C. | 30 sec | 1 |
| Denaturation | 98° C. | 10 sec | 35 |
| Annealing | 62° C. | 20 sec | |
| Extension | 72° C. | 10 sec | |
| Finial Extension | 72° C. | 5 min | 1 |
| Hold | 12° C. | hold | 1 |

MACS Enrichment/Depletion of Surface Tag Expressing Cells

The manufacturer's MACS protocol for enrichment/depletion was generally followed (Miltenyi Biotec, #130-047-101, IM0001377.PDF).

Sample Preparation

Cells were harvested and washed once by centrifugation (300×g at 4° C. for 3 min) in stain buffer-M (SB-M—cold Dulbecco's phosphate buffered saline (DPBS), 2% FBS, 2 mM EDTA). SB-M resuspended cells were filtered through a 40-μm cell strainer to obtain single cell suspension. Cells were washed with 3 ml cold SB-M and cell pellet was collected. 80 μl staining solution, containing appropriate antibodies or dead cell removal reagent, was used per 10 million cells and the sample was incubated at 4° C. for 30 min. Cells were washed twice with 3 ml SB-M buffer and pelleted.

Magnetic Bead Labelling

The pelleted cells were labelled with magnetic beads by resuspension of the cells in 160 μl SB-M and addition of anti-mouse IgG1 MACS MicroBeads (Miltenyi) (40 μl MACS MicroBeads were added per 10 million cells). After incubation at 4° C. for 20 min, cells were washed with 3 ml SB-M and finally resuspended in 500 ul SB-M.

Magnetic Separation

A LS column (Miltenyi) was placed in the magnetic field of a suitable MACS separator (Miltenyi) and rinsed with 3 ml SB-M. A pre MACS fraction was also collected. Cell suspension was added to the column and flow-through fraction containing unlabelled cells was collected into a 15 ml conical tube (this is referred to as the flow-through fraction). The column was removed from the separator and placed in a suitable collection tube. 5 ml SB-M was added into the column containing the magnetically labelled cells.

Using the supplied plunger, pressure was applied until the plunger reached the bottom of the column. The magnetically labelled cells were eluted from the column (this is referred to as the bound fraction) and the fraction was used in downstream applications.

Example 1—Integration of TERS into an Engineered Cell Line

This example describes the stable integration of a TERS into a cell line to produce an engineered cell line monoclone ACL-1163 containing a single TERS in the genome.

In this example, the TERS presented as SEQ ID 1, comprised of the following selected genetic elements that encode two genes. The first gene encoded in the sense direction, comprises of a EF1a promoter upstream of an ORF encoded across two exons. The first exon encodes a Transmembrane Type II protein domain (TD) and the second encodes the Myc epitope tag. The intron between the two exons was derived from the human GAPDH gene, and modified to encode the first heterospecific FRT site (FRT) between the 5' intron splice donor site and intron branch point sequence. 3' end of the ORF encodes a SV40 poly-adenylation signal terminator. The second gene encoded in the antisense direction comprises of a EF1a promoter upstream of an ORF encoding the fluorescent reporter, RFP. The region between the Kozak sequence and the promoter encodes the second heterospecific FRT site (F3). 3' end of the RFP ORF encodes a bGHpA polyadenylation signal terminator.

To promote the stable genomic integration of the TERS into the genomic safe harbor locus, AAVS1, a plasmid was constructed, wherein; the DNA elements of the TERS were flanked with AAVS1 left and right homology arms. Each arm comprised of >500 bp of sequence homologous to the AAVS1 genomic locus. Stable integration of TERS was achieved through the process of homology directed recombination (HDR) at the genomic safe harbor locus, AAVS1.

The ACL-128 cell line was transfected with a plasmid that encoded the TERS genetic elements flanked by AAVS1 left and right homology arms, a plasmid that encoded an optimal gRNAs targeting the AAVS1 locus, and a plasmid that encoded Cas9-P2A-GFP. Cells positive for Cas9-P2A-GFP plasmid uptake were FACS sorted based on GFP fluorescence, 2 days after. The GFP sorted cells were further expanded for greater than 7 days. The TERS-transfected cells were stained with an anti-Myc antibody and analyzed by flow cytometry for presence of RFP and Myc epitope CST (FIG. 6a). The cells that have integrated the TERS into their genome showed increased RFP and Myc signals. These cells were sorted and expanded to represent a collection of monoclones. A representative monoclone, ACL-1163 shown in FIG. 6b, demonstrated constant and strong expression of RFP and Myc surface expression. To determine that the genomic receiver cassette integrated into the targeted AAVS1 site, genomic DNA was extracted from the selected ACL-1163 cell line and a PCR reaction was performed with a primer internal to the TERS receiving cassette and a primer specific to the AAVS1 locus (15.F.9 and 19.E.7, see Table 5). A PCR amplicon of expected size was detected (data not shown). Furthermore, ddPCR with the primers and probe (forward primer 1.I.7, reverse primer 1.I.8, probe 1.I.9, see Table 6) confirmed that only a single copy of the TERS receiving cassette was integrated (data not shown).

The resulting engineered cell line, ACL-1163, contained a single copy of the TERS designed for RMCE with suitable paired TEDV.

Example 2—Execution of an RMCE with TEDV with Tag-Exchange and Delivery of GOI to Generate Derivative Engineered Cells This example demonstrates execution of the CSTE system that is the RMCE driven reaction between TEDV-encoded sequences and TERS results in a switch of CSTs, on the cell surface, thus reporting the exchanged construct incorporating TEDV-encoded sequences and the cargo GOI. In the present example, the above described ACL-1163 was used as the target engineered cell line.

The TEDV in the current example, encodes in the sense direction the first heterospecific FRT site (FRT), a 3' intron fragment, containing a branch point sequence, a polypyrimidine track and a 3' acceptor splice site; an exon encoding streptavidin binding peptide (SBP) and a SV40 polyadenylation signal terminator. Three separate GOI, originating from the respiratory syncytial virus (RSV), were encoded in the antisense direction in separate TEDV, each GOI ORF located between the second heterospecific FRT site (F3) and 3' bGHpA polyadenylation signal terminator. The sequences SEQ ID 3-SEQ ID 5 represent the three independent SBP epitope CST and GOI encoding TEDV constructs used.

In the present example, the engineered cell line, ACL-1163 constructed in example 1 was electroporated with a TEDV (selected from sequences SEQ ID 3-SEQ ID 5) and with a vector encoding expression of the RMCE recombinase enzyme (FLPO, V4.1.8, Table 1, SEQ ID 2). Cells were incubated for 7-10 days to allow for the integration couple to occur and then were stained with anti-Myc and anti-SBP antibodies and analyzed by flow cytometry for RFP, Myc and SBP reporter signals. Cells displaying reduced RFP and Myc signals but increased SBP signal, indicating a 'tag exchange', were sorted and expanded to represent a collection of monoclones. Characterization of a representative monoclone, ACL-3426, is depicted in FIGS. 7a and 7b. To confirm a successful surface tag exchange, the monoclone ACL-3426 was stained with an antibody against Myc and an antibody against SBP and analyzed by flow cytometry for the loss of RFP and Surface Myc expression (FIG. 7a) and gain of SBP signal (FIG. 7b). Indeed, the cells that performed the CSTE showed successful tag-exchange by displaying SBP and not Myc or RFP signals. Parental cells were analysed in parallel and showed persistent high signal for both RFP and Myc (FIG. 7a right panel) and a low SBP signal (FIG. 7b right panel).

To demonstrate that following CSTE, the GOI ORF integrated and is being expressed, three monoclones from independent experiments using each of the TEDV described above, encoding distinct RSV-1 GOIs were assessed by immunoblot (FIG. 7c). The GOI ORFs each encoding a Flag-tag, donated by the TEDVs were 3 genes from the RSV-1; P, N genes and M2 gene (long). CSTE was performed whereby the cells were transfected with a construct encoding a flp recombinase and either with TEDV; a SBP epitope CST and a RSV-1 P gene (resulting cell line monoclone is ACL-3374); or TEDV encoding a SBP epitope CST and a RSV-1 N gene (resulting cell line monoclone is ACL-3386); or TEDV encoding a SBP epitope CST and RSV-1 M2 long gene (resulting cell line monoclone is ACL-3433). Protein was extracted from the monoclones, and the samples were immunoblotted using mouse anti-Flag primary antibody, followed by an incubation with an anti-mouse horseradish peroxidase (HRP)-conjugated goat anti-body. The HRP signal was developed with ECL substrate. A successful CSTE was demonstrated by the presence of a single band positive for flag of expected molecular weight for each of the GOI (FIG. 7c lanes 2-4). Parental cells were analyzed in parallel and showed absence of the Flag-tag signal (FIG. 7c lane 5).

In summary, this example demonstrates that the cell surface tag-exchange can be used to conditionally report the presence of the initial TERS construct, and the exchanged construct incorporating TEDV-encoded sequences upon execution of RMCE, and report GOI integration and expression independently of detection of the GOI itself.

Example 3—Magnetic Affinity Cell Sorting (MACS) Enrichment of a Tag2 (SBP) or a Depletion of Tag1 (Myc) from a Mixed Engineered Cell Population after a Successful Tag Exchange Event This example demonstrates that the surface tag technology can be used for MACS enrichment of a Tag 2 (SBP) or depletion of Tag1 (Myc). Additionally, the presence of Tag2 (SBP) can be used to monitor the incorporation of the gene of interest (GOI) after a successful tag exchange event. A starting mixed population of two engineered monoclone cell lines, APL-3015 and APL-4535, was used. The cell populations were mixed as 90% Myc positive APL-3015 cells and 10% SBP positive APL-4535 cells. The Tag exchange receiver site (TERS) within the APL-4535 cells encodes an SBP epitope CST and a full-length FLAG tag GOI encoding an intracellular protein, while the TERS within the APL-3015 cells encoded a Myc epitope CST and RFP selection gene. Magnetic affinity cell sorting (MACS) was used to enrich the SBP positive APL-4535 cells from the mixed population. In a separate experiment, MACS was used to deplete the Myc positive APL-3015 cells from the mixed population.

In the first instance, the mixed cell population was labeled with an anti-SBP-Alexa 488 fluorophore and subsequently incubated with anti-mouse IgG iron beads. The SBP labeled cells were enriched using MACS and counter stained with anti-c-Myc-Alexa 405 fluorophore. FIG. 8a depicts a percentage of SBP and Myc positive cells in three experimental steps, 1) pre-MACS to ensure the starting ratio of SBP and Myc positive cells in the mixed cell population, 2) flow through to assess the percentage of SBP and Myc positive cells that were not captured by the MACS column when the column is placed in a magnetic field and 3) bound fraction is used to assess the percentage of SBP and Myc positive cells that were captured by the MACS column. All three fractions were counter stained with anti-c-Myc Alexa 405 fluorophore and data was acquired on the BD Influx instrument. FIG. 8b demonstrates the successful enrichment of SBP positive cells by the lack of SBP positive cells in the flow through fraction (<0.01), while following the SBP targeted enrichment 95% of the bound cells were SBP positive.

To demonstrate the use of the surface tag technology to MACS-deplete base cell line expressing Tag1 (Myc) from a mixed cell population all cells were labelled with anti-c-Myc-Alexa 405 fluorophore and incubated with anti-mouse IgG iron beads. The labeled cells were depleted using MACS and fractions were collected as indicated. All three fractions were counter stained with anti-SBP-Alexa 488 and data was acquired on the BD Influx instrument. The successful depletion of Myc positive cells was demonstrated by reduced number of Myc positive cells (25%) and increased number of SBP positive cells (75%) in the flow-through fraction.

Additionally, to demonstrate that the presence of Tag2 (SBP) could be used as a reporter to monitor the incorporation of the GOI after a successful tag exchange event, a total of 546 SBP positive individual monoclones were assessed whether they encoded the SBP-linked GOI. The chart in FIG. 8c shows that 96.52% of the SBP positive cells did encode the GOI, while 3.48% of the SBP positive cells did not express the GOI.

The results demonstrate that the surface tag technology is suitable for enrichment of monoclones expressing Tag2 (SBP) or depletion of unmodified base lines (monoclones expressing Tag1 (Myc)) from a mixed cell population after a successful tag exchange. Furthermore, the presence of Tag2 (SBP) correlated with the incorporation of the GOI after a successful tag exchange event and therefore presence of Tag2 (SBP) on the cell surface can be used as an indication that the GOI has been successfully delivered into the TERS within the engineered cell line.

Example 4—Composition and Operation of the Cell Surface Tag Exchange (CSTE) System Using Barcodes This example describes a schematic representation of the concept of using the CSTE system for barcoding engineered cells expressing a GOI.

FIG. 9 is a schematic representation of using the CSTE system to barcode cells expressing the GOIs. Panels a and b depict the system components, with a pool of Tag Exchange Donor Vectors (TEDV), and an engineered cell containing the Tag Exchange Receiver Site (TERS), respectively.

Each TEDV encodes RMCE elements at the 5' and 3' termini of the construct, which are paired with the RMCE sites contained within the TERS. The RMCE element at the 5' end of the TEDV construct is encoded within a sequence that represents a 3' intron fragment, wherein immediately to the 3' of the RMCE element are the 3' elements of an intron, including a branch point sequence, polypyrimidine tracts and splice acceptor site. Thus, the RMCE is contained within a 'non-functional' and non-coding intron sequence, and where the 3' intron fragment contained within the TEDV lacks a 5' splice donor site. Immediately 3' of the splice acceptor site, the TEDV encodes a 3' exon of a cell surface tag (CST), meaning the exon encodes the portion of the CST containing unique molecular binding motifs. The CST sequence is encoded in the 5' to 3' direction, where the TEDV also encodes the gene of interest (GOI) to be integrated into the TERS encoded in the 3' to 5' direction.

Each CST in this example is composed of two different epitopes from a selection of 3 potential unique epitopes (A, B, C), which can be combined into 6 possible unique combinations. As the arrangement of each epitope is difficult to distinguish via current techniques, AB is effectively equivalent to BA. In this example, the AX combinations have been assigned to a GOI family, with three variants (GOI a-i, a-ii and a-iii), and the BX combinations have been assigned to a second GOI family with three variants (GOI b-i, b-ii, b-iii). The individual TEDVs in this example are pooled (FIG. 9a).

The central part of the TERS, contained within an engineered cell, encodes elements distinct from those of the TEDV, though with the same architecture. That is, between the RMCE elements, paired with those of TEDV, the TERS encodes a CST exon distinct from that of the TEDV-encoded CST, with a splice acceptor site and associated 3' intronic sequence immediately to the 5' of this CST. Similarly, a selection gene is encoded in the antisense direction within the TERS, as is the GOI in the TEDV. At the 5' end of the construct, promoter sequences are included, to drive transcription of the CST. To the 3' of this promoter sequence, a transmembrane domain (TD) exon is encoded, with a 5' intron sequence immediately to the 3'. This means that the TD exon and CST exon, encoded in frame with an RMCE element containing intron, are produced as a contiguous transcript that is spliced to adjoin the exons into a single coding mRNA. The TERS-encoded TD-CST product is expressed on the cell surface. At the 3' terminus of the TERS construct is a separate promoter element that drives transcription of the selection gene in the 3' to 5' direction, resulting in the expressed selection gene (FIG. 9b).

The introduction of the TEDV pool to the engineered cell population containing the TERS, along with an appropriate expression construct for recombinase specific for the paired RMCE elements in the TEDV/TERS, results in the execution of RMCE, and the generation of a pool of derivative engineered cells expressing the GOIs (FIG. 9c). The TERS-encoded elements have exchanged for the TEDV-encoded elements. The derivative engineered cells thus express the TEDV-encoded CSTs at the cell surface, as a TD-CST product with the originally TERS-encoded TD, and the GOI.

Overall, execution of RMCE between the pool of TEDV and TERS results in the generation of a derivative pool of engineered cells that has lost expression of the selection gene and the original TERS-encoded CST, and each cell in the pool has gained expression of one of the members of the TEDV-encoded CST and GOI from the TEDV pool. The pool of engineered cells expressing GOI can be further analysed/isolated into its individual members via FACS, for example, being isolated based on the expression of the unique CST barcode (FIG. 9d). This can be achieved either as bulk populations of a desired barcode, or individual cell isolation via single cell sorting methods, for instance. Alternatively, analysis of the pool can be conducted via FAC without sorting using the barcode as a means to identify populations of interest within the digital datasets, with secondary analysis of cellular function, for example, to correlate variant GOI expression or cellular function.

To demonstrate the concept that the CST can be composed of multiple epitopes, ACL-1 and ACL-5 cells were transfected with either a plasmid encoding a CST or a control plasmid without a CST (FIG. 9e). The CST was comprised of 3 unique epitopes, FLAG, MYC and HA and is represented by sequence SEQ ID 20. Cells were transfected using chemical transfection (ACL-5) or electroporation (ACL-1) using standard methods known by those skilled in the art. After 48 hours cells were harvested and stained with the cognate antibodies conjugated with a fluorophore: anti-FLAG-PE, anti-MYC-AF647 and anti-HA-AF488. Cells were analysed by flow cytometry, live cells were gated by Forward Scatter (FSC) and Side Scatter (SSC). The Mean Fluorescence Intensity (MFI) of live cells was determined for each of the 3 epitopes, and the percentage of live cells expressing the respective epitopes. All three epitopes were detected in high proportions and intensity for the cells in the sample transfected with the plasmid encoding the barcoded CST, compared to the empty vector, thereby demonstrating a CST composed of multiple epitopes.

The results demonstrate that the surface tag technology is suitable for barcoding cell lines as the CST can be composed of multiple epitopes.

List of Abbreviations

AAVS1 Adeno-associated virus integration site 1
APC Antigen-presenting cell
Cas9 CRISPR-associated gene 9
CMV Cytomegalovirus
cre Cre recombinase
CRISPR Clustered regularly interspaced short palindromic repeats
CST Cell surface tag
CSTE Cell surface tag exchange
DMSO Dimethyl sulfoxide
DNA Deoxyribonucleic acid
DPBS Dulbecco's phosphate buffered saline
DSB Double-strand break
dUTP Deoxyuridine Thiphosphate
EDTA Ethylenediaminetetraacetic acid
EF1 alpha Elongation factor alpha (for eukaryotic translation)
FACS Fluorescence-activated cell sorting
FAM Fluorescein amidite
FBS Fetal bovine serum
FLP Flippase
FRT Flippase recognition target
GFP Green fluorescent protein
GOI Gene of interest
gRNA Guide ribonucleic acid
HDR Homology directed recombination
HLA Human leukocyte antigen
IRES Internal ribosomal entry site
MACS Magnetic-activated cell sorting
NEB New England biolabs
NHEJ Non-homologous end joining
ORF Open reading frame
PCR Polymerase chain reaction
RFP Red fluorescent protein
RMCE Recombinase mediated cassette exchange
RPMI Roswell Park Memorial Institute
RSV
Respiratory syncytial virus
Reverse Transcription
RT
RNA Ribonucleic acid
SBP Streptavidin binding peptide
SSR Site-specific recombinase
SV40 Simian virus 40
SV40 pA Simian virus 40 poly (A)
TAA Tumour-associated-antigens
TALEN Transcription-like effector nuclease
TAE Tris-acetate-EDTA
T-cells T lymphocytes
TCR T-cell Receptor
TCS Target coding sequence
TD Transmembrane domain
TEDV Tag-exchange donor vector
TERS Tag-exchange receiver site
rRNA Ribosomal RNA
tRNA Transfer RNA
UTR Untranslated region
ZNF Zinc finger nuclease

List of Definitions

Amplicon: a piece of DNA or RNA that is the source and/or product of artificial amplification using various methods including PCR.

Antibody: Affinity molecule that is expressed by specialized cells of the immune system called B-cells and that contains of two chains. B-cells express a very large and very diverse repertoire of antibodies that do generally not bind self proteins but can bind and neutralize pathogens or toxins that would threaten the host. Natural or artificially engineered antibodies are often used as affinity reagents.

Auxotroph: a mutant organism (especially a bacterium or fungus) that requires a particular additional nutrient which the normal strain does not.

Cis-acting element: regions of non-coding DNA that regulate the transcription of nearby ORFs.

CST: co-integrated cell surface tag that allows reporting of an integrated gene of interest CSTE system: a system that operates as a donor/receiver pair, wherein the tag-exchange donor vector acts to deliver a gene of interest sequence, and a cell-surface tag exon to a paired tag-exchange receiver site contained within the genome of an engineered cell line.

Derivative Engineered Cell: an engineered cell, that has been further genetically modified to exchange CST and integrate GOI DNA: Desoxyribonucleic acid. Chemical name of the molecule that forms genetic material encoding genes and proteins.

Engineered Cell: A cell whereby the genome has been engineered through genetic modification.

Epitope: Region on an antibody target that is bound by an antibody or other affinity reagent.

Eukaryotic conditional regulatory element: A DNA sequence that can influence the activity of a promoter, which may be induced or repressed under defined conditions Eukaryotic Promoter: A DNA sequence that encodes a RNA polymerase binding site and response elements The sequence of the promoter region controls the binding of the RNA polymerase and transcription factors, therefore promoters play a large role in determining where and when your gene of interest will be expressed.

Eukaryotic terminator/Signal terminator: A DNA sequence that are recognized by protein factors that are associated with the RNA polymerase II and which trigger the termination process of transcription. It also encodes the poly-A signal FACS/Flow Cytometry: Fluorescence-activated cell sorting. Flow cytometry is a technique by which individual cells can be analyzed en masse for the expression of specific cell surface and intracellular markers. A variation of that technique, cell sorting, allows cells that carry a defined set of markers to be retrieved for further analysis.

Flippase: A recombinase (Flippase, Flp) derived from the 2 μm plasmid of baker's yeast *Saccharomyces cerevisiae.*

Fluorescent (protein) marker: Molecule that has specific extinction and emission characteristics and can be detected by Microscopy, FACS and related techniques.

Gene cis acting elements: are present on the same molecule of DNA as the gene they regulate whereas trans-regulatory elements can regulate genes distant from the gene from which they were transcribed. Cis-regulatory elements are often binding sites for one or more trans-acting factors.

Genetic barcoding: DNA barcoding is a taxonomic method that uses a short genetic marker in an organism's DNA to identify it as belonging to a particular species.

GOI: gene of interest defined as any nucleic acid coding or non-coding sequence of interest.

Heterospecific recombinase sites: A DNA sequence that is recognized by a recombinase enzyme to promote the crossover of two DNA molecules Homologous arms: A stretch of DNA that has near identical sequence identity to a complement homologous arm and therefore promote the exchange of two DNA molecules by the cellular process, homology directed repair.

Insulator: A DNA sequence that prevents a gene from being influenced by the activation or repression of nearby genes. Insulators also prevent the spread of heterochromatin from a silenced gene to an actively transcribed gene.

Integration: The physical ligation of a DNA sequence into a chromosome of a cell Internal ribosome entry site (IRES): A DNA sequence that once transcribed encodes a RNA element that allows the initiation of translation in a cap-independent manner Intron: Noncoding sections of an RNA transcript, or the DNA encoding it, that are spliced out before the RNA molecule is translated into a protein Intron branch point sequence: branch point nucleotide that initiates a nucleophilic attack on the 5' donor splice site. The free end of the upstream intron then initiates a second nucleophilic attack on the 3' acceptor splice site, releasing the intron as an RNA lariat and covalently combining the two exons K is a nucleotide code indicating Keto (K=G or T)

Kozak Sequence: Short sequence required for the efficient initiation of translation M is a nucleotide code indicating aMino (M=A or C)

MACS: Magnetic activated cell sorting: Cellular isolation technique in which cells are labelled with affinity molecules that contain magnetic particles for separation using magnetic fields.

Matched: When two components encode genetic elements that direct and restrict the interaction between the complemented components Monoclone cell line: A defined group of cells produced from a single ancestral cell by repeated cellular replication. N is a nucleotide code indicating aNy nucleotide (N=A, T, C or G)

Native: an entity that is naturally occurring to the cell

Negative Selection Marker: A selectable marker that confers negative selection of a vector and/or of host organism carrying said marker-bearing vector Non-coding gene: A non-protein coding DNA sequence that is transcribed into functional non-coding RNA molecules Origin of replication: a particular sequence in a vector, plasmid or genome at which replication is initiated.

ORF: Open reading frame. Stretch of genetic material that encodes a translation frame for synthesis of a protein (polypeptide) by the ribosome Overhang: A single stranded sequence at the terminus of a double stranded nucleic acid molecule. Often referred to as sticky or cohesive ends.

PCR: Polymerase chain reaction in which a specific target DNA molecule is exponentially amplified Peptide: short string of amino acids, typically between 6-30 amino acids in length Phenotypic analysis: Analysis of the observable characteristics of a cell.

Plasmid: A genetic construct can replicate independently of the chromosomes, typically a small circular DNA strand in the cytoplasm of a bacterium or protozoan.

Polypeptide: Protein consisting of a stretch of peptides, forming a three-dimensional structure.

Polypirimidine motif: (CnTn) motif high in pyrimidines and is present upstream of the CAG intron 3' end.

Positive Selection Marker: A selectable marker that confers positive selection of a vector and/or host organism carrying said marker-bearing vector Primer: Short DNA sequence that allows specific recognition of a target DNA sequence for example during a PCR.

Promoter: Regulatory DNA element for the controlled initiation of gene expression Recombinase: Enzymes that mediate genetic recombination, catalyses RMCE.

Reporter Element: A genetic element that mediates a reported signal in the organism or vector bearing said element. May be used as a positive or negative selection maker.

Restriction Enzyme Cleavage Sequence: The genetic sequence cleaved by a restriction enzyme, which can be intrinsic or intrinsic to the recognition sequence of said restriction enzyme Restriction Enzyme Recognition Sequence: The genetic sequence recognised and engaged by a restriction enzyme RMCE: Recombinase-mediated cassette exchange. Exchange of genetic material at the genomic receiver site catalysed by a recombinase.

Slice acceptor site: A DNA sequence at the 3' end of the intron AM, APX CM or affinity reagent for interaction with cells with TCRsp on the surface, or TCRsp based reagents Slice donor site: A DNA sequence at the 5' end of the intron Suicide gene: A gene that will mediate cell death within the host organism carrying said gene. May be used as a positive or negative selection marker.

Synthetic: an entity that is artificially generated

TEDV: tag-exchange donor vector paired to the tag-exchange receiver site contained within the genome of an engineered cell. It is used to deliver a gene of interest and a cell-surface tag exon TERS: paired tag-exchange receiver site contained within the genome of an engineered cell line Type II transmembrane domain: single non-cleavable transmembrane stretch of hydrophobic residues close to the N terminus which serves as a combined signal/anchor sequence, with the N terminal portion on the interior of the membrane and the C terminal 5 portion exposed on the cell exterior or in the ER lumen.

Vector: A vector is a genetic construct that carries genetic information. In the present context vector usually describes plasmidic DNA vectors. A vector can represent any such construct that can be propagated and selected in a host organism.

W is a nucleotide code indication Weak (W=A or T)

60

The invention claimed is:

1. A combined system comprising two separate components, wherein a first component is a tag-exchange donor vector (TEDV) encoding a first cell surface tag (CST) exon flanked by a 3' intron fragment and a gene in an antisense orientation, the TEDV containing no promoter sequences, and a second component is an engineered cell containing within its genome a tag-exchange receiver site (TERS) encoding a second CST exon, which is different from the first CST exon and adjoined by a full intron sequence to an exon encoding a transmembrane domain, and also encoding a reporter
gene in an antisense orientation,
wherein paired recombinase mediated cassette exchange
(RMCE) elements are encoded by each of the TEDV
and TERS such that execution of RMCE between the
TEDV and TERS results in exchange of the reporter
gene for the gene encoded by the TEDV, and exchange
of the first CST exon for the second CST exon, gen-
erating a derivative engineered cell, wherein the deriva-
tive engineered cell expresses the first CST exon and
gene, in place of the second CST exon and the reporter
gene.
2. The combined system according to claim 1, wherein the
TEDV comprises:
a first RMCE element;
a 3' intron fragment;
the first CST exon;
a first transcriptional terminator;
a second transcriptional terminator;
the gene;
a Kozak sequence; and
a second RMCE element,
wherein the first CST exon and first transcriptional ter-
minator are encoded in an antisense orientation from
the gene and associated transcriptional terminator and
Kozak sequences.
3. The combined system according to claim 2, wherein the
second component is a TERS comprising:
a transcriptional promoter element;
a Kozak sequence;
a transmembrane domain exon;
the full intron sequence;
a first RMCE element encoded within the intron
sequence;
the second CST exon;
a first transcriptional terminator;
a second transcriptional terminator; a reporter gene;
a Kozak sequence;
a second RMCE element; and
a second transcriptional promoter element,
wherein the transmembrane domain exon and the second
CST exon are encoded in an antisense orientation from
the reporter gene, such that the first transcriptional
promoter element drives transcription of both the trans-
membrane domain and the second CST exon, and the
second transcriptional promoter element drives tran-
scription of the reporter gene.
4. The combined system according to claim 1, wherein the
TERS comprises:
a transcriptional promoter element; a Kozak sequence;
a transmembrane domain exon;
the full intron sequence;
a first RMCE element encoded within the full intron
sequence;
the second CST exon;
a first transcriptional terminator;
a second transcriptional terminator a reporter gene;
a Kozak sequence;
a second RMCE element; and
a second transcriptional promoter element,
wherein the transmembrane domain exon and the second
CST exon are encoded in an antisense orientation from
the reporter gene, such that the first transcriptional
promoter element drives transcription of both the trans-
membrane domain and the second CST exon, and the
second transcriptional promoter element drives tran-
scription of the reporter gene.

5. The combined system according to claim 1, wherein the
first RMCE element of the TEDV is paired with the first
RMCE element of the TERS, and the second RMCE element
of the TEDV is paired with the second RMCE element of the
TERS.
6. The combined system according to claim 1, wherein
each CST exon comprises a sequence encoding one or more
molecular affinity tags, wherein the CST exons encoded by
the TEDV and TERS are different.
7. The combined system according to claim 1, wherein the
engineered cell contains a single TERS in its genome.
8. A method for generating derivative engineered cells
expressing a TEDV-encoded gene from a TERS, said
method comprising,
generating a TEDV encoding a first CST exon and a gene
and containing no promoter sequences;
delivering said TEDV to an engineered cell line contain-
ing a paired TERS encoding a second CST exon and
also encoding a reporter gene in an antisense orienta-
tion, along with a recombinase enzyme, wherein the
recombinase enzyme mediates cassette exchange
between the matching RMCE elements encoded in the
TEDV and the TERS;
contacting at least one cell of the engineered cell line with
two or more affinity reagents specific for both the
TEDV-encoded CST exon and the TERS-encoded CST
exon;
selecting at least one derivative engineered cell on the
basis of diminished expression of the reporter gene and
TERS-encoded CST exon, and increased expression of
the TEDV-encoded CST exon.
9. The method according to claim 8, wherein the affinity
reagents are fluorescently labelled to detect diminished
expression of TERS-encoded CST exon and increased
expression of TEDV-encoded CST exon, to enable cell
partitioning and selection based on said expression by way
of florescence activated cell sorting.
10. The method according to claim 8, wherein the affinity
reagents are immobilised on a substrate such that cells
expressing TERS-encoded CST exon may be depleted, or
cells expressing TEDV-encoded CST exon may be enriched,
in a target cell population using substrate affinity methods.
11. A method for generating multiple derivative engi-
neered cells expressing a range of TEDV-encoded gene,
from a pool of TEDVs, said method comprising,
generating a library of two or more TEDVs, each encod-
ing a unique gene sequence, each with a unique TEDV-
encoded CST exon, and each containing no promoter
sequences; delivering said library of TEDVs as a pool
to an engineered cell line containing a paired TERS
encoding a unique CST exon and also encoding a
reporter gene in an antisense orientation, along with a
recombinase enzyme, wherein the recombinase
enzyme mediates cassette exchange between matching
RMCE elements encoded in the TEDVs and TERS;
contacting cells with three or more affinity reagents
specific for both the multiple TEDV-encoded CST
exons and the TERS-encoded CST exon;
selecting at least one derivative engineered cell on the
basis of diminished expression of the reporter gene and
TERS-encoded CST exon, and increased expression of
each of the unique TEDV-encoded CST exons.
12. A method for cell lineage tracing of derivative engi-
neered cells expressing a range of TEDV-encoded gene,
within a pool of engineered cells generated by generating a
library of two or more TEDVs, each encoding a unique gene
sequence, each with a unique TEDV-encoded CST exon, and each containing no promoter sequences and delivering said library of TEDVs as a pool to an engineered cell line containing a paired TERS encoding a unique CST exon and also encoding a reporter gene in antisense orientation, along with a recombinase enzyme, wherein the recombinase enzyme mediates cassette exchange between matching RMCE elements encoded in the TEDVs and the TERS, said method comprising:

contacting cells with two or more affinity reagents specific for the multiple TEDV-encoded CST exons; and analyzing the TEDV-encoded genes of derivative engineered cells on the basis of expression of each of the unique TEDV-encoded CST exons.

13. A tag-exchange donor vector (TEDV) encoding a cell surface tag (CST) exon flanked by a 3' intron fragment, a gene in an antisense orientation, and containing no promoter sequences.

14. The tag-exchange donor vector (TEDV) according to claim 13, comprising:

a first RMCE element;

a 3' intron fragment;

a CST exon;

a first transcriptional terminator;

a second transcriptional terminator;

a gene;

a Kozak sequence; and a second RMCE element, wherein the CST exon and first transcriptional terminator are encoded in an antisense orientation from the gene and associated transcriptional terminator and Kozak sequences.

15. An engineered cell containing within its genome a tag-exchange receiver site (TERS), encoding a cell surface tag (CST) exon adjoined by a full intron sequence to an exon encoding a transmembrane domain, and also encoding a reporter gene in an antisense orientation, wherein recombinase mediated cassette exchange (RMCE) elements are included in the TERS such that execution of RMCE between the TERS and a tag-exchange donor vector (TEDV) containing no promoter sequences results in exchange of the reporter gene for a gene encoded by the TEDV.

16. The engineered cell according to claim 15, wherein said TERS comprises:

a first transcriptional promoter element;

a Kozak sequence;

a transmembrane domain exon; an intron;

a first RMCE element; a CST exon;

a first transcriptional terminator;

a second transcriptional terminator; a reporter gene;

a Kozak sequence;

a second RMCE element; and a second transcriptional promoter element, wherein the transmembrane domain exon and CST exon are encoded in an antisense orientation from the reporter gene, such that the first transcriptional promoter element drives transcription of the combined transmembrane domain and CST exon, and the second transcriptional promoter element drives transcription of the reporter gene.

* * * * *